United States Patent
Rozema et al.

(10) Patent No.: US 8,426,554 B2
(45) Date of Patent: Apr. 23, 2013

(54) IN VIVO POLYNUCLEOTIDE DELIVERY CONJUGATES HAVING ENZYME SENSITIVE LINKAGES

(75) Inventors: David B. Rozema, Middleton, WI (US); Darren H. Wakefield, Fitchburg, WI (US); David L. Lewis, Madison, WI (US); Jon A. Wolff, Madison, WI (US); Andrei V. Blokhin, Fitchburg, WI (US); Jonathan D. Benson, Stoughton, WI (US); Jeffrey C. Carlson, Madison, WI (US); Philipp Hadwiger, Kulmbach (DE); Eric A. Kitas, Aesch BL (CH); Torsten Hoffmann, Weil am Rhein (DE); Kerstin Jahn-Hoffmann, Neu-Isenburg (DE); Peter Mohr, Basel (CH); Hans Martin Mueller, Munich (DE); Guenther Ott, Bayreuth (DE); Ingo Roehl, Memmelsdorf (DE)

(73) Assignee: Arrowhead Madison Inc., Madison, WI (US)

( * ) Notice: Subject to any disclaimer, the term of this patent is extended or adjusted under 35 U.S.C. 154(b) by 0 days.

(21) Appl. No.: 13/336,028

(22) Filed: Dec. 23, 2011

(65) Prior Publication Data

US 2012/0172412 A1 Jul. 5, 2012

Related U.S. Application Data

(60) Provisional application No. 61/427,845, filed on Dec. 29, 2010.

(51) Int. Cl.
*C07K 16/00* (2006.01)
(52) U.S. Cl.
USPC .......................................................... 530/300
(58) Field of Classification Search .................. None
See application file for complete search history.

(56) References Cited

U.S. PATENT DOCUMENTS

| | | | |
|---|---|---|---|
| 6,214,345 B1 * | 4/2001 | Firestone et al. | 424/178.1 |
| 7,091,186 B2 | 8/2006 | Senter et al. | |
| 7,541,330 B2 * | 6/2009 | Santi et al. | 514/1.1 |
| 7,553,816 B2 | 6/2009 | Senter et al. | |
| 2004/0162260 A1 | 8/2004 | Rozema et al. | |
| 2008/0269450 A1 | 10/2008 | Wakefield et al. | |

FOREIGN PATENT DOCUMENTS

| | | |
|---|---|---|
| WO | WO 2008/022309 A3 | 2/2008 |
| WO | WO 2009/073809 A2 | 6/2009 |
| WO | WO 2011/005980 A1 | 1/2011 |
| WO | WO 2011/154331 A1 | 12/2011 |

OTHER PUBLICATIONS

He et al., Biotechnology: Pharmaceutical Aspects, Prodrugs: Challenges and Rewards Part 1; Edited by Stella et al., published by Springer, 2007, chapter 3.6, p. 239.*
Carl PL et al. "A novel connector linkage applicable in prodrug design" Journal of Medicinal Chemistry (1981) 24(5): 479-480.
de Groot FMH et al. :Synthesis and Biological Evaluation of Novel Prodrugs of Anthracyclines for Selective Activation by the Tumor-Associated Protease Plasmin Journal of Medicinal Chemistry (1999) 42: 5277-5283.
Doronina SO et al. "Development of potent monoclonal antibody auristatin conjugates for cancer therapy" Nature Biotechnology (2003) 21: 778-784.
Dubowchik GM et al. "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity." Bioconjugate Chemistry (2002) 13: 855-869.
Dubowchik GM et al. "Cathepsin B-Sensitive Dipeptide Prodrugs. 2. Models of Anticancer Drugs Paclitaxel (Taxol(R)), Mitomycin C, and Doxorubicin." Bioorganic & Medicinal Chemistry Letters (1998) 8(23): 2247-3352.
Dubowchik GM et al. "Cathepsin B-sensitive dipeptide prodrugs. 1. A model study of structural requirements for efficient release of doxorubicin" Bioorganic & Medicinal Chemistry Letters (1998) 8(23): 3341-3346.
Greenwald RB et al. "Drug delivery systems employing 1,4- or 1,6-elimination: poly(ethylene glycol) prodrugs of amine-containing compounds" Journal of Medicinal Chemistry (1999) 42(18): 3657-3667.
PetersonJJ et al. "Cathepsin Substrates as Cleavable Peptide Linkers in Bioconjugates, Selected from a Fluorescence Quench Combinatorial Library" Bioconjugate Chemistry (1998) 9; 618-626.
Rozema DB et al. "Dynamic PolyConjugates for targeted in vivo delivery of siRNA to hepatocytes." Proceedings from the National Academy of Sciences USA (2007) 104(32):12982-12987.
Toki BE et al. "Protease-Mediated Fragmentation of p-Amidobenzyl Ethers: A New Strategy for the Activation of Anticancer Prodrugs" Journal of Organic Chemistry (2002) 67: 1866-1872.

* cited by examiner

*Primary Examiner* — Marcela M Cordero Garcia
*Assistant Examiner* — Kaipeen Yang
(74) *Attorney, Agent, or Firm* — Kirk Ekena

(57) ABSTRACT

The present invention is directed compositions for delivery of RNA interference (RNAi) polynucleotides to cells in vivo. The compositions comprise amphipathic membrane active polyamines reversibly modified with enzyme cleavable dipeptide-amidobenzyl-carbonate masking agents. Modification masks membrane activity of the polymer while reversibility provides physiological responsiveness. The reversibly modified polyamines (dynamic polyconjugate or DPC) are further covalently linked to an RNAi polynucleotide or co-administered with a targeted RNAi polynucleotide-targeting molecule conjugate.

14 Claims, 6 Drawing Sheets

Dipeptide masking agent

Dipeptide masking agent linked to a polyamine.

A.

NAG-AlaCit-PABC-PNP

B.

NAG-GluGly-PABC-PNP

C.

NAG-PEG4-PheCit- PABC-PNP

D.

NAG-PEG7-PheCit-PABC-PNP

E.

PEG-GlyGly-PABC-PNP

F.

PEG-AsnGly-PABC-PNP

G.

PEG-PheLys-PABC-PNP

H.

PEG-ValCit-PABC-PNP

I.

PEG-AlaAsn-PABC-PNP

J.

PEG-PheLys(CH$_3$)$_2$-PABC-PNP

IN VIVO POLYNUCLEOTIDE DELIVERY CONJUGATES HAVING ENZYME SENSITIVE LINKAGES

CROSS-REFERENCE TO RELATED APPLICATIONS

This application claims the benefit of U.S. Provisional Application No. 61/427,845, filed 29 Dec. 2010.

BACKGROUND OF THE INVENTION

The delivery of polynucleotide and other substantially cell membrane impermeable compounds into a living cell is highly restricted by the complex membrane system of the cell. Drugs used in antisense, RNAi, and gene therapies are relatively large hydrophilic polymers and are frequently highly negatively charged. Both of these physical characteristics severely restrict their direct diffusion across the cell membrane. For this reason, the major barrier to polynucleotide delivery is the delivery of the polynucleotide across a cell membrane to the cell cytoplasm or nucleus.

One means that has been used to deliver small nucleic acid in vivo has been to attach the nucleic acid to either a small targeting molecule or a lipid or sterol. While some delivery and activity has been observed with these conjugates, the nucleic acid dose required with these methods has been prohibitively large.

Numerous transfection reagents have also been developed that achieve reasonably efficient delivery of polynucleotides to cells in vitro. However, in vivo delivery of polynucleotides using these same transfection reagents is complicated and rendered ineffective by in vivo toxicity, adverse serum interactions, and poor targeting. Transfection reagents that work well in vitro, cationic polymers and lipids, typically form large cationic electrostatic particles and destabilize cell membranes. The positive charge of in vitro transfection reagents facilitates association with nucleic acid via charge-charge (electrostatic) interactions thus forming the nucleic acid/transfection reagent complex. Positive charge is also beneficial for nonspecific binding of the vehicle to the cell and for membrane fusion, destabilization, or disruption. Destabilization of membranes facilitates delivery of the substantially cell membrane impermeable polynucleotide across a cell membrane. While these properties facilitate nucleic acid transfer in vitro, they cause toxicity and ineffective targeting in vivo. Cationic charge results in interaction with serum components, which causes destabilization of the polynucleotide-transfection reagent interaction, poor bioavailability, and poor targeting. Membrane activity of transfection reagents, which can be effective in vitro, often leads to toxicity in vivo.

For in vivo delivery, the vehicle (nucleic acid and associated delivery agent) should be small, less than 100 nm in diameter, and preferably less than 50 nm. Even smaller complexes, less that 20 nm or less than 10 nm would be more useful yet. Delivery vehicles larger than 100 nm have very little access to cells other than blood vessel cells in vivo. Complexes formed by electrostatic interactions tend to aggregate or fall apart when exposed to physiological salt concentrations or serum components. Further, cationic charge on in vivo delivery vehicles leads to adverse serum interactions and therefore poor bioavailability. Interestingly, high negative charge can also inhibit targeted in vivo delivery by interfering with interactions necessary for targeting, i.e. binding of targeting ligands to cellular receptors. Thus, near neutral vehicles are desired for in vivo distribution and targeting. Without careful regulation, membrane disruption or destabilization activities are toxic when used in vivo. Balancing vehicle toxicity with nucleic acid delivery is more easily attained in vitro than in vivo.

Rozema et al., in U.S. Patent Publication 20080152661, provided a means to reversibly regulate membrane disruptive activity of a membrane active polyamine using disubstituted maleic anhydride modification. Maleamate linkages, formed by reaction of a maleic anhydride with an amine are pH labile in a pH range suitable for in vivo delivery. This process allowed membrane active polymers to be used for in vivo delivery or nucleic acid. We now provide modified membrane active polymers having dipeptide-amidobenzyl-carbamate linkages. The dipeptide-amidobenzyl-carbamate linkages are reversible and physiologically responsive. Unlike pH-labile maleamate linkages from by modification with disubstituted maleic anhydride, the polymer modification agents linkage described herein generate enzymatically cleavable linkages that are more stable in in vivo circulation.

SUMMARY OF THE INVENTION

In a preferred embodiment we describe masking agents for reversibly modifying and inhibiting membrane activity of an amphipathic membrane active polyamine comprising: a steric stabilizer or targeting ligand attached to a dipeptide-amidobenzyl-carbonate, referred to herein as dipeptide masking agents or protease cleavable masking agents. The dipeptide masking agents have the general form:

$R\text{-}A^1A^2\text{-amidobenzyl-carbonate}.$ wherein R is a steric stabilizer or targeting ligand, $A^1$ is an amino acid, and $A^2$ is an amino acid. Reaction of the masking agent carbonate with a polymer amine yields a carbamate linkage. The masking agent is stable until the dipeptide is cleaved in vivo by an endogenous protease, thus cleaving the steric stabilizer or targeting ligand from the polyamine. Following enzymatic cleavage after the dipeptide (between $A^2$ and the amidobenzyl), the amidobenzyl-carbamate undergoes a spontaneous rearrangement which results in regeneration of the polymer amine. Preferably R is neutral. More preferably, R is uncharged. A preferred steric stabilizer is a polyethylene glycol (PEG). A targeting ligand may be selected from the list comprising haptens such as digoxigenin, vitamin such as biotin, antibody, monoclonal antibody, and cell surface receptor ligand. A targeting ligand may be linked to the dipeptide via a linker such as a PEG linker. A preferred cell surface receptor ligand is an asialoglycoprotein receptor (ASGPr) ligand. A preferred ASGPR ligand is an N-Acetylgalactosamine (NAG). A preferred dipeptide consists of a hydrophobic amino acid linked to a hydrophilic uncharged amino acid via an amide bond. A preferred amidobenzyl group is a p-amidobenzyl group. A preferred carbonate is an activated amine reactive carbonate.

In a preferred embodiment, the invention features a composition for delivering an RNA interference (RNAi) polynucleotide to a cell in vivo comprising: a masked amphipathic membrane active polyamine (delivery polymer) wherein the polyamine is masked by reversible modification with the dipeptide masking agents described herein and an RNAi polynucleotide. The delivery polymer can be covalently linked to the RNAi polynucleotide. A preferred linkage for covalent attachment of the delivery polymer to the RNAi polynucleotide is a physiologically labile linkage. In one embodiment, this linkage is orthogonal to the dipeptide masking agent linkage. Alternatively, the delivery polymer is not covalently linked to the RNAi polynucleotide and the RNAi polynucleotide is covalently linked to a targeting molecule.

In a preferred embodiment, we describe a composition comprising: an amphipathic membrane active polyamine covalently linked to: a) a plurality of targeting ligands or steric stabilizers via dipeptide-amidobenzyl-carbamate linkages; and, b) one or more polynucleotides via one or more reversible linkages. In one embodiment, dipeptide-amidobenzyl-carbamate linkage is orthogonal to the polynucleotide reversible covalent linkage. The polynucleotide-polymer conjugate is administered to a mammal in a pharmaceutically acceptable carrier or diluent.

In a preferred embodiment, we describe a composition comprising: a) an amphipathic membrane active polyamine covalently linked to a plurality of targeting ligands or steric stabilizers via dipeptide-amidobenzyl-carbamate linkages; and, b) an RNAi polynucleotide covalently linked to a targeting group selected from the list consisting of: a hydrophobic group having 20 or more carbons atoms and a galactose cluster. In this embodiment, the RNAi polynucleotide is not covalently linked to the modified amphipathic membrane active polyamine. The modified polyamine and the RNAi polynucleotide targeting group conjugate are synthesized separately and may be supplied in separate containers or a single container. The modified polyamine and RNAi polynucleotide-targeting group conjugate are administered together or separately to a mammal in pharmaceutically acceptable carriers or diluents.

A preferred dipeptide masking agent comprises a protease (peptidase) cleavable dipeptide-p-amidobenzyl amine-reactive carbonate derivative. Protease cleavable masking agents of the invention employ a dipeptide connected to an amidobenzyl activated carbonate moiety. A targeting ligand or steric stabilizer is attached to the amino terminus of a dipeptide. The amidobenzyl activated carbonate moiety is attached at the carboxy terminus of the dipeptide. Protease cleavable linkers suitable for use with the invention have the general structure:

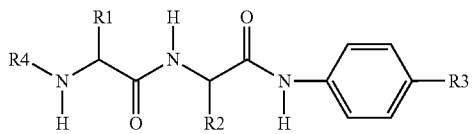

wherein R4 comprises a targeting ligand or steric stabilizer, R3 comprises an amine reactive carbonate moiety, and R1 and R2 are amino acid side chains. A preferred activated carbonate is a para-nitrophenol. However, other amine reactive carbonates known in the art are readily substituted for the para-nitrophenol. Reaction of the activated carbonate with an amine connects the targeting ligand or steric stabilizer to the membrane active polyamine via a peptidase cleavable dipeptide-amidobenzyl carbamate linkage. Enzyme cleavage of the dipeptide, between the amino acid and the amidobenzyl group removes R4 from the polymer and triggers an elimination reaction which results in regeneration of the polymer amine.

The dipeptide masking agents of the invention are useful for reversible modification/inhibition of amphipathic membrane active polyamines. A covalent bond is created by the reaction of the activated carbonate of the dipeptide masking agent with a polymer amine, particularly a primary amine. group. Hence provided herein is a conjugate comprising the dipeptide-amidobenzyl-carbonate masking agent described herein and an amphipathic membrane active polyamine:

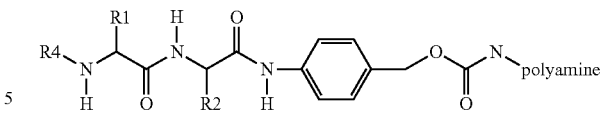

The compounds according to the present invention can be generally obtained using methods known to the person of ordinary skill in the art of organic or medicinal chemistry. Further objects, features, and advantages of the invention will be apparent from the following detailed description when taken in conjunction with the accompanying drawings.

DETAILED DESCRIPTION OF THE INVENTION

Figure 1:
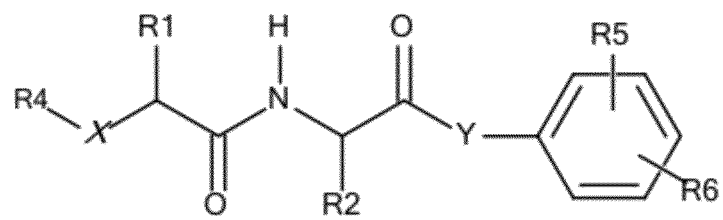
FIG. 1. Illustration showing the structure of a dipeptide masking agent wherein:
R1 and R2 are the R groups of amino acids,
R4 is a targeting ligand of a steric stabilizer,
X is —NH—, —O—, or —CH$_2$—,
Y is —NH— or —O—
R5 is at position 2, 4, or 6 and is —CH$_2$—O—C(O)—O—Z wherein Z carbonate, and
R6 is independently hydrogen, alkyl, or halide at each of positions 2, 3, 4, 5, or 6 except for the position occupied by R5.
Figure 2:
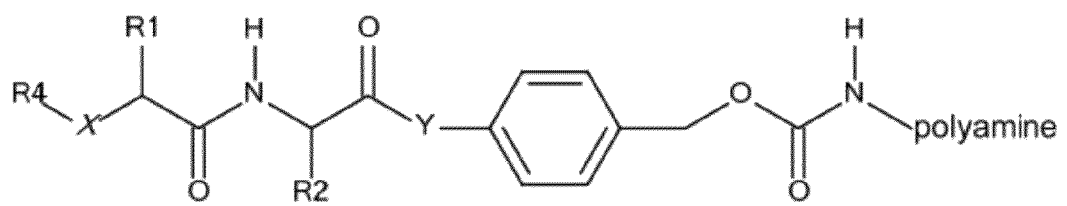
FIG. 2. Illustration showing the structure of a dipeptide masking agent linked to a polyamine wherein: R1 and R2 are the R groups of amino acids, R4 is a targeting ligand of a steric stabilizer, X is —NH—, —O—, or —CH$_2$—, and Y is —NH— or —O—.
Figure 3:
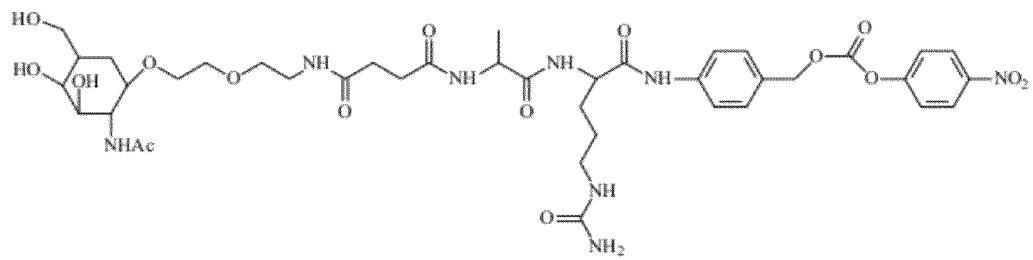
FIG. 3. Illustration shown the structures of various dipeptide masking agents.
Figure 3:
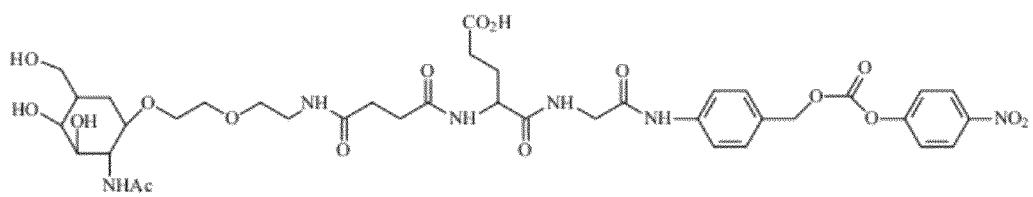
Figure 3:
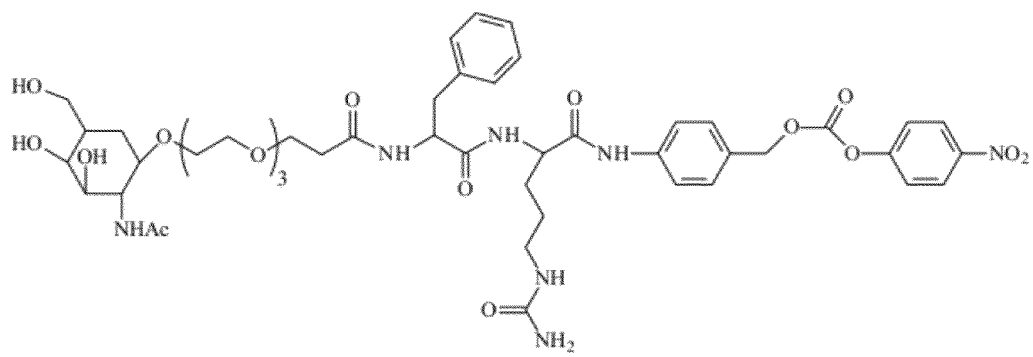
Figure 3:
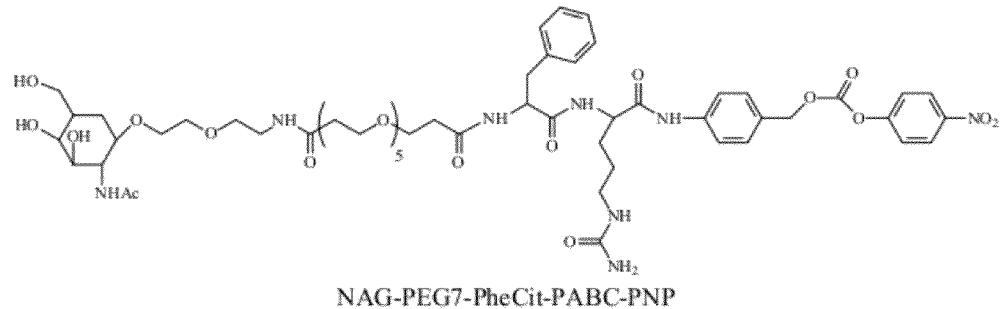
Figure 3:
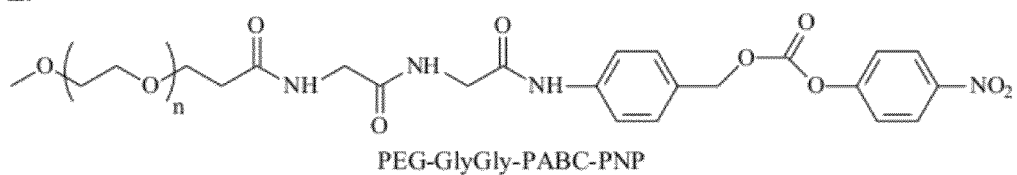
Figure 3:
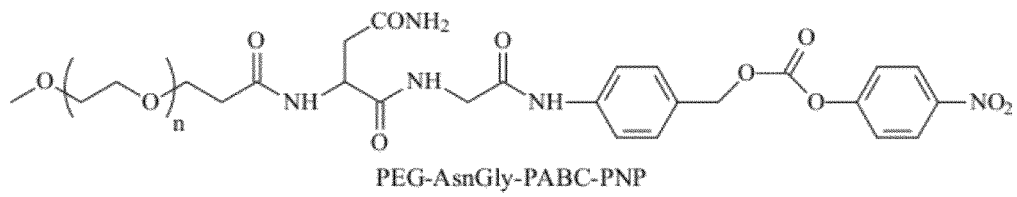
Figure 3:
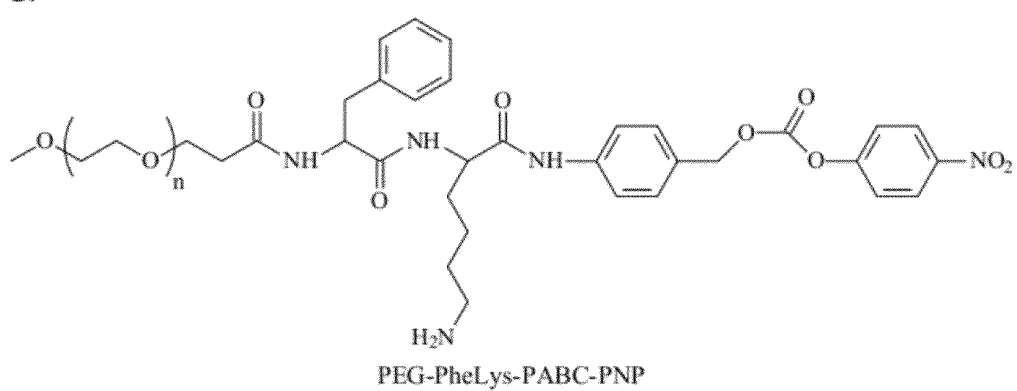
Figure 3:
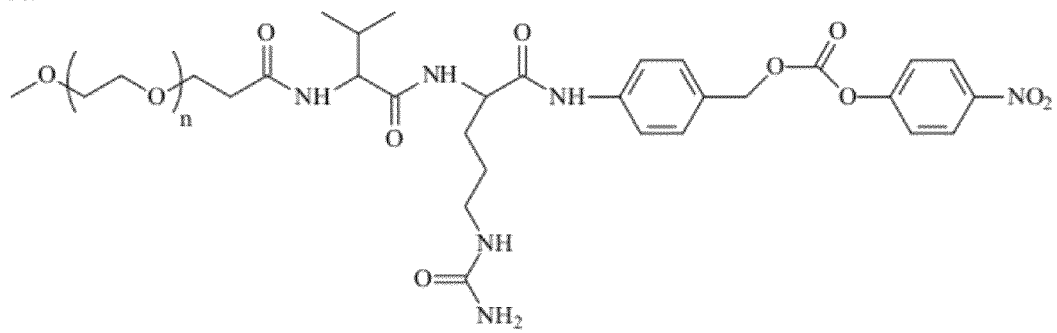
Figure 3:
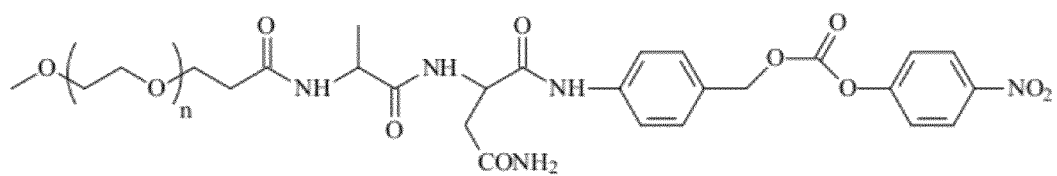
Figure 3:
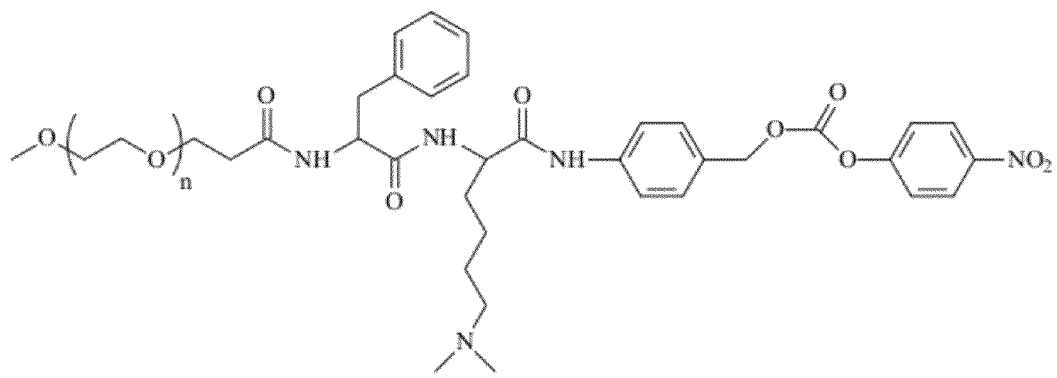

Described are masking agents useful for reversibly modification and inhibition of amphipathic membrane active polyamines and the delivery polymers formed by modification of the polyamine by the dipeptide masking agents. The peptidase cleavable linkages are stable to hydrolysis in absence of enzyme, electrically neutral and provide extended DPC stability in storage and in in vivo circulation. Improved (longer) half-life in circulation facilitates widening of the window of opportunity for ligand-mediated accumulation in tissue, such as tumor tissue. The delivery polymers are particularly useful for in vivo delivery of RNAi polynucleotides. In vivo delivery of RNAi polynucleotides is useful for therapeutic inhibition (knockdown) of gene expression.

The dipeptide masking agents have the general form:

R-A$^1$A$^2$-amidobenzyl-carbonate.

wherein R is a steric stabilizer or targeting ligand, A$^1$ is an amino acid, A$^2$ is an amino acid, and carbonate is an activated amine-reactive carbonate. R is preferably uncharged. Reaction of the masking agent carbonate with a polymer amine yields a carbamate linkage. The masking agent is stable until the dipeptide is cleaved in vivo by an endogenous protease, thus cleaving the steric stabilizer or targeting ligand from the polyamine. Following enzymatic cleavage after the dipeptide (between A$^2$ and the amidobenzyl), the amidobenzyl-carbamate undergoes a spontaneous rearrangement which results in regeneration of the polymer amine. A preferred steric stabilizer is a polyethylene glycol (PEG). A preferred targeting ligand for liver delivery is an ASGPr ligand. A preferred ASGPr ligand is an N-Acetylgalactosamine (NAG). A preferred amidobenzyl group is a p-amidobenzyl group.

Dipeptides of the dipeptide masking agents, represented as $A^1A^2$ (or AA), are dimers of amino acids connected via amide bonds. Amino acids, including α and β amino acids are well known in biology and chemistry and are molecules containing an amine group, a carboxylic acid group and a side-chain that varies between different amino acids. A preferred amino acid is an α-amino acid having the generic formula $H_2NCHRCOOH$, where R is an organic substituent. A preferred α amino acid is an uncharged naturally occurring amino acid. In a preferred dipeptide, A1 is a hydrophobic amino acid and A2 is an uncharged hydrophilic amino acid. A preferred hydrophobic amino acid is phenylalanine, valine, isoleucine, leucine, alanine, or tryptophan. A preferred uncharged hydrophilic amino acid is asparagine, glutamine, or citrulline. A more preferred hydrophobic amino acid is phenylalanine or valine. A more preferred uncharged hydrophilic amino acid is citrulline. While dipeptides are preferred, it is possible to insert additional amino acids between $A^1$ and R. It is also possible to use a single amino acid instead of a dipeptide by eliminating amino acid $A^1$. Any natural amino acids used in the present invention are referred to herein by their common abbreviations. While charged amino acids can be used, it is preferred that the masking agent be uncharged.

In a preferred embodiment, an amphipathic membrane active polyamine is reversibly modified by reaction with a dipeptide-amidobenzyl-carbonate masking agent of the invention to yield a membrane inactive delivery polymer. The dipeptide masking agents can shield the polymer from non-specific interactions, increase circulation time, enhance specific interactions, inhibit toxicity, or alter the charge of the polymer.

Reversibly masked polymers of the invention comprise the structure:

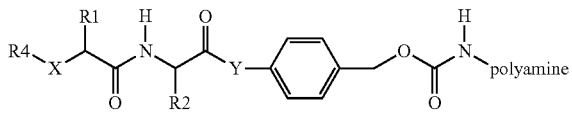

wherein:
X is —NH—, —O—, or —CH$_2$—
Y is —NH— or —O—
R1 is preferably
—(CH$_2$)$_k$-phenyl (k is 1, 2, 3, 4, 5, 6; k=1 phenylalanine),
—CH—(CH$_3$)$_2$ (valine),
—CH$_2$—CH—(CH$_3$)$_2$ (leucine),
—CH(CH$_3$)—CH$_2$—CH$_3$ (isoleucine),
—CH$_3$ (alanine),
—(CH$_2$)$_2$—COOH (glutamic acid),
or

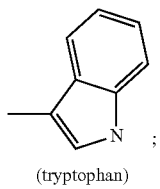
(tryptophan)

R2 is preferably
hydrogen (glycine)
—(CH$_2$)$_3$—NH—C(O)—NH$_2$ (citrulline),
—(CH$_2$)$_4$—N—(CH$_3$)$_2$ (lysine(CH$_3$)$_2$),
—(CH$_2$)$_k$—C(O)—NH$_2$; (k is 1, 2, 3, 4, 5, 6),
—CH$_2$—C(O)—NH$_2$ (asparagine),
—(CH$_2$)$_2$—C(O)—NH$_2$ (glutamine),
—CH$_2$—C(O)—NR$^1$R$^2$ (aspartic acid amide),
—(CH$_2$)$_2$—C(O)—NR$^1$R$^2$ (glutamic acid amide),
—CH$_2$—C(O)—OR$^1$ (aspartic acid ester), or
—(CH$_2$)$_2$—C(O)—OR$^1$ (glutamic acid ester),
R$^1$ and R$^2$ are alkyl groups
R$^4$ comprises a polyethylene glycol or targeting ligand; and the polyamine is an amphipathic membrane active polyamine.

While the structure above indicates a single dipeptide masking agent linked to the polymer, in practice of the invention, 50% to 90% or In a preferred embodiment, X is —NH—, Y is —NH—, $R^4$ is uncharged, $R^5$ is at position 4, and $R^6$ is hydrogen as shown by:

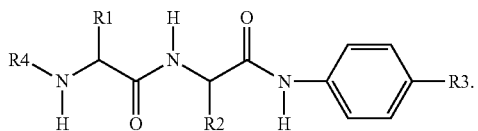

In another embodiment, $R^4$ is:

R—(O—$CH_2$—$CH_2$)$_s$—O—Y1—, wherein

R is hydrogen, methyl, or ethyl; and s is= an integer from 1 to 150, and Y1 is a linker selected from the list comprising:

—O—Y2—NH—C(O)—$(CH_2)_2$—C(O)—, wherein Y2 is

—$(CH_2)_3$

—C(O)—N—($CH_2$—$CH_2$—O)$_p$—$CH_2$—$CH_2$—(p is an integer from 1 to 20), and

—O—.

A targeting ligand may be selected from the list comprising hapten, vitamin, antibody, monoclonal antibody, and cell surface receptor ligand. A targeting ligand may be linked to the dipeptide via a linker such as a PEG linker.

Non-limiting examples of membrane active polymers suitable for use with the invention have been previously described in US Patent Publications 20080152661, 20090023890, 20080287630, and 20110207799. Suitable amphipathic membrane active polyamine can also be small peptides such as a melittin peptide.

Polymer amines were reversibly modified using the enzyme cleavable linkers described herein. An amine is reversibly modified if cleavage of the modifying group results in regeneration of the amine. Reaction of the activated carbonate of the masking agent with a polymer amine connects a targeting ligand or steric stabilizer to the polymer via a peptidase cleavable dipeptide-amidobenzyl carbamate linkage as shown:

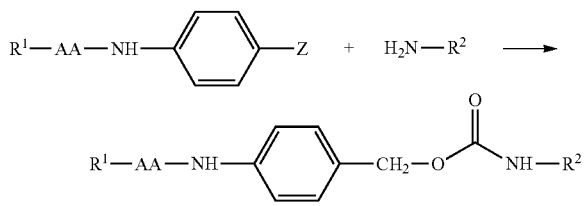

$R^1$ comprises an targeting ligand (either with or without protecting groups) or a PEG, $R^2$ is an amphipathic membrane active polyamine, AA is a dipeptide (either with or without protecting groups), and Z is an amine-reactive carbonate.

Protecting groups may be used during synthesis of the dipeptide masking agents. If present, protecting groups may be removed prior to or after modification of the amphipathic membrane active polyamine.

Reversible modification of a sufficient percentage of the polymer amines with the dipeptide masking agents inhibits membrane activity of the membrane active polyamine. Modification of polymer amines with the dipeptide masking agents also preferably neutralizes charge of the amine. The dipeptide-amidobenzyl-carbamate linkage is susceptible to protease (or peptidase) cleavage. In presence of protease, the anilide bond is cleaved, resulting in an intermediate which immediately undergoes a 1,6 elimination reaction to release free polymer:

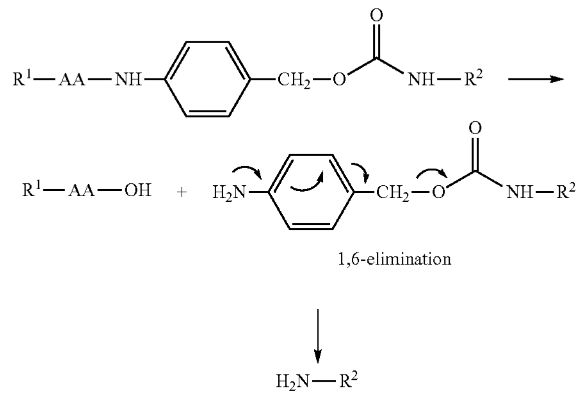

In the above reaction scheme, AA is a dipeptide, $R^1$ comprises a targeting ligand or a steric stabilizer, and $R^2$ is an amphipathic membrane active polyamine. Importantly, the free polymer is unmodified and so membrane activity it restored.

In the masked state, the reversibly masked membrane active polyamine does not exhibit membrane disruptive activity. Reversible modification of more than 50%, more than 55%, more than 60%, more than 65%, more than 70%, more than 75%, more than 80%, or more than 90% of the amines on the polyamine with dipeptide masking agents may be required to inhibit membrane activity and provide cell targeting function, i.e. form a reversibly masked membrane active polymer (delivery polymer).

The present invention also provides a method for delivery of a biologically active substance, into cells. More specifically, the present invention is directed to compounds, compositions, and methods useful for delivering RNAi polynucleotides mammalian cells in vivo.

In one embodiment, the RNAi polynucleotide is linked to the delivery polymer of the invention via a physiologically labile covalent linkage. By using a physiologically labile linkage, the polynucleotide can be cleaved from the polymer, releasing the polynucleotide to engage in functional interactions with cell components.

The invention includes conjugate delivery systems of the general structure:

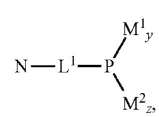

wherein N is a RNAi polynucleotide, $L^1$ is a physiologically labile linkage, P is an amphipathic membrane active polyamine, $M^1$ is an targeting ligand linked to P via a dipeptide-amidobenzyl-carbamate linkage, and $M^2$ is a steric stabilizer linked to P via a dipeptide-amidobenzyl-carbamate linkage. y and z are each integers greater than or equal to zero provided y+z has a value greater than 50%, greater than 60%, greater than 70%, greater than 80% or greater than 90% of the primary amines on polyamine P, as determined by the quantity of amines on P in the absence of any masking agents. In its unmodified state, P is a membrane active polyamine. Delivery polymer $M^1_y$-P-$M^2_z$ is not membrane active. Reversible modification of P primary amines, by attachment of $M^1$ and/or $M^2$, reversibly inhibits or inactivates membrane activity of P. It is noted that some small amphipathic membrane active polyamine, such as melittin peptide, contain as few as 3-5 primary amines. Modification of a percentage of amines is meant to reflect the modification of a percentage of amines in a population of polymers. Upon cleavage of $M^1$ and $M^2$, amines of the polyamine are regenerated thereby reverting P to its unmodified, membrane active state.

In another embodiment, the RNAi polynucleotide is co-administered in vivo with a delivery polymer of the invention. Thus, the invention includes compositions of the general structure:

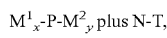

$M^1_x$-P-$M^2_y$ plus N-T, wherein N is a RNAi polynucleotide, T is a targeting group, P is an amphipathic membrane active polyamine, $M^1$ is a targeting ligand linked to P via a dipeptide-amidobenzyl-carbamate linkage, and $M^2$ is a steric stabilizer linked to P via a dipeptide-amidobenzyl-carbamate linkage. y and z are each integers greater than or equal to zero provided y+z has a value greater than 50%, greater than 60%, greater than 70%, greater than 80% or greater than 90% of the primary amines on polyamine P, as determined by the quantity of amines on P in the absence of any masking agents. In its unmodified state, P is a membrane active polyamine.

Delivery polymer $M^1_y$-P-$M^2_z$ is not membrane active. Reversible modification of P primary amines, by attachment of $M^1$ and/or $M^2$, reversibly inhibits or inactivates membrane activity of P. It is noted that some small amphipathic membrane active polyamine, such as melittin peptide, contain as few as 3-5 primary amines. Therefore, modification of a percentage of amines is meant to reflect the modification of a percentage of amines in a population of polymers. Upon cleavage of $M^1$ and $M^2$, amines of the polyamine are regenerated thereby reverting P to its unmodified, membrane active state. N is linked to T via a covalent bond to form a RNAi polynucleotide-targeting group conjugate using methods standard in the art. A preferred covalent bond is a physiologically labile bond. N-T. The delivery polymer and N-T are synthesized or manufactured separately. Neither T nor N are covalently linked directly or indirectly to P, $M^1$ or $M^2$. Electrostatic or hydrophobic association of the polynucleotide or the polynucleotide-conjugate with the masked or unmasked polymer is not required for in vivo liver delivery of the polynucleotide. The masked polymer and the polynucleotide conjugate can be supplied in the same container or in separate containers. They may be combined prior to administration, co-administered, or administered sequentially.

For hepatocyte delivery, whether the RNAi polynucleotide is linked to the delivery polymer via a covalent bond or co-administered with the delivery polymer, y has a value greater than 50% and up to 100% of the primary amines on polymer P. z therefore has a value greater or equal to zero percent (0%) but less than 50% of the primary amines on polymer P.

For delivery to liver tumor cells, z may have a value up to 100% of the primary amines on polymer P. In a preferred embodiment, for delivery to tumor cells, z has a value greater than 50%, greater than 60%, greater than 70%, greater than 80% or greater than 90% of the primary amines on polyamine P and y is zero.

Membrane active polyamines are capable of disrupting plasma membranes or lysosomal/endocytic membranes. This membrane activity is an essential feature for cellular delivery of the polynucleotide. Membrane activity, however, leads to toxicity when the polymer is administered in vivo. Polyamines also interact readily with many anionic components in vivo, leading to undesired bio-distribution. Therefore, reversible masking of membrane activity of the polyamine is necessary for in vivo use.

Masking is accomplished through reversible attachment of the described dipeptide masking agents to the membrane active polyamine to form a reversibly masked membrane active polymer, i.e. a delivery polymer. In addition to inhibiting membrane activity, the masking agents shield the polymer from non-specific interactions, reduce serum interactions, neutralize the polyamine to reduce positive charge and form a near neutral charge polymer, increase circulation time, and/or provide cell-specific interactions, i.e. targeting.

It is an essential feature of the masking agents that, in aggregate, they inhibit membrane activity of the polymer. Masking agents may shield the polymer from non-specific interactions (reduce serum interactions, increase circulation time). The membrane active polyamine is membrane active in the unmodified (unmasked) state and not membrane active (inactivated) in the modified (masked) state. A sufficient number of masking agents are linked to the polymer to achieve the desired level of inactivation. The desired level of modification of a polymer by attachment of masking agent(s) is readily determined using appropriate polymer activity assays. For example, if the polymer possesses membrane activity in a given assay, a sufficient level of masking agent is linked to the polymer to achieve the desired level of inhibition of membrane activity in that assay. Masking requires modification of $\geq 50\%$, $\geq 60\%$, $\geq 70\%$, $\geq 80\%$ or $\geq 90\%$ of the primary amine groups on a population of polymer, as determined by the quantity of primary amines on the polymer in the absence of any masking agents. It is also a preferred characteristic of masking agents that their attachment to the polymer reduces positive charge of the polymer, thus forming a more neutral delivery polymer. It is desirable that the masked polymer retain aqueous solubility.

The membrane active polyamine can be conjugated to masking agents in the presence of an excess of masking agents. The excess masking agent may be removed from the conjugated delivery polymer prior to administration of the delivery polymer.

As used herein, a "steric stabilizer" is a non-ionic hydrophilic polymer (either natural, synthetic, or non-natural) that prevents or inhibits intramolecular or intermolecular interactions of a polymer to which it is attached relative to the polymer containing no steric stabilizer. A steric stabilizer hinders a polymer to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a polymer. A preferred steric stabilizer is a polyethylene glycol (PEG) or PEG derivative. As used herein, a preferred PEG can have about 1-500 ethylene glycol monomers, or 2-25. As used herein, a preferred PEG can also have a molecular weight average of about 85-20,000 Daltons (Da), about 85-1000 Da. As used herein, steric stabilizers prevent or inhibit intramolecular or intermolecular interactions of a polymer to which it is attached relative to the polymer containing no steric stabilizer in aqueous solution.

"Targeting ligands" enhance the pharmacokinetic or biodistribution properties of a conjugate to which they are attached to improve cell- or tissue-specific distribution and cell-specific uptake of the conjugate. As used herein, for clarity, the term 'targeting ligand' is used to denote a targeting ligand that is attached to a dipeptide masking agent, and 'targeting group' is a targeting ligand that is linked to an RNAi polynucleotide in an RNAi polynucleotide-targeting group conjugate. Targeting ligands enhance the association of molecules with a target cell. Thus, targeting ligands can enhance the pharmacokinetic or biodistribution properties of a conjugate to which they are attached to improve cellular distribution and cellular uptake of the conjugate. Binding of a targeting ligand to a cell or cell receptor may initiate endocytosis. Targeting ligands may be monovalent, divalent, trivalent, tetravalent, or have higher valency. Targeting ligands may be selected from the group comprising: compounds with affinity to cell surface molecule, cell receptor ligands, antibodies, monoclonal antibodies, antibody fragments, and antibody mimics with affinity to cell surface molecules. A preferred targeting ligand comprises a cell receptor ligand. A variety of ligands have been used to target drugs and genes to cells and to specific cellular receptors. Cell receptor ligands may be selected from the group comprising: carbohydrates, glycans, saccharides (including, but not limited to: galactose, galactose derivatives, mannose, and mannose derivatives), vitamins, folate, biotin, aptamers, and peptides (including, but not limited to: RGD-containing peptides, insulin, EGF, and transferrin).

For liver hepatocyte targeting, a preferred targeting ligand is a saccharide having affinity for the asialoglycoprotein receptor (ASGPr). Galactose and galactose derivates have been used to target molecules to hepatocytes in vivo through their binding to the ASGPr expressed on the surface of hepatocytes. As used herein, a "ASGPr targeting ligand" comprises a galactose and galactose derivative having affinity for the ASGPr equal to or greater than that of galactose. Binding of galactose targeting ligand to the ASGPr(s) facilitates cell-specific targeting of the delivery polymer to hepatocytes and endocytosis of the delivery polymer into hepatocytes.

ASGPr targeting ligands may be selected from the group comprising: lactose, galactose, N-acetylgalactosamine (NAG), galactosamine, N-formylgalactosamine, N-acetylgalactosamine, N-propionylgalactosamine, N-n-butanoylgalactosamine, and N-iso-butanoyl-galactosamine (Iobst, S. T. and Drickamer, K. J.B.C. 1996, 271, 6686). ASGPr targeting moieties can be monomeric (e.g., having a single galactosamine) or multimeric (e.g., having multiple galactosamines).

In one embodiment, the membrane active polyamine is reversibly masked by attachment of ASGPr targeting ligand masking agents to $\geq$50%, $\geq$60%, $\geq$70%, $\geq$80%, or $\geq$90% of primary amines on the polyamine. In another embodiment, the membrane active polyamine is reversibly masked by attachment of ASGPr targeting ligand masking agents and PEG masking agents to $\geq$50%, $\geq$60%, $\geq$70%, $\geq$80%, or $\geq$90% of primary amines on the polymer. When both ASGPr targeting ligand masking agents and PEG masking agents, a ratio of PEG to ASGPr targeting ligand is about 0-4:1, more preferably about 0.5-2:1.

"Amphipathic", or amphiphilic, polymers are well known and recognized in the art and have both hydrophilic (polar, water-soluble) and hydrophobic (non-polar, lipophilic, water-insoluble) groups or parts.

"Hydrophilic groups" indicate in qualitative terms that the chemical moiety is water-preferring. Typically, such chemical groups are water soluble, and are hydrogen bond donors or acceptors with water. A hydrophilic group can be charged or uncharged. Charged groups can be positively charged (anionic) or negatively charged (cationic) or both (zwitterionic). Examples of hydrophilic groups include the following chemical moieties: carbohydrates, polyoxyethylene, certain peptides, oligonucleotides, amines, amides, alkoxy amides, carboxylic acids, sulfurs, and hydroxyls.

"Hydrophobic groups" indicate in qualitative terms that the chemical moiety is water-avoiding. Typically, such chemical groups are not water soluble, and tend not to form hydrogen bonds. Lipophilic groups dissolve in fats, oils, lipids, and non-polar solvents and have little to no capacity to form hydrogen bonds. Hydrocarbons containing two (2) or more carbon atoms, certain substituted hydrocarbons, cholesterol, and cholesterol derivatives are examples of hydrophobic groups and compounds.

Hydrophobic groups are preferably hydrocarbons, containing only carbon and hydrogen atoms. However, non-polar substitutions or non-polar heteroatoms which maintain hydrophobicity, and include, for example fluorine, may be permitted. The term includes aliphatic groups, aromatic groups, acyl groups, alkyl groups, alkenyl groups, alkynyl groups, aryl groups, aralkyl groups, aralkenyl groups, and aralkynyl groups, each of which may be linear, branched, or cyclic. The term hydrophobic group also includes: sterols, steroids, cholesterol, and steroid and cholesterol derivatives.

As used herein, with respect to amphipathic polymers, a part is defined as a molecule derived when one covalent bond is broken and replaced by hydrogen. For example, in butyl amine, a breakage between the carbon and nitrogen bonds, and replacement with hydrogens, results in ammonia (hydrophilic) and butane (hydrophobic). If 1,4-diaminobutane is cleaved at nitrogen-carbon bonds, and replaced with hydrogens, the resulting molecules are again ammonia (2×) and butane. However, 1,4,-diaminobutane is not considered amphipathic because formation of the hydrophobic part requires breakage of two bonds.

As used herein, a surface active polymer lowers the surface tension of water and/or the interfacial tension with other phases, and, accordingly, is positively adsorbed at the liquid/vapor interface. The property of surface activity is usually due to the fact that the molecules of the substance are amphipathic or amphiphilic.

As used herein, "membrane active" polymers are surface active, amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the polymer's activity in at least one the following assays: red blood cell lysis (hemolysis), liposome leakage, liposome fusion, cell fusion, cell lysis, and endosomal release. Membrane active polymers that can cause lysis of cell membranes are also termed membrane lytic polymers. Polymers that preferentially cause disruption of endosomes or lysosomes over plasma membrane are considered endosomolytic. The effect of membrane active polymers on a cell membrane may be transient. Membrane active possess affinity for the membrane and cause a denaturation or deformation of bilayer structures. Membrane active polymers may be synthetic or non-natural amphipathic polymers.

As used herein, membrane active polymers are distinct from a class of polymers termed cell penetrating peptides or polymers represented by compounds such as the arginine-rich peptide derived from the HIV TAT protein, the antennapedia peptide, VP22 peptide, transportan, arginine-rich artificial peptides, small guanidinium-rich artificial polymers and the like. While cell penetrating compounds appear to transport some molecules across a membrane, from one side of a lipid bilayer to other side of the lipid bilayer, apparently without requiring endocytosis and without disturbing the integrity of the membrane, their mechanism is not understood.

Delivery of a polynucleotide to a cell is mediated by the membrane active polymer disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm.

Amphipathic membrane active polyamine copolymers of the invention are the product of copolymerization of two or more monomer species. In one embodiment, amphipathic membrane active heteropolymers of the invention have the general structure:

-(A)$_a$-(B)$_b$- wherein, A contains a pendent primary or secondary amine functional group and B contains a pendent hydrophobic group. a and b are integers >0. The polymers may be random, block, or alternating. The incorporation of additional monomers is permissible.

"Endosomolytic polymers" are polymers that, in response to an endosomal-specific environmental factors, such as the presence of lytic enzymes, are able to cause disruption or lysis of an endosome or provide for release of a normally cell membrane impermeable compound, such as a polynucleotide, from a cellular internal membrane-enclosed vesicle, such as an endosome or lysosome. Endosomolytic polymers undergo a shift in their physico-chemical properties in the endosome. This shift can be a change in the polymer's solubility or ability to interact with other compounds or membranes as a result in a shift in charge, hydrophobicity, or hydrophilicity. A reversibly masked membrane active polymamine of the invention are considered to be endosomolytic polymers.

"Melittin" is a small amphipathic membrane active peptide which naturally occurs in bee venom. Melittin can be isolated from a biological source or it can be synthetic. A synthetic polymer is formulated or manufactured by a chemical process "by man" and is not created by a naturally occurring biological process. As used herein, melittin encompasses the naturally occurring bee venom peptides of the melittin family that can be found in, for example, venom of the species: *Apis mellifera, Apis cerana, Vespula maculifrons, Vespa magnifica, Vespa velutina nigrithorax, Polistes* sp. HQL-2001, *Apis florae, Apis dorsata, Apis cerana cerana, Polistes hebraeus*. As used herein, melittin also encompasses synthetic peptides having amino acid sequence identical to or similar to naturally occurring melittin peptides. Specifically, melittin amino acid sequence encompass those shown in Table 1. Synthetic melittin peptides can contain naturally occurring L form amino acids or the enantiomeric D form amino acids (inverso). However, a melittin peptide should either contain essentially all L form or all D form amino acids but may have amino acids of the opposite stereocenter appended at either the amino or carboxy termini. The melittin amino acid sequence can also be reversed (reverso). Reverso melittin can have L form amino acids or D form amino acids (retroinverso). Two melittin peptides can also be covalently linked to form a melittin dimer. Melittin can have modifying groups, other than masking agents, that enhance tissue targeting or facilitate in vivo circulation attached to either the amino terminal or carboxy terminal ends.

A linkage or "linker" is a connection between two atoms that links one chemical group or segment of interest to another chemical group or segment of interest via one or more covalent bonds. For example, a linkage can connect a masking agent or polynucleotide to a polymer. A labile linkage contains a labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides. Spacer groups are well known in the art and the preceding list is not meant to limit the scope of the invention.

A "labile bond" is a covalent bond other than a covalent bond to a hydrogen atom that is capable of being selectively broken or cleaved under conditions that will not break or cleave other covalent bonds in the same molecule. More specifically, a labile bond is a covalent bond that is less stable (thermodynamically) or more rapidly broken (kinetically) under appropriate conditions than other non-labile covalent bonds in the same molecule. Cleavage of a labile bond within a molecule may result in the formation of two molecules. For those skilled in the art, cleavage or lability of a bond is generally discussed in terms of half-life ($t_{1/2}$) of bond cleavage (the time required for half of the bonds to cleave). Thus, labile bonds encompass bonds that can be selectively cleaved more rapidly than other bonds a molecule.

As used herein, a "physiologically labile bond" is a labile bond that is cleavable under conditions normally encountered or analogous to those encountered within a mammalian body. Physiologically labile linkage groups are selected such that they undergo a chemical transformation (e.g., cleavage) when present in certain physiological conditions.

As used herein, a cellular physiologically labile bond is a labile bond that is cleavable under mammalian intracellular conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. A cellular physiologically labile bond may also be cleaved in response to administration of a pharmaceutically acceptable exogenous agent.

RNAi interference-targeting group conjugate: A targeting group may be linked to the 3' or the 5' end of the RNAi polynucleotide. For siRNA polynucleotides, the targeting moiety may be linked to either the sense strand or the antisense strand, though the sense strand is preferred.

In one embodiment, the targeting group consists of a hydrophobic group More specifically, the targeting group consists of a hydrophobic group having at least 20 carbon atoms. Hydrophobic groups used as polynucleotide targeting moieties are herein referred to as hydrophobic targeting moieties. Exemplary suitable hydrophobic groups may be selected from the group comprising: cholesterol, dicholesterol, tocopherol, ditocopherol, didecyl, didodecyl, dioctadecyl, didodecyl, dioctadecyl, isoprenoid, and choleamide. Hydrophobic groups having 6 or fewer carbon atoms are not effective as polynucleotide targeting moieties, while hydrophobic groups having 8 to 18 carbon atoms provide increasing polynucleotide delivery with increasing size of the hydrophobic group (i.e. increasing number of carbon atoms). Attachment of a hydrophobic targeting group to an RNAi polynucleotide does not provide efficient functional in vivo delivery of the RNAi polynucleotide in the absence of co-administration of the delivery polymer. While siRNA-cholesterol conjugates have been reported by others to deliver siRNA (siRNA-cholesterol) to liver cells in vivo, in the absence of any additional delivery vehicle, high concentrations of siRNA are required and delivery efficacy is poor. When combined with the delivery polymers described herein, delivery of the polynucleotide is greatly improved. By providing the siRNA-cholesterol together with a delivery polymer of the invention, efficacy of siRNA-cholesterol is increased about 100 fold.

Hydrophobic groups useful as polynucleotide targeting moieties may be selected from the group consisting of: alkyl group, alkenyl group, alkynyl group, aryl group, aralkyl group, aralkenyl group, and aralkynyl group, each of which may be linear, branched, or cyclic, cholesterol, cholesterol derivative, sterol, steroid, and steroid derivative. Hydrophobic targeting groups are preferably hydrocarbons, containing only carbon and hydrogen atoms. However, substitutions or heteroatoms which maintain hydrophobicity, for example fluorine, may be permitted. The hydrophobic targeting group may be attached to the 3' or 5' end of the RNAi polynucleotide using methods known in the art. For RNAi polynucleotides having 2 strands, such as siRNA, the hydrophobic group may be attached to either strand.

In another embodiment, the targeting group comprises a galactose cluster (galactose cluster targeting moiety). As used herein, a "galactose cluster" comprises a molecule having two to four terminal galactose derivatives. As used herein, the term galactose derivative includes both galactose and derivatives of galactose having affinity for the ASGPr equal to or greater than that of galactose. A terminal galactose derivative is attached to a molecule through its C-1 carbon. A preferred galactose cluster has three terminal galactosamines or galactosamine derivatives each having affinity for the asialoglycoprotein receptor. A more preferred galactose cluster has three terminal N-acetylgalactosamines. Other terms common in the art include tri-antennary galactose, tri-valent galactose and galactose trimer. It is known that tri-antennary galactose derivative clusters bind to the ASGPr with greater affinity than bi-antennary or mono-antennary galactose derivative structures (Baenziger and Fiete, 1980, Cell, 22, 611-620; Connolly et al., 1982, J. Biol. Chem., 257, 939-945). Multivalency is required to achieve nM affinity. The attachment of a single galactose derivative having affinity for the asialoglycoprotein receptor does not enable functional delivery of the RNAi polynucleotide to hepatocytes in vivo when co-administered with the delivery polymer.

A galactose cluster contains two-four, preferably three, galactose derivatives each linked to a central branch point. The galactose derivatives are attached to the central branch point through the C-1 carbons of the saccharides. The galactose derivative is preferably linked to the branch point via linkers or spacers. A preferred spacer is a flexible hydrophilic spacer (U.S. Pat. No. 5,885,968; Biessen et al. J. Med. Chem. 1995 Vol. 39 p. 1538-1546). A preferred flexible hydrophilic spacer is a PEG spacer. A preferred PEG spacer is a $PEG_3$ spacer. The branch point can be any small molecule which permits attachment of the three galactose derivatives and further permits attachment of the branch point to the RNAi polynucleotide. An exemplary branch point group is a di-lysine. A di-lysine molecule contains three amine groups through which three galactose derivatives may be attached and a carboxyl reactive group through which the di-lysine may be attached to the RNAi polynucleotide. Attachment of the branch point to the RNAi polynucleotide may occur through a linker or spacer. A preferred spacer is a flexible hydrophilic spacer. A preferred flexible hydrophilic spacer is a PEG spacer. A preferred PEG spacer is a $PEG_3$ spacer (three ethylene units). The galactose cluster may be attached to the 3' or 5' end of the RNAi polynucleotide using methods known in the art. For RNAi polynucleotides having 2 strands, such as siRNA, the galactose cluster may be attached to either strand. Suitable galactose clusters are described in US Patent Publication 20110207799.

The term "polynucleotide", or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. A polynucleotide may contain ribonucleotides, deoxyribonucleotides, synthetic nucleotides, or any suitable combination. Polynucleotides may be polymerized in vitro, they may be recombinant, contain chimeric sequences, or derivatives of these groups. A polynucleotide may include a terminal cap moiety at the 5'-end, the 3'-end, or both the 5' and 3' ends. The cap moiety can be, but is not limited to, an inverted deoxy abasic moiety, an inverted deoxy thymidine moiety, a thymidine moiety, or 3' glyceryl modification.

An "RNA interference (RNAi) polynucleotide" is a molecule capable of inducing RNA interference through interaction with the RNA interference pathway machinery of mammalian cells to degrade or inhibit translation of messenger RNA (mRNA) transcripts of a transgene in a sequence specific manner. Two primary RNAi polynucleotides are small (or short) interfering RNAs (siRNAs) and micro RNAs (miRNAs). RNAi polynucleotides may be selected from the group comprising: siRNA, microRNA, double-strand RNA (dsRNA), short hairpin RNA (shRNA), and expression cassettes encoding RNA capable of inducing RNA interference. siRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may have dinucleotide 3' overhangs. An siRNA may be composed of two annealed polynucleotides or a single polynucleotide that forms a hairpin structure. An siRNA molecule of the invention comprises a sense region and an antisense region. In one embodiment, the siRNA of the conjugate is assembled from two oligonucleotide fragments wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker. MicroRNAs (miRNAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

RNAi polynucleotide expression cassettes can be transcribed in the cell to produce small hairpin RNAs that can function as siRNA, separate sense and anti-sense strand linear siRNAs, or miRNA. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters.

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The polynucleotides of the invention can be chemically modified. Non-limiting examples of such chemical modifications include: phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various polynucleotide constructs, are shown to preserve polynucleotide activity in cells while at the same time increasing the serum stability of these compounds. Chemically modified siRNA can also minimize the possibility of activating interferon activity in humans.

In one embodiment, a chemically-modified RNAi polynucleotide of the invention comprises a duplex having two strands, one or both of which can be chemically-modified, wherein each strand is about 19 to about 29 nucleotides. In one embodiment, an RNAi polynucleotide of the invention comprises one or more modified nucleotides while maintaining the ability to mediate RNAi inside a cell or reconstituted in vitro system. An RNAi polynucleotide can be modified wherein the chemical modification comprises one or more (e.g., about 1, 2, 3, 4, 5, 6, 7, 8, 9, 10, or more) of the nucleotides. An RNAi polynucleotide of the invention can comprise modified nucleotides as a percentage of the total number of nucleotides present in the RNAi polynucleotide. As such, an RNAi polynucleotide of the invention can generally comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given RNAi polynucleotide depends on the total number of nucleotides present in the RNAi polynucleotide. If the RNAi polynucleotide is single stranded, the percent modification can be based upon the total number of nucleotides present in the single stranded RNAi polynucleotide. Likewise, if the RNAi polynucleotide is double stranded, the percent modification can be based upon the total number of nucleotides present in the sense strand, antisense strand, or both the sense and antisense strands. In addition, the actual percentage of modified nucleotides present in a given RNAi polynucleotide can also depend on the total number of purine and pyrimidine nucleotides present in the RNAi polynucleotide. For example, wherein all pyrimidine nucleotides and/or all purine nucleotides present in the RNAi polynucleotide are modified.

An RNAi polynucleotide modulates expression of RNA encoded by a gene. Because multiple genes can share some degree of sequence homology with each other, an RNAi polynucleotide can be designed to target a class of genes with sufficient sequence homology. Thus, an RNAi polynucleotide can contain a sequence that has complementarity to sequences that are shared amongst different gene targets or are unique for a specific gene target. Therefore, the RNAi polynucleotide can be designed to target conserved regions of an RNA sequence having homology between several genes thereby targeting several genes in a gene family (e.g., different gene isoforms, splice variants, mutant genes, etc.). In another embodiment, the RNAi polynucleotide can be designed to target a sequence that is unique to a specific RNA sequence of a single gene.

The term "complementarity" refers to the ability of a polynucleotide to form hydrogen bond(s) with another polynucleotide sequence by either traditional Watson-Crick or other non-traditional types. In reference to the polynucleotide molecules of the present invention, the binding free energy for a polynucleotide molecule with its target (effector binding site) or complementary sequence is sufficient to allow the relevant function of the polynucleotide to proceed, e.g., enzymatic mRNA cleavage or translation inhibition. Determination of binding free energies for nucleic acid molecules is well known in the art (Frier et al. 1986, Turner et al. 1987). A percent complementarity indicates the percentage of bases, in a contiguous strand, in a first polynucleotide molecule which can form hydrogen bonds (e.g., Watson-Crick base pairing) with a second polynucleotide sequence (e.g., 5, 6, 7, 8, 9, 10 out of 10 being 50%, 60%, 70%, 80%, 90%, and 100% complementary). Perfectly complementary means that all the bases in a contiguous strand of a polynucleotide sequence will hydrogen bond with the same number of contiguous bases in a second polynucleotide sequence.

By inhibit, down-regulate, or knockdown gene expression, it is meant that the expression of the gene, as measured by the level of RNA transcribed from the gene or the level of polypeptide, protein or protein subunit translated from the RNA, is reduced below that observed in the absence of the blocking polynucleotide-conjugates of the invention. Inhibition, down-regulation, or knockdown of gene expression, with a polynucleotide delivered by the compositions of the invention, is preferably below that level observed in the presence of a control inactive nucleic acid, a nucleic acid with scrambled sequence or with inactivating mismatches, or in absence of conjugation of the polynucleotide to the masked polymer.

It was found that siRNA stabilization against degradation by endosomal/lysosomal-localized nucleases such as DNAse II strongly improves target knock down. Such stabilization may directly affect the amount of siRNA released into the cytoplasm where the cellular RNAi machinery is located. Only the siRNA portion available in the cytoplasm will trigger the RNAi effect.

In addition to poor pharmacokinetic characteristics, siRNAs are susceptible to nucleases in the biological environment when administered as such into the circulation without a protecting delivery vehicle. Accordingly, many siRNAs are rapidly degraded either extracellularly in the tissue and blood stream or after intracellular uptake (endosome). Nuclease cleavage can be inhibited by nucleotides lacking a 2'-OH group such as 2'-deoxy, 2'-O-methyl (2'-OMe) or 2'-deoxy-2'-fluoro (2'-F) nucleotides and by polynucleotides 5'-terminal non-nucleotide moieties, like e.g. cholesterol, aminoalkyl-linker or a phosphothioate at the first internucleotide linkage. Preferably, the RNAi polynucleotide lack any 2'-OH nucleotide within the strand, starting with a 2'-OMe nucleotide at the 5'-end connected by a phosphorothioate (PTO) linkage to the second nucleotide.

siRNAs can be significantly stabilized when using the following design, wherein an oligonucleotide is provided with an antisense strand with the modification pattern: 5'-(w)-(Z1)-(Z2)-(Z3)$n_a$-3' and a sense strand with the modification pattern 5'-(Z3)$n_s$-3', wherein w is independently a 5'-phosphate or 5'-phosphothioate or H, Z1 is independently a 2'-modified nucleoside.

Z2 is independently a 2'-deoxy nucleoside or 2'-Fluoro-modified nucleoside,

Z3 is independently a 2'-modified nucleoside, $n_a$ is 8-23 and $n_s$ is 8-25.

In one preferred embodiment an oligonucleotide is provided with an antisense strand with the modification pattern: 5'-(w)-(Z1)-(Z2)-(Z3)$n_a$-3' and a sense strand with the modification pattern 5'-(Z3)$n_s$-3', wherein Z1 is a 2'-Fluoro-modified nucleoside or a 2-deoxy-nucleoside and all remaining substituents as well as the variables $n_a$ and $n_s$ have the meaning given above.

In one preferred embodiment an oligonucleotide is provided with an antisense strand with the modification pattern: 5'-(w)-(Z1)-(Z2)-(Z3)$n_a$-3' and a sense strand with the modification pattern 5'-(Z3)$n_s$-3', wherein Z3 is a 2'-O-Methyl modified nucleoside, a 2'-Fluoro-modified nucleoside or a 2-deoxy-nucleoside and all remaining substituents as well as the variables $n_a$ and $n_s$ have the meaning given above.

In one preferred embodiment an oligonucleotide is provided with an antisense strand with the modification pattern: 5'-(w)-(Z1)-(Z2)-(Z3)$n_a$-3' and a sense strand with the modification pattern 5'-(Z3)$n_s$-3', wherein Z1 is a a 2'-Fluoro-modified nucleoside or a 2-deoxy-nucleoside and Z3 is a 2'-O-Methyl modified nucleoside, a 2'-Fluoro-modified nucleoside or a 2-deoxy-nucleoside and all remaining substituents as well as the variables $n_a$ and $n_s$ have the meaning given above.

The nucleosides in the nucleic acid sequence of the oligonucleotice with the novel modification pattern can either be linked by 5'-3' phosphodiesters or 5'-3' phosphorothioates.

As used herein, the "anti-sense" strand is the siRNA strand that is complementary to the target mRNA and that will be binding to the mRNA once the siRNA is unwound. The sense strand of said siRNA comprising the novel modification pattern is complimentary to the antisense strand.

In principle a nuclease cleavage site, between the RNAi polynucleotide and the targeting moiety or delivery polymer to which it is covalently attached can be introduced by 3'- or 5'-overhangs containing at least one 2'-OH nucleotide at either the sense or the antisense strand. The final active siRNA species is generated by intracellular nuclease processing. Also, the use of defined cleavage sites implemented by 2'-OH nucleotides within the base paired region is possible. This can be done using at least one 2'-OH nucleotide complementary to the opposite strand or by introduction of either at least one mismatched 2'-OH nucleotide or a hairpin/bulge containing at least one 2'-OH nucleotide.

Linkage of Polynucleotide to Delivery Polymer

In one embodiment, the RNAi polynucleotide is linked to the delivery polymer via a physiologically labile bond or linker. The physiologically labile linker is selected such that it undergoes a chemical transformation (e.g., cleavage) when present in certain physiological conditions, (e.g., disulfide bond cleaved in the reducing environment of the cell cytoplasm). Release of the polynucleotide from the polymer, by cleavage of the physiologically labile linkage, facilitates interaction of the polynucleotide with the appropriate cellular components for activity.

The polynucleotide-polymer conjugate is formed by covalently linking the polynucleotide to the polymer. The polymer is polymerized or modified such that it contains a reactive group A. The polynucleotide is also polymerized or modified such that it contains a reactive group B. Reactive groups A and B are chosen such that they can be linked via a reversible covalent linkage using methods known in the art.

Conjugation of the polynucleotide to the polymer can be performed in the presence of an excess of polymer. Because the polynucleotide and the polymer may be of opposite charge during conjugation, the presence of excess polymer can reduce or eliminate aggregation of the conjugate. Alternatively, an excess of a carrier polymer, such as a polycation, can be used. The excess polymer can be removed from the conjugated polymer prior to administration of the conjugate to the animal or cell culture. Alternatively, the excess polymer can be co-administered with the conjugate to the animal or cell culture.

In Vivo Administration

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the compositions of the invention. The compounds of the present invention can be administered via any suitable route, most preferably parenterally, in a preparation appropriately tailored to that route. Thus, the compounds of the present invention can be administered by injection, for example, intravenously, intramuscularly, intracutaneously, subcutaneously, or intraperitoneally. Accordingly, the present invention also provides pharmaceutical compositions comprising a pharmaceutically acceptable carrier or excipient.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical.

The described compositions are injected in pharmaceutically acceptable carrier solutions. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals and more particularly in humans.

These carrier may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In one embodiment, an RNAi polynucleotide-targeting group conjugate is co-administered with a delivery polymer of the invention. By co-administered it is meant that the RNAi polynucleotide conjugate and the delivery polymer are administered to the mammal such that both are present in the mammal at the same time. The RNAi polynucleotide-targeting group conjugate and the delivery polymer may be administered simultaneously or they may be delivered sequentially. For simultaneous administration, they may be mixed prior to administration. For sequential administration, either the RNAi polynucleotide-targeting moiety conjugate or the delivery polymer may be administered first.

Therapeutic Effect

RNAi polynucleotides may be delivered for research purposes or to produce a change in a cell that is therapeutic. In vivo delivery of RNAi polynucleotides is useful for research reagents and for a variety of therapeutic, diagnostic, target validation, genomic discovery, genetic engineering, and pharmacogenomic applications. We have disclosed RNAi polynucleotide delivery resulting in inhibition of endogenous gene expression in hepatocytes. Levels of a reporter (marker) gene expression measured following delivery of a polynucleotide indicate a reasonable expectation of similar levels of gene expression following delivery of other polynucleotides. Levels of treatment considered beneficial by a person having ordinary skill in the art differ from disease to disease. For example, Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. Similarly, inhibition of a gene need not be 100% to provide a therapeutic benefit. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes serve as useful paradigms for expression of intracellular proteins in general.

The liver is one of the most important target tissues for gene therapy given its central role in metabolism (e.g., lipoprotein metabolism in various hypercholesterolemias) and the secretion of circulating proteins (e.g., clotting factors in hemophilia). In addition, acquired disorders such as chronic hepatitis and cirrhosis are common and are also potentially treated by polynucleotide-based liver therapies. A number of diseases or conditions which affect or are affected by the liver are potentially treated through knockdown (inhibition) of gene expression in the liver. Such liver diseases and conditions may be selected from the list comprising: liver cancers (including hepatocellular carcinoma, HCC), viral infections (including hepatitis), metabolic disorders, (including hyperlipidemia and diabetes), fibrosis, and acute liver injury.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The amount (dose) of delivery polymer, RNAi polynucleotide-targeting group conjugate or delivery polymer-RNAi polynucleotide conjugate that is to be administered can be determined empirically. We have shown effective knockdown of gene expression using 0.1-10 mg/kg animal weight of siRNA and 1.5-60 mg/kg animal weight delivery polymer. A preferred amount in mice is 0.25-2.5 mg/kg siRNA-conjugate and 10-40 mg/kg delivery polymer. More preferably, about 1.5-20 mg/kg delivery polymer is administered. The amount of RNAi polynucleotide-conjugate is easily increased because it is typically not toxic in larger doses.

As used herein, in vivo means that which takes place inside an organism and more specifically to a process performed in or on the living tissue of a whole, living multicellular organism (animal), such as a mammal, as opposed to a partial or dead one.

As used herein, "pharmaceutical composition" includes the conjugates of the invention, a pharmaceutical carrier or diluent and any other media or agent necessary for formulation.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

EXAMPLES

Example 1

Synthesis of Protease (Peptidase) Cleavable Masking Agents

All reactions, except coupling of amino acids in aqueous NaHCO$_3$ and silyl-group deprotection, were carried out in anhydrous conditions using fresh anhydrous solvents. Column purification was done on a silica gel using specified eluents. Mass-spectra (MS) were taken using electrospray ionization.

In preparation of active p-nitrophenyl-p-acylamidobenzyl carbonate derivatives of NAG and PEG (NAG-L-AA-PABC-PNP and PEG-AA-PABC-PNP) we utilized NHS ester of respective PEG or NAG-containing derivatives to acylate amino terminus of dipeptido-p-acylaminobenzy alcohol precursor. In the following steps benzylic hydroxyl group was converted into p-nitrophenyl carbonate followed by removal of protective groups from amino acids and NAG moiety. In some applications, when paranitrophenol (PNP)-carbonates were used for modification of certain polymers, protective groups prior to polymer modification.

of NHS esters, commercially available pentafluorophenyl esters (OPfp) for were used for coupling.

Synthesis of Fmoc Dipeptides 1a-h a) NHS Esters of AA were Prepared from Respective Amino Acids with NHS and DCC and Used without Additional Purification

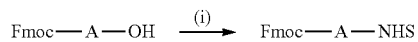

Conditions: (i) N-hydroxysuccinimide (NHS), N—N'-dicyclohexylcarbodiimide (DCC), 0-20° C.

For Fmoc-Ala-NHS, DCC (286 mg, 1.38 mmol) was added to an ice cold solution of Fmoc-Ala-OH (412 mg, 1.32 mmol) and NHS (160 mg, 1.38 mmol) in DCM (13 mL), stirred for 30 min, and then at 20° C. for 16 h. The solid dicyclohexylurea (DCU) was filtered off and the solvent was removed in vacuo.

For Fmoc-Asn(DMCP)-NHS, DCC (148 mg, 0.72 mmol) was added to an ice cold solution of Fmoc-Asn(DMCP)-OH (298 mg, 0.68 mmol) and NHS (83 mg, 0.72 mmol) in DCM (13 mL), stirred for 30 min, and then at 20° C. for 16 h. The solid DCU was filtered off and the solvent was removed in vacuo.

For Fmoc-Gly-NHS, Fmoc-Gly-OH (891 mg, 3 mmol) and NHS (380 mg, 3.3 mmol) were stirred in THF (10 mL) at 0° C. for 5 min and treated with a DCC solution (650 mg, 3.15 mmol) in THF (5 mL). The cooling bath was removed in 30

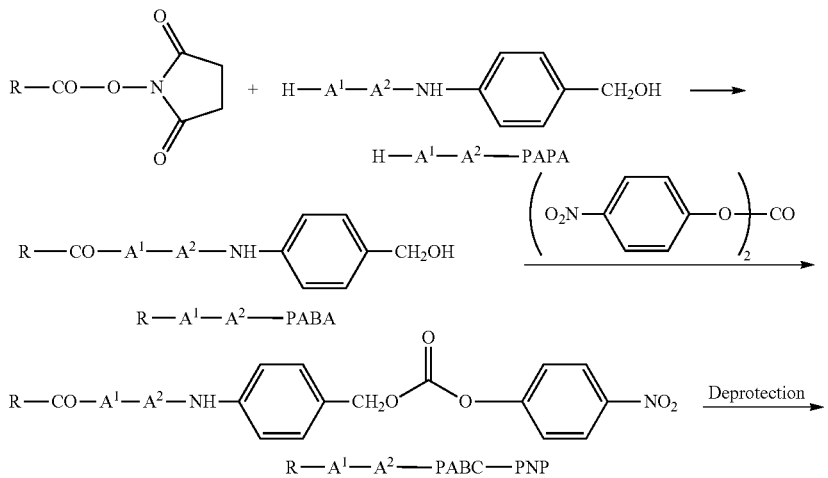

R comprises an ASGPr ligand (protected or unprotected) or a PEG, and

A$^1$ and A$^2$ are amino acids (either protected or unprotected)

The synthesis starts from preparation of H-A$^1$A$^2$-PABA (Table 1) derivatives. These adducts were obtained utilizing synthetic scheme described by Dubowchik at al. (2002) with some modifications. Fmoc-protected amino acids, Fmoc-A$^1$-OH, were activated by conversion into N-hydroxycuccinimide esters, Fmoc-A$^1$-NHS, in reaction with dicyclohexylcarbodiimide (DCC) and N-hydroxycuccinimide (NHS). These reactive NHS-esters were coupled with protected amino acids A$^2$ in presence of aqueous NaHCO$_3$ added to keep amino group reactive. For preparation of 1e and 1f (Table 1), instead min and the reaction mixture was stirred at 20° C. for 10 h. The solid DCU was filtered off, washed with THF and the solvent was removed on the rotovap. The product was weighed and dissolved in DME to make a 0.2 mM solution.

For Fmoc-Glu(O-2PhiPr)-NHS, DCC (217 mg, 1.05 mmol) was added to an ice cold solution of Fmoc-Glu(O-2PhiPr)-OH (487 mg, 1 mmol) and NHS (127 mg, 1.1 mmol) in THF (5 mL), stirred for 15 min and then at 20° C. for 10 h. The workup was done as described for Fmoc-Gly-NHS.

For Fmoc-Phe-NHS, DCC (1.181 g, 5.72 mmol) was added to an ice cold solution of Fmoc-Phe-OH (2.11 g, 5.45 mmol) and NHS (664 mg, 5.77 mmol) in DCM (50 mL), stirred for 30 min, and then at 20° C. for 10 h. The solid DCU was filtered off and the solvent was removed in vacuo.

For Fmoc-Val-NHS, DCC (227 mg, 1.1 mmol) was added to an ice cold solution of Fmoc-Val-OH (339 mg, 1 mmol) and NHS (127 mg, 1.1 mmol) in DCM (13 mL), stirred for 30 min, and then at 20° C. for 16 h. The solid DCU was filtered off and the solvent was removed in vacuo.

b) Amino Acids H-Asn(DMCP)-OH and H-Lys(MMT)-OH were Prepared from Available Fmoc-Protected Derivatives

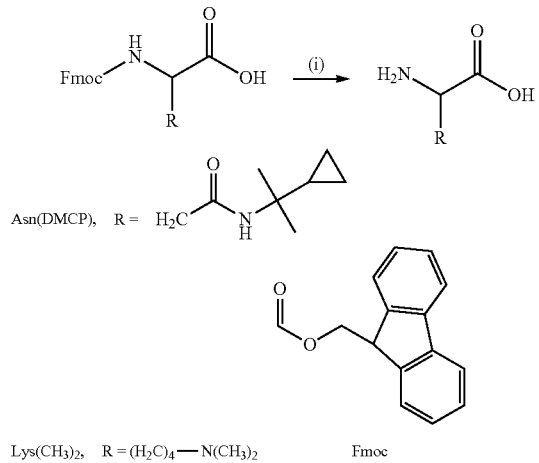

Conditions: (i) Triethylamine ($Et_3N$) in dimethylformamide (DMF).
H-Asn(DMCP)-OH Fmoc-Asn(DMCP)-OH (576 mg, 1.32 mmol) was stirred in DMF (9 mL) with $Et_3N$ (3.7 mL, 26.4 mmol) for 15 h. All volatiles were removed on a rotovap at 40° C./oil pump vacuum. The residue was triturated with ether (30 mL) three times and dried in vacuo. Yield 271 mg (96%). MS: 643.6 $[3M+1]^+$; 451.3 $[2M+Na]^+$; 429.5 $[2M+1]^+$; 236.7 $[M+Na]^+$; 215.3 $[M+1]^+$; 132.8 $[M-DMCP+1]^+$.

H-Lys(MMT)-OH. Fmoc-Lys(MMT)-OH (4.902 g, 7.65 mmol) was stirred in DMF (100 mL) with $Et_3N$ (32 mL, 30 eq. 229.4 mmol) for 10 h. All volatiles were removed on a rotovap at 40° C./oil pump vacuum. The residue was triturated with ether two times and dried in vacuo. Yield 3.1 g (97%). MS (neg. mode): 455, 453.3 $[M+Cl]^-$; 417.8 $[M-1]^-$.

c) Synthesis of Fmoc-$A_1A_2$-OH

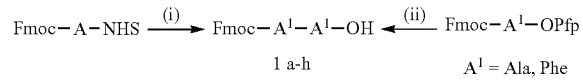

$A^1$=Gly, Glu(2PhiPr), Asn(DMCP), Phe, Ala, Val.
$A^2$=Gly, Lys(MMT), Cit, Asn(DMCP), Lys($CH_3$)$_2$.

Conditions: (i) H-$A_2$-OH, $NaHCO_3$, mixture of dimethoxyethane (DME), tetrahydrofurane (THF) and $H_2O$. (ii) H-$A_2$-OH, $NaHCO_3$, DME/THF/$H_2O$. (iii) H-Cit-OH, $NaHCO_3$, THF in $H_2O$.

For Fmoc-GlyGly-OH 1a, Glycine (75 mg, 1 mmol) and $NaHCO_3$ (100 mg, 1.2 mmol) were dissolved in $H_2O$ (10 mL) and dimethoxyethane (DME) (5 mL). Fmoc-Gly-NHS solution in DME (5 ml, 1 mmol) was added. THF (2.5 mL) was added, the mixture was sonicated to make it homogeneous and stirred for 20 h. All volatiles were removed on a rotovap, the residue was treated with EtOAc and 5% $KHCO_3$ solution in $H_2O$. Product was extracted four times with EtOAc, washed with brine at pH=3, dried ($Na_2SO_4$), concentrated and dried in vacuo. Yield 321 mg (90%). MS: 775.0 $[2M+2Na]^+$; 377.4 $[M+Na]^+$; 355.1 $[M+1]^+$.

For Fmoc-Glu(O-2PhiPr)Gly-OH 1b, Glycine (75 mg, 1 mmol) and $NaHCO_3$ (84 mg, 1 mmol) were dissolved in a mixture of $H_2O$ (2 mL), THF (4 mL) and DME (5 mL). Fmoc-Glu(O-2PhiPr)-NHS solution in DME (5 mL, 1 mmol) was added and stirred for 10 h. All volatiles was removed on a rotovap, 20 mL of 0.1M MES buffer (pH=5) was added followed by EtOAc (25 mL). The reaction mixture was stirred on ice and acidified to pH=5 with 5% solution of $KHSO_4$. Product was extracted four times with EtOAc, rinsed with brine at pH=5, dried ($Na_2SO_4$), concentrated and dried in vacuo. Yield 528 mg (96%). MS: 567 $[M+Na]^+$; 562 $[M+NH_4]^+$; 545.0 $[M+1]^+$; 427.1 $[M-2PhiPr]^+$.

For Fmoc-Asn(DMCP)Gly-OH 1c was prepared from Fmoc-Asn(DMCP)-NHS and H-Gly-OH as described above for 1b. Yield 96%. MS: 987.4 $[2M+1]^+$; 516.3 $[M+Na]^+$; 494.4 $[M+1]^+$; 412.2 $[M-DMCP+1]^+$.

For Fmoc-PheLys(MMT)-OH 1d was prepared from Fmoc-Phe-NHS and H-Lys(MMT)-OH as described above for 1b. Yield 94%. MS: 788.5 $[M+1]^+$, 273.1 $[M-MMT+1]^+$.
For Fmoc-PheCit-OH 1e:
  i) To Fmoc-Phe-NHS (4.96 g, 10.26 mmol) in DME (40 mL) was added to a solution containing L-citrulline (1.80 g, 10.26 mmol) and $NaHCO_3$ (0.86 g, 10.26 mmol) in a mixture of $H_2O$ (40 mL) and THF (20 mL). The reaction was stirred for 15 h. Residual DCC from activation was filtered and the organic solvent was removed on a rotovap. To the residue was added $H_2O$ (100 mL) and iPrOH (10 mL). The suspension was acidified to pH=3 with 5% $KHSO_4$, the product was extracted with an EtOAc:iPrOH=9:1 solution (3×, 500 mL), washed with a mixture of brine:iPrOH=9:1 (2×, 50 mL), dried ($Na_2SO_4$), filtered and concentrated, and dried with oil pump. Trituration with ether afforded the pure product 1e. Yield 3.84 g (68%). MS: 545.6 $[M+Na]^+$; 528.5 $[M-H_2O]^+$; 306.3 $[M-Fmoc+H_2O]^+$.
  ii) A solution of Fmoc-Phe-OPfp (553 mg, 1 mmol) in THF (5 mL) was added to a solution of H-Cit-OH (184 mg, 1.05 mmol) and $NaHCO_3$ (88.2 mg, 1.05 mmol) in $H_2O$ (2.6 mL). THF (2 mL) was added to make the solution homogeneous and stirred for 10 h. THF was removed on a rotovap, the residue was diluted with $H_2O$ (10 mL) and iPrOH (1 mL) and acidified to pH=1 with 3% HCl. The product was extracted five times with an EtOAc:iPrOH=9:1 solution, rinsed with a mixture of brine:iPrOH=9:1, dried ($Na_2SO_4$) and concentrated in vacuo. Trituration with ether afforded 313 mg of pure product 1e (57%).

Fmoc-AlaCit-OH 1f was prepared from Fmoc-Ala-NHS and H-Cit-OH as described above for 1e-(a). Yield 77%. MS: 959.8 $[2M+Na]^+$; 938.1 $[2M+1]^+$; 491.4 $[M+Na]^+$; 469.9 $[M+1]^+$.

Crude Fmoc-ValCit-OH 1g was prepared from Fmoc-Val-NHS and H-Cit-OH as described above for 1b. The final purification was done by trituration with ether. Total yield 76%. MS: 1060.3 $[2M+3Na]^+$; 1015.7 $[2M+Na]^+$; 519.7 $[M+Na]^+$; 497.9 $[M+1]^+$.

Fmoc-Ala-Asn(DMCP)-OH 1h was prepared from Fmoc-Ala-NHS and H-Asn(DMCP)-OH as described above for 1b. Yield 95%. MS: 530.2 $[M+Na]^+$; 508.2 $[M+1]^+$; 426.0 $[M-DMCP+1]^+$.

Coupling with P-Aminobenzyl Alcohol, Preparation of Fmoc-AA-PABA and Fmoc-A-PABA 2a-m.

Products 1a-h were coupled with p-aminobenzyl alcohol (PABA) in presence of 2-ethoxy-1-ethoxycarbonyl-1,2-dihydroquinoline (EEDQ) to form 2a-h. Four representatives 3 j-l with only one amino acid attached to PABA moiety were also prepared.

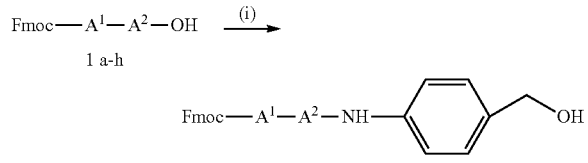

$A^1$=Gly, Glu(2PhiPr), Asn(DMCP), Phe, Ala, Val.
$A^2$=Gly, Lys(MMT), Cit, Asn(DMCP), Lys(CH$_3$)$_2$

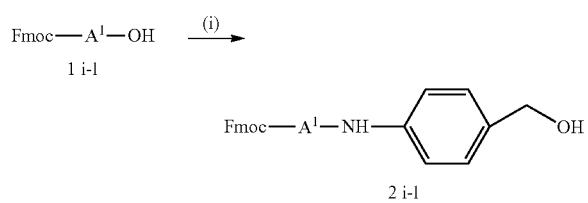

$A^1$=Lys(CH$_3$)$_2$, Leu, Asn(DMCP), Cit
Conditions: (i) PABA, EEDQ, THF

For Fmoc-GlyGly-PABA 2a, a solution of 1a (318 mg, 0.9 mmol) and PABA (220 mg, 1.8 mmol) in DCM (17 mL) and MeOH (6 mL) were stirred with EEDQ (444 mg, 1.8 mmol) for 10 h. All volatiles were removed on a rotovap, the residue was triturated with Et$_2$O and the product was filtered out and dried in vacuo. Yield 348 mg (84%).

For Fmoc-Glu(O-2PhiPr)Gly-PABA 2b, a solution of 1b (524 mg, 0.96 mmol) and PABA (142 mg, 1.55 mmol) in DCM (10 mL) was stirred with EEDQ (357 mg, 1.44 mmol) for 10 h. The workup was done as described above for 2a. Yield 462 mg (74%).

Fmoc-Asn(DMCP)Gly-PABA 2c, was prepared as described above for 2a. Yield 64%. MS: 621.5 [M+22]$^+$; 599.3 [M+1]$^+$.

Fmoc-PheLys(MMT)-PABA 2d, was prepared as described above for 2b. Yield 70%.

For Fmoc-PheCit-PABA 2e, a solution of 1e (5.98 g, 10.97 mmol) and PABA (2.70 g, 21.95 mmol) in DCM (150 mL) and MeOH (50 mL) was treated with EEDQ (5.43 g, 21.95 mmol) and stirred for 15 h. The workup was done as described above for 2a. Yield 6.14 g (86%). MS: 650.7 [M+1]$^+$; 527.3 [M−PABA+1]$^+$.

For Fmoc-AlaCit-PABA 2f, a solution of 1f (2.89 g, 6.17 mmol) and PABA (1.52 g, 12.34 mmol) in DCM (45 mL) and MeOH (15 mL) was treated with EEDQ (3.05 g, 12.34 mmol) and stirred for 15 h. The workup was done as described above for 2a. Yield 4.56 g (74%). MS (ES, neg. mode): 307.4 [M−263.6−1]$^-$; 349.9 [M−Fmoc−1]$^-$; 610, 608.4 [M+HCl−1]$^-$.

Fmoc-ValCit-PABA 2g was prepared as described above for 2b. (98%).

Fmoc-AlaAsn(DMCP)-PABA 2h was prepared as described above for 2a. Yield 59%. MS: 613.2 [M+1]$^+$; 531.4 [M−DMCP+1]$^+$; 408.2 [M−205+1]$^+$.

For Fmoc-Lys(CH$_3$)$_2$-PABA 2i, Fmoc-Lys(CH$_3$)$_2$—OH.HCl salt (433 mg, 1 mmol) and PABA (246 mg, 2 mmol) were dissolved in DCM (10 mL) and MeOH (1.5 mL), cooled to 5° C. and EEDQ (495 mg, 2 mmol) was added. The cooling bath was removed and the mixture was stirred for 10 h at room temperature. All volatiles were removed on a rotovap, the residue was triturated with Et$_2$O, and the crude product was filtered off. It was redissolved in a mixture of DCM (2 mL) and MeOH (1 mL) and precipitated again by adding dropwise into Et$_2$O (40 mL). Product was filtered and dried in vacuo. Yield 448 mg (83%).

For Fmoc-Leu-PABA 2j, a solution of Fmoc-Leu-OH (353 mg, 1 mmol), EEDQ (495 mg, 2 mmol) and PABA (222 mg, 1.8 mmol) in DCM (10 mL) was stirred for 10 h. All volatiles were removed on a rotovap, the residue was dissolved in Et$_2$O (40 mL), chilled on dry ice for 2 h and the solid was separated by centrifugation. The obtained crude material was purified on a column, eluent gradient of MeOH (1-2%) in CHCl$_3$. Yield 444 mg (97%). MS: 459.4 [M+1]$^+$.

Fmoc-Asn(DMCP)-PABA 2k was prepared as described for 2j. In workup instead of column purification after removing of DCM the residue was triturated with Et$_2$O, chilled to 0° C. and the crude product was filtered off. This treatment was repeated one more time followed by drying in vacuo. Yield 77%. MS: 542.5 [M+1]$^+$.

For Fmoc-Cit-PABA 2l, a solution of Fmoc-Cit-OH (345.7 mg, 0.87 mmol) and PABA (214 mg, 1.74 mmol) in DCM (10 mL) and MeOH (4 mL) was treated with EEDQ (430 mg, 1.74 mmol) and stirred for 15 h. The solid product was triturated three times with ether, and the product was filtered and dried. Yield 288 mg (67%). MS: 502.3 [M+1]$^+$; 485.5 [M−H$_2$O+1]$^+$; 263 [M−Fmoc−H$_2$O+1]$^+$; 179.0 [M−306+1]$^+$; 120.2 [M−365.3+1]$^+$.

Product 2m was prepared using different scheme: coupling of H-Lys(CH$_3$)$_2$-PABA derivative 3 with Fmoc-Phe-NHS.

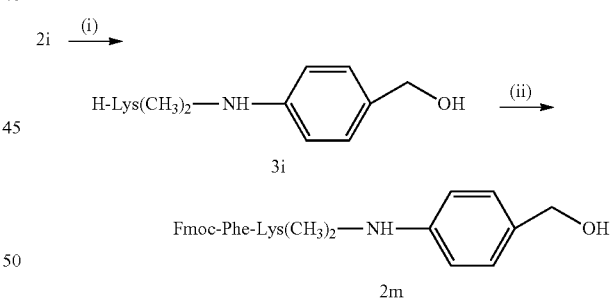

Conditions: (i) Triethylamine (Et$_3$N) in DMF, 10 h. (ii) Fmoc-Phe-NHS, disopropylethylamine (DIEA), DMF.

For Fmoc-PheLys(CH$_3$)-PABA 2m, Fmoc-Lys(CH$_3$)$_2$-PABA (2l) (448 mg, 0.83 mmol) was Fmoc deprotected by stirring with Et$_3$N (3.5 mL) in DMF (11 mL) for 10 h. All volatiles were removed on a rotovap at 40° C./oil pump vacuum to obtain the crude product 3l. This product was dissolved in DMF (7 mL), Fmoc-Phe-NHS (482 mg, 0.996 mmol) was added followed by DIEA (0.42 mL, 2.2 mmol) and the mixture was stirred for 10 h. The solvent with DIEA was removed on a rotovap at 40° C./oil pump vacuum to obtain crude 2m which was used without additional purification. MS: 549.4 [M+1]$^+$.

Preparation of H-AA-PABA 3a-h, m and H-A-PABA 3j-l

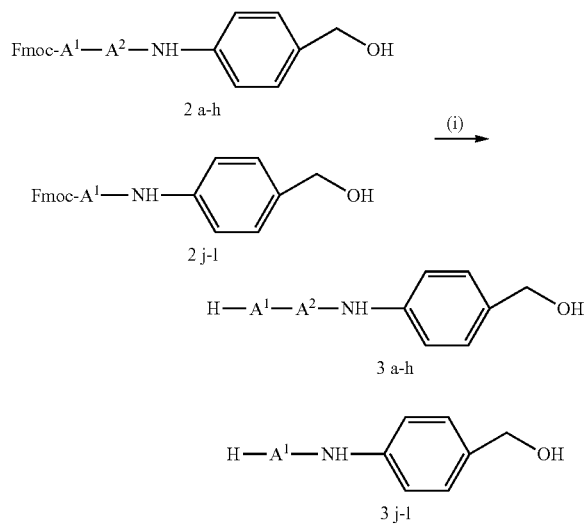

Conditions: (i) Et$_3$N in DMF, 10 h.

Fmoc-derivatives 2a-h, j-l were treated with Et$_3$N in DMF as described above for 31 followed by concentration and drying in vacuo. The crude products were dissolved in DMF to make 0.1 M solution and used without additional purification.

TABLE 1

| Intermediates of H-AA-PABA (1-3) | | |
|---|---|---|
|  | A$^1$ | A$^2$ |
| 1, 2, 3a | Gly | Gly |
| 1, 2, 3b | Glu(2PhiPr) | Gly |
| 1, 2, 3c | Asn(DMCP) | Gly |
| 1, 2, 3d | Phe | Lys(MMT) |
| 1, 2, 3e | Phe | Cit |
| 1, 2, 3f | Ala | Cit |
| 1, 2, 3g | Val | Cit |
| 1, 2, 3h | Ala | Asn(DMCP) |
| 1, 2, 3i | Lys(CH$_3$)$_2$ |  |
| 1, 2, 3j | Leu | — |
| 1, 2, 3k | Asn(DMCP) | — |
| 1, 2, 3l | Cit | — |
| 2, 3m | Phe | Lys(CH$_3$)$_2$ |

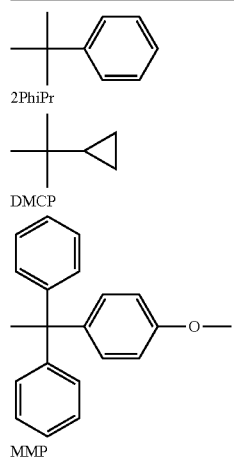

Preparation of Protease Cleavable NAG-Masking Reagents

Preparation of NAG(R$^1$, R$^2$, R$^3$)-L-AA-PABC-PNP (Tables 2, 3)

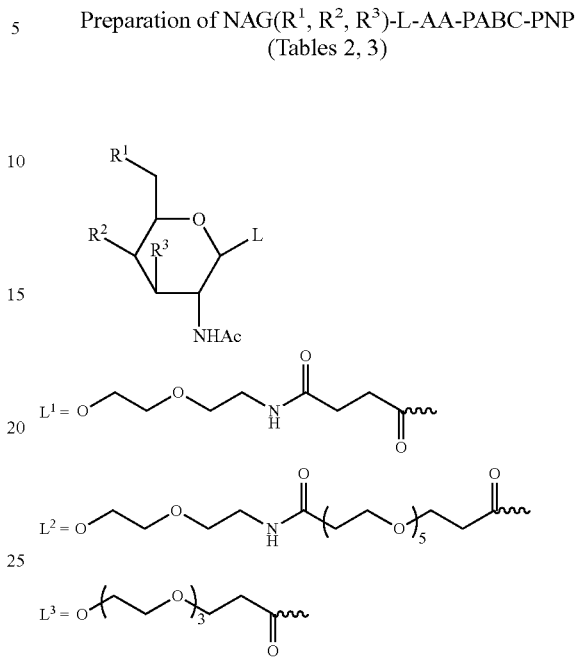

Preparation of NAG(R$^1$, R$^2$, R$^3$)-L-AA-PABC-PNP where R$^1$, R$^2$ and R$^3$ are protective groups and L is a linkage between galactosamine moiety (NAG) and dipeptide (AA) starts from preparation of NAG-L-CO$_2$H acids 6, 10a,b,13 and 17 which, following conversion into NHS ester, were used to acylate H-AA-PABA 2. In carbonates 21a-f designed for base sensitive polymers protective groups had to be removed before polymer modification. For this purpose in preparation of 10a, b,13 and 17 Ac-protective groups in GAL moiety were replaced with labile triethylsilyl (TES) and tert-butyldimethylsilyl (TBDMS) groups. Those groups can be removed using a 70% solution of trifluoroacetic acid (TFA) in H$_2$O at 0° C. without compromising base sensitive PNP-carbonate moiety.

a) In preparation NAG-L$^1$-CO$_2$H 6 where R$^1$=R$^2$=R$^3$=OAc Z-protected NAG-tetraacetate 4 [3-5] was Z-deprotected (H$_2$, Pd/C (10%), MeOH, CHCl$_3$ (20%) to obtain NAG-amine 5 which was than acylated with succinic anhydride. (succinic anhydride, Et$_3$N, DCM, 1 h).

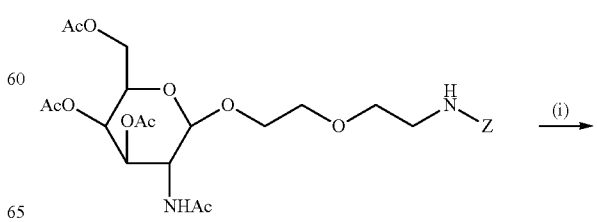

4

-continued

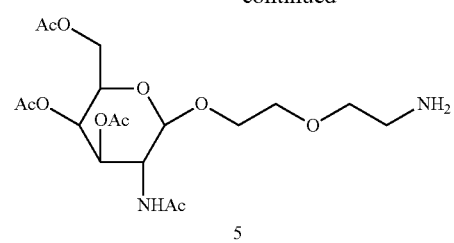

5

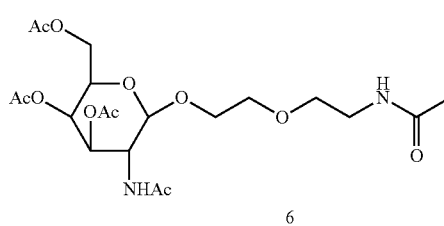

6

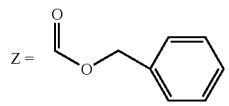

Conditions: (i) H$_2$, Pd/C (10%), MeOH, CHCl$_3$, (20%), (ii), Succinic anhydride, Et$_3$N, CDM, 1 h.

NAG-amine 5: For preparation of 5a solution of NAG 4 (6.74 g, 11.85 mmol) in MeOH (144 mL) and CHCl$_3$ (36 mL) was hydrogenated in the presence of 10% Pd/C (674 mg) at 1 atm. for 10 h. The catalyst was filtered off through celite, the product was concentrated and dried in vacuo. Yield 5.04 g (98%).

NAG-L$^1$-OH 6: For preparation of 6a solution of succinic anhydride (966 mg, 9.65 mmol) in DCM (30 mL) was added to NAG-amine 5 (4 g, 9.15 mmol) in DCM (50 mL) followed by Et$_3$N (1.964 mL, 14 mmol). After 1 h the reaction mixture was concentrated and dried in vacuo. The product was purified on a column, eluent gradient of MeOH (5-7%) in CHCl$_3$. Yield 3.1 g (63%). MS: 535.3 [M+1]$^+$; 330.3 [product of deglycosylation]$^+$.

b) NAG derivatives with easily removable silyl ether protective groups were prepared by O-deacetylation of 4 in a mixture of triethylamine in aqueous methanol followed by treatment with trialkylsilyl chlorides.

i) NAG-L$^1$-OH 10a,b. 10a: R$^1$=OTES and OTBDMS, R$^2$=OH, R$^3$=OTES; 10b: R$^1$=R$^3$=OTBDMS, R$^2$=OH.

Preparation of NAG 8a,b

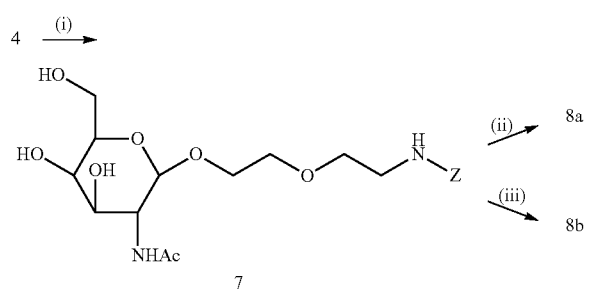

-continued

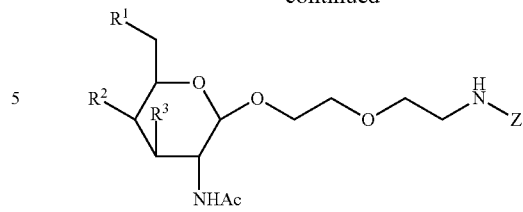

8a: R$_1$=OTBDMS and OTES, R$_2$=OH, R$_3$=OTES
8b: R$_1$=R$_3$=OTBDMS, R$_2$=OH Conditions: (i) Et$_3$N, MeOH, H$_2$O (5:7:6) 10 h. (ii) TBDM-SCl (1 eq.), imidazole, 1 h followed by TESCl (3 eq.), 10 h in DMF. (iii) TBDMSCl (3 eq.), imidazole, 10 h in DMF.

NAG derivative 7.

Preparation of 10a,b

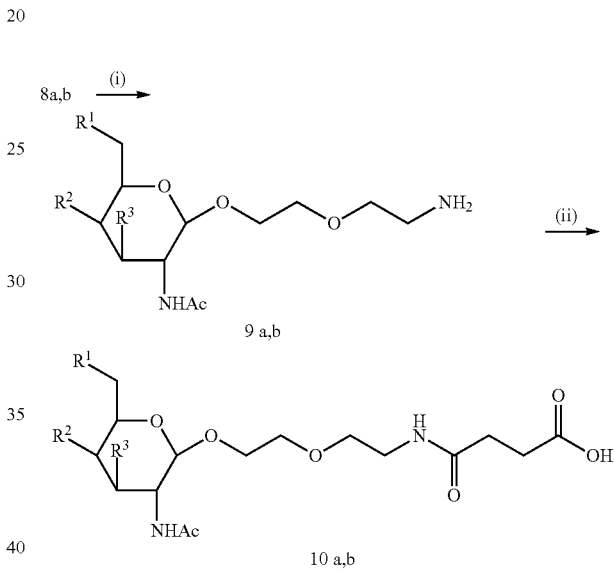

9, 10 a: R$_1$=OTBDMS and OTES, R$_2$=OH, R$_3$=OTES
9, 10 b: R$_1$=R$_3$=OTBDMS, R$_2$=OH Conditions: (i) H$_2$, Pd/C (10%), THF. (ii) succinic anhydride, Et$_3$N, DCM, 1 h.

For preparation of 7 NAG 4 (2 g, 3.52 mmol) was O-deacetylated by stirring in a solution of MeOH (10 mL), H$_2$O (32 mL), and Et$_3$N (25 mL) for 10 h. All volatiles were removed on a rotovap at 40° C. and the residue was dried by two evaporations of toluene from the reaction mixture. The product 7 was directly used in the following step. MS: 544.3 [M+Et$_3$N+1]$^+$; 443.7 [M+1]$^+$; 204 [product of deglycosylation]$^+$.

For preparation of 8a product 7 (1.76 mmol) in DMF (15 mL) was treated with imidazole (718 mg, 10.54 mmol) and TBDMSCl (265 mg, 1.76 mmol), stirred for 2 h and the reaction mixture was cooled to 0° C. TESCl (531 mg, 3.52 mmol) was added, stirred for 10 h, concentrated and dried in vacuo. The residue was taken in a mixture of EtOAc (110 mL) and H$_2$O (30 mL). The organic layer was separated, cooled to 5° C., washed with citric acid (5%), H$_2$O, NaHCO$_3$ and dried (Na$_2$SO$_4$). The crude product was passed through a column, eluent MeOH 2% in CHCl$_3$ to afford a mixture of TBDMS and TES di Si-protected NAG derivatives 8a. Yield 575 mg (49%). MS: 672.0 [M+1]$^+$; 432.5 [product of deglycosylation]$^+$.

For preparation of 8b a solution of 7 (1.76 mmol) in DMF (15 mL) was stirred with imidazole (718 mg, 10.56 mmol) and TBDMSCl (1.061 g, 7 mmol) for 10 h. The reaction mixture was processed as described above for preparation of 8a. Yield after column purification 767 mg (65%). M: 672.0 [M+1]$^+$; 432.7 [product of deglycosylation]$^+$.

Product 10a was prepared as a mixture of TBDMS and TES di Si-protected NAG derivatives following procedure described for 10b below.

For preparation of 10b compound 8b (920 mg, 1.37 mmol) was hydrogenated in THF (20 mL) in presence of Pc/C 10% (150 mg) at 1 atm for 10 h. The catalyst was filtered off through celite, the product 9b was concentrated and dried in vacuo.

The NAG-amine 9b without additional purification was dissolved in DCM (12 mL), succinic anhydride solution (140 mg, 1.40 mmol) in DCM (7 mL) was added followed by Et$_3$N (0.236 mL, 1.676 mmol) and stirred for 2 h. Solvent was removed on a rotovap and product was purified on a column, eluent 1% AcOH, 10% MeOH in CHCl$_3$. Yield 614 mg (72%).

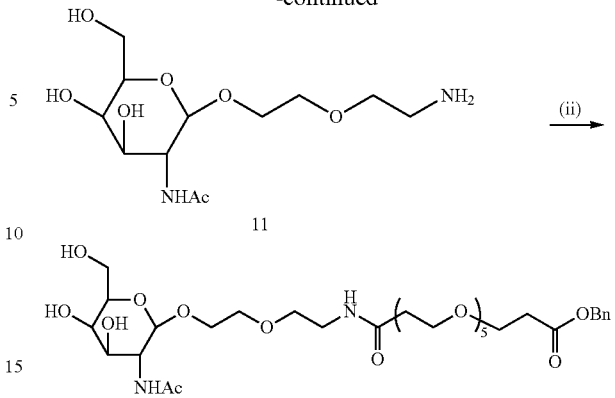

Conditions: (i) Et$_3$N, MeOH, H$_2$O (5:7:6) 10 h. (ii) NHS-PEG$_5$-CO$_2$Bn, Et$_3$N, DCM.

Preparation of NAG-L$^2$-OH 13

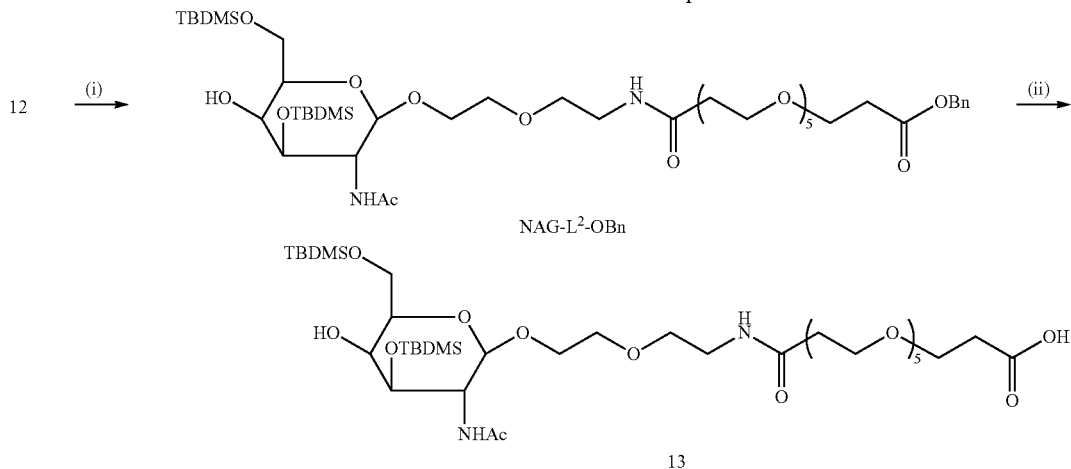

ii) NAG-L$^2$-OH 13. R$^1$═R$^3$═OTBDMS, R$^2$═OH. NAG Derivatives with Longer PEG Spacer.

For analogues with longer PEG spacers, the precursor 5 was first acetyl-deprotected to yield 11 (Et$_3$N, MeOH, H$_2$O (5:7:6) 10 h). 11 was then acylated with bis-dPEG$_5$half benzyl half NHS ester (Quanta product cat. #10237) to yield the benzyl ester 12 (NHS-PEG$_5$-CO$_2$Bn, Et$_3$N, DCM). 12 was subsequently bis-silylated with TBDMSCl (TBDMSCl (3 eq.), imidazole, 10 h in DMF) and debenzylated by hydrogenation (H2, Pd/C (10%), THF) to obtain acid 13.

Preparation of NAG-derivative 12

5 $\xrightarrow{(i)}$

Conditions: TBDMSCl (3 eq.), imidazole, 10 h in DMF. (vi) H$_2$, Pd/C (10%), THF.

NAG-PEG$_5$-SA benzyl ester 12. For preparation of NAG-amine 11 NAG-amine 5 (0.381 mmol) was O-deacetylated as described for precursor 7 (procedure for 8a,b). Product 11 was dried by two evaporations of toluene on a rotovap and dissolved in DMF (25 mL). Bis-dPEG$_5$half benzyl half NHS ester (200 mg, 0.381 mmol) was added to the reaction mixture followed by DIEA (0.079 mL, 0.457 mmol), stirred for 8 h and concentrated on a rotovap at 40° C./oil pump vacuum. Crude product 12 was used in the next step without additional purification. MS: 719.4 [M+1]$^+$; 516.4 [product of deglycosylation]$^+$.

For preparation of NAG-L$^2$-OBn dry product 12 was dissolved in DMF (5 mL), treated with TBDMSCl (230 mg, 1.524 mmol) followed by imidazole (156 mg, 2.29 mmol). The reaction mixture was stirred for 10 h, all volatiles were removed on a rotovap at 40° C./oil pump vacuum and the residue was taken in EtOAc (85 mL) and washed with HCl (1%), H$_2$O. The aqueous phases were combined and back extracted with EtOAc. The combined organic solutions were dried (Na$_2$SO$_4$), concentrated and purified on a column, eluent gradient of MeOH (3-6%) in CHCl$_3$. Yield of the benzyl ester 291 mg (80%). MS: 965.3 [M+NH$_4$]$^+$; 948.0 [M+1]$^+$; 516.4 [product of deglycosylation]$^+$.

For preparation of NAG-L²-OH 13 the ester NAG-L²-OBn was hydrogenated as described for 9b (procedure for 10b). Yield 98%. MS: 858.0 [M+1]⁺; 426.1 [product of deglycosylation]⁺. The product was used without additional purification.

iii) NAG-L³-OH 17. R¹=R³=OTBDMS, R²=OH. NAG Derivatives with Longer PEG Spacer.

17 was prepared by glycosylation of pentaacetate 14 [3-5] with PEG₄ mono-tBu ester (TMSOTf, DCE/HO-PEG₄-CO₂tBu, SnCl₄, DCM) to yield 15. 15 was hydrolyzed (HCO₂H, 10 h) to obtain the acid 16, which was then O-deacetylated (Et₃N, MeOH, H₂O (5:7:6) 10 h) and treated with TBDMSCl (TBDMSCl (3 eq.), imidazole, 10 h in DMF) to obtain bis-silylated NAG-acid 17.

Preparation of ester NAG(OAc)-3-L³-O-tBu 15

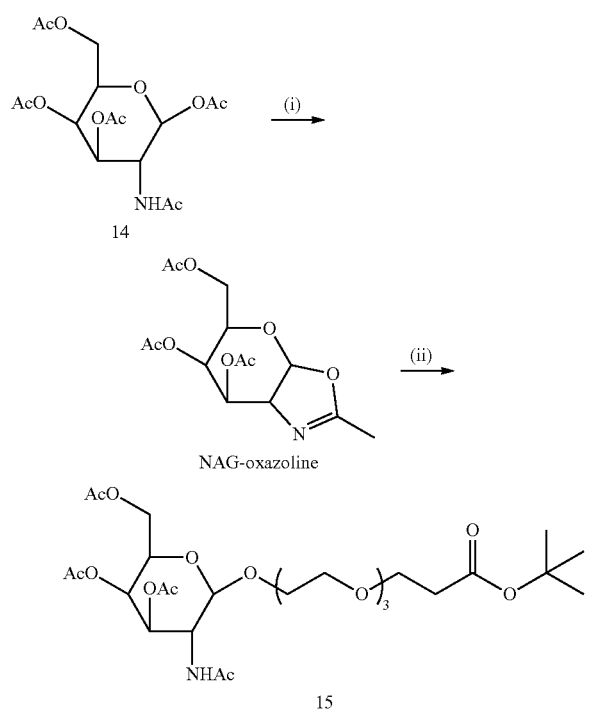

Conditions: (i) trimethylsilyl trifluoromethanesulfonate (TMSOTf), dichloroethane (DCE). (ii) t-butyl 12-hydroxy-4,7,10-trioxadodecanoate (HO-PEG₄-CO₂tBu), SnCl₄, dichloromethane (DCM).

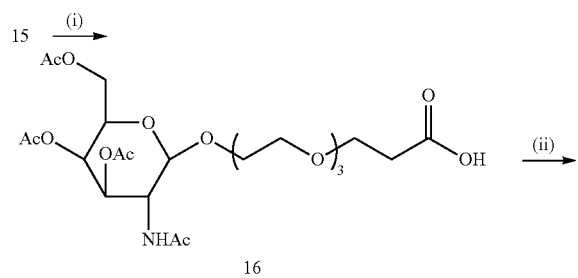

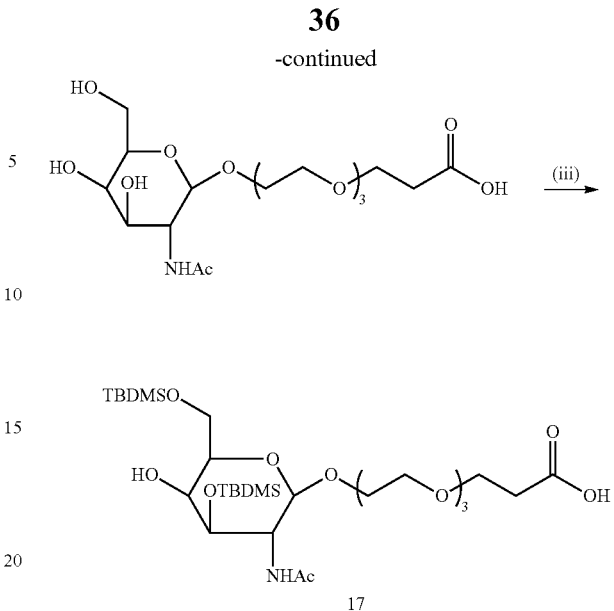

Conditions: (i) HCO₂H, 10 h. (ii) Et₃N, MeOH, H₂O (5:7:6) 10 h. (iii) TBDMSCl (3 eq.), imidazole, 10 h in DMF.

For ester NAG(OAc)₃-L³-O-tBu 15 pentacetyl derivative of galactosamine 14 (10 g, 25.64 mmol) was dried by two evaporations from toluene. The resulting white glass was treated with TMSTf (5.18 mL, 28.6 mmol) in DCE (223 mL), and stirred at 60° C. for 16 h. The reaction mixture was cooled to 0° C., quenched with TEA (2.6 mL), diluted with CHCl₃ (300 mL) and washed twice with a NaHCO₃ solution and with brine. The separated organic solution was treated with MgSO₄, concentrated, and dried in vacuo. The crude oxazoline derivative was used without additional purification. Yield 8.14 g (96%). MS: 368.1 [M+K]⁺; 352.2 [M+Na]⁺; 330.2 [M+1]⁺.

To a stirring mixture of oxazoline derivative (5.28 g, 16 mmol), t-butyl 12-hydroxy-4,7,10-trioxadodecanoate (5.12 g, 18.4 mmol) and CaSO₄ (20 g) in DCM (270 mL) was added dropwise SnCl₄ (0.84 mL, 0.84 mmol). The solution was stirred for 16 h, filtered, diluted with CHCl₃ (250 mL), washed twice with NaHCO₃ solution and brine. Product was dried with MgSO₄, and concentrated. The crude was purified on a column, eluent gradient of MeOH (0-7%) in ethyl acetate. Yield 4.83 g (50%). MS: 630.8 [M+Na]⁺; 625.5 [M+NH₄]⁺; 608.4 [M+1]⁺; 552.6 [M−t−Bu+1]⁺; 330.2 [product of deglycosylation]⁺.

For NAG(OAc)₃-L³-OH 16, tert-butyl ester 15 (1.99 g, 3.27 mmol) was stirred in neat formic acid (54 mL) for 16 h and all volatiles were removed in vacuo followed by three evaporations of toluene. Product was dried with vacuum oil pump for 2 h and used without additional purification. Yield 1.77 g (98%). MS: 330.2 [product of deglycosylation]⁺; 590.4 [M+K]⁺; 574.6 [M+Na]⁺; 569.6 [M+NH₄]⁺; 552.6 [M+1]⁺.

For NAG(R¹, R², R³)-L³-OH 17 (R¹=R³=OTBDMS, R²=OH), product 16 was O-deacetylated, treated with TBDMSCl as in preparation of 8b and purified on a column, eluent 3% MeOH, 0.5% AcOH in CHCl₃. Yield 18%. MS: 1228.7 [M+1]⁺, 796.7 [product of deglycosylation]⁺.

All five obtained acids 6, 10a,b, 13, 17 were converted into NHS ester 18a-e in reaction with NHS and DCC (NHS, DCC, DCM, 10 h).

6,10,13,17 →(i) 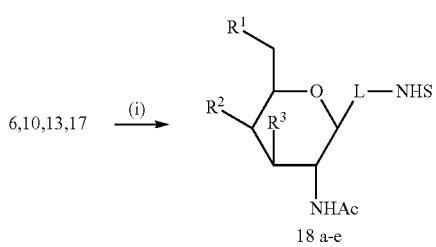

18 a-e

Products 18b-e were prepared as described for 18a.

c) Formation of 20a-l, 3a-h were acylated with NHS ester of hydroxyl-protected NAG-derivatives 18a-e (DIEA, DMF, 5-10 h) to provide 19a-l. Products 19a-l were than treated with 5 equivalents of bis(p-nitrophenyl)carbonate (($PNP)_2$CO) (($PNP)_2$CO, dioxane or DCM, 40-50° C., 15-24 h) to yield the O-Acetyl protected PNP carbonate derivatives 20a-l. Products 20a-e were used directly for modification of peptides. The acetyl groups and protective groups 2PhiPr, DMCP, MMT from amino acids were removed post modification during consecutive treatment of DPC with TFA and $Et_3N$.

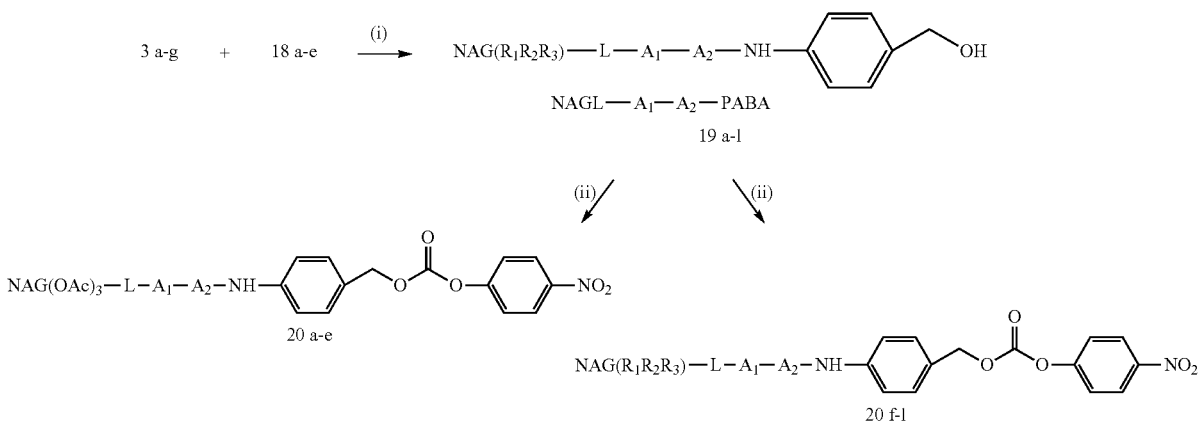

-continued

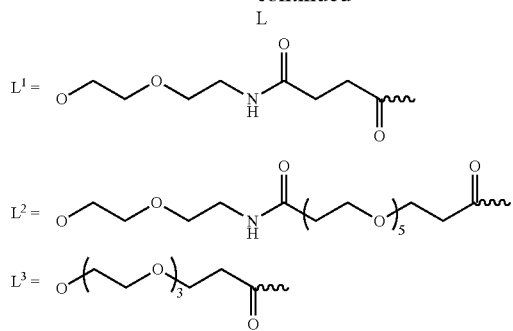

18a $R^1=R^2=R^3=OAc$, $L^1$
18b $R^1=$OTBDMS and OTES, $R^2=$OH, $R^3=$TES, $L^1$
18c $R^1=R^3=$OTBDMS, $R^2=$OH, $L^1$
18d $R^1=R^3=$OTBDMS, $R^2=$OH, $L^2$
18e $R^1=R^3=$OTBDMS, $R^2=$OH, $L^3$ Conditions: (i) NHS, DCC, DXCM, 10 h.

For preparation of NAG-L-NHS 18a-e was used procedure described for 18c below. For product 18c, an ice cold solution of 10b (614 mg, 0.964 mmol) and NHS (122 mg, 1.061 mmol) in DCM (15 mL) was treated with DCC (219 mg, 1.061 mmol), stirred for 30 min on ice and 8 h at 20° C. The reaction mixture was cooled to 0° C., DCU was filtered off, the residue was concentrated and dried in vacuo. The crude product was dissolved in DMF to make 0.05 M solution and used without additional purification.

Conditions: (i) DIEA, DMF, 5-10 h. (ii) $(PNP)_2$CO, dioxane or DCM, 25-60° C., 16-48 h. NAG($R^1R^2R^3$)-L-AA-PABA 19a-l.

For product 19a ($R^1=R^2=R^3=$OAc, L=$L^1$, AA=GlyGly), an NAG-NHS ester 18a solution in DMF (0.05M) (0.282 mmol) was treated with 0.1 M of solution of 3a (0.282 mmol) in DMF and DIEA (59 μL, 0.338 mmol). In 3 h all volatiles were removed on a rotovap at 40° C./oil pump vacuum, triturated with $Et_2O$ and purified on a column, eluent: gradient EtOAc:$CHCl_3$:MeOH=8:7:5-8:7:6. Yield 114 mg (53%). MS: 754.4 [M+1]$^+$.

Product 19b ($R^1=R^2=R^3=$OAc, L=$L^1$, AA=Glu(2PhiPr)Gly) was prepared as described for 19a and purified on a column, eluent EtOAc:$CHCl_3$:MeOH=8:7:3. Yield 64%. MS: 944.5 [M+1]$^+$.

For product 19c ($R^1=R^2=R^3=$OAc, L=$L^1$ AA=Asn(DMCP)Gly), to a solution of 3c (0.43 mmol) and DIEA (83 μL, 0.476 mmol) in DMF (2.15 mL) was added a solution of 18a (0.43 mmol) in DMF (2.15 mL). The mixture was stirred for 16 h, filtered and all volatiles were removed on a rotovap at 40° C./oil pump vacuum. The crude product was triturated with $Et_2O$ and purified on a column, eluent $CHCl_3$:acetone:MeOH (5:5:1). Yield 242 mg (62%). MS: 915.3 [M+Na]$^+$; 910.6 [M+$NH_4$]$^+$; 893.6 [M+1]$^+$.

Product 19d ($R^1=R^2=R^3=$OAc, L=$L^1$ AA=PheLys(MMT)) was prepared as described for 19a and purified on a column, eluent gradient of MeOH (5-6%) in $CHCl_3$. Yield 56%. MS: 1187.9 [M+1]$^+$.

For product 19e ($R^1=R^2=R^3=$OAc, L=$L^1$, AA=PheCit), to a solution of 3e (0.57 mmol) and DIEA (119 μL, 0.684 mmol) in DMF (3 mL) was added a solution of 18a (0.57 mmol) in DMF (3 mL). The mixture was stirred for 16 h, filtered and all volatiles were removed on a rotovap at 40° C./oil pump vacuum. The crude product was precipitated into Et$_2$O (45 mL) from CHCl$_3$:MeOH (5 mL) and used without additional purification. Yield 392 mg (73%). MS: 966.8 [M+Na]$^+$; 944.7 [M+1]$^+$; 926.8 [M–H$_2$O]$^+$; 821.5 [M–PABA+1]$^+$; 615.6 [M–NAcGal+1]$^+$; 492.3 [M–PABA–NAcGa1+1]$^+$.

Product 19f (R$^1$=R$^3$=OTBDMS, R$^2$=OH, L=L$^1$, AA=AlaCit) was prepared as described for 19e and used without additional purification. Yield 50%. MS: 993.2 [M+Na]$^+$; 971.0 [M+1]$^+$; 539.6 [product of deglycosylation]$^+$.

Product 19g (R$^1$=R$^3$=OTBDMS, R$^2$=OH L=L$^1$, AA=ValCit) was prepared as described for 19f and used in the next step without additional purification. Yield 67%: 998.9 [M+1]$^+$.

Product 19h (R$^1$=R$^3$=OTBDMS, R$^2$=OH L=L$^1$, AA=Glu(2PhiPr)Gly) was prepared as described for 19a and purified on a column, eluent solution of NH$_4$OH 3% and MeOH 7.5% in DCM. Yield 15%. MS: 1047.2 [M+1]$^+$, 615.7, 432.6 [product of deglycosylation]$^+$.

Product 19i (R$^1$=R$^3$=OTBDMS, R$^2$=OH, L=L$^1$, AA=PheCit) was prepared as described for preparation of 19e and used without additional purification. Yield 50%. MS: 1068.7 [M+Na]$^+$; 1047.3 [M+1]$^+$; 615.4 [product of deglycosylation]$^+$; 432.5 [product of deglycosylation]$^+$.

Product 19j (R$^1$=OTBDMS and OTES, R$_2$=OH, R$^3$=OTES, L=L$^1$, AA=PheCit) was prepared from 3e and 18b as a mixture of C-3 and C-6 O-TBDMS and O-TES protected NAG derivatives as described for preparation of 19e and used in the next step without additional purification. Yield 76%. MS: 1047.4 [M+1]$^+$, 615.8 [product of deglycosylation]$^+$.

Product 19k R$^1$=R$^3$=OTBDMS, R$^2$=OH, L=L$^2$, AA=PheCit was prepared as described for 19e and used in the next step without additional purification. Yield 67%: 1268.2 [M+1]$^+$; 835.9 [product of deglycosylation]$^+$.

Product 19l R$^1$=R$^3$=OTBDMS, R$^2$=OH, L=L$^3$, AA=PheCit was prepared as described for 19e and purified on a column, eluent 5% MeOH solution in CHCl$_3$ Yield 60%. MS: 1064.0 [M+1]$^+$; 632.7 [product of deglycosylation]$^+$.

NAG-AA-PABC-PNP 20a-1

For product 20a (R$^1$=R$^2$=R$^3$=OAc, L=L$^1$, AA=GlyGly), a suspension of 19a (100 mg, 0.132 mmol), (PNP)$_2$CO (202 mg, 0.663 mmol) and DIEA (0.07 mL, 0.396 mmol) in dioxane (5 mL) was stirred for 8 h in the dark at 40° C. Another portion of (PNP)$_2$CO (121 mg, 0.397 mmol) and DIEA (0.04 mL, 0.226 mmol) were added and stirring was continued another 8 h at 40° C. All volatiles were removed on a rotovap and the product was purified on a column, eluent: CHCl$_3$:EtOAc:MeOH=7:8:3. Yield 84 mg (69%).

For product 20b (R$^1$=R$^2$=R$^3$=OAc, L=L$^1$, AA=Glu(2PhiPr)Gly), a solution of 19b (160 mg, 0.169 mmol), (PNP)$_2$CO (258 mg, 0.847 mmol) and DIEA (0.09 mL, 0.507 mmol) in DCM (10 mL) was stirred in the dark for 10 h, concentrated on a rotovap and the product was purified on a column, eluent: 5-6% MeOH solution in CHCl$_3$. Yield 174 mg (92%).

For product 20c (R$^1$=R$^2$=R$^3$=OAc, L=L$^1$ AA=Asn(DMCP)Gly), a solution of 19c (127 mg, 0.142 mmol), (PNP)$_2$CO (216 mg, 0.710 mmol) and DIEA (74 μL, 0.426 mmol) in DCM (5 mL) was stirred in the dark for 16 h, concentrated on a rotovap and the product was purified on a column, eluent: CHCl$_3$:EtOAc:MeOH (7:2.2:0.8). Yield 110.6 mg (74%). MS: 1080.9 [M+Na]$^+$; 1058.7 [M+1]$^+$.

Product 20d (R$^1$=R$^2$=R$^3$=OAc, L=L$^1$ AA=PheLys(MMT)) was prepared as described for 20b and purified on a column, eluent: CHCl$_3$:EtOAc:MeOH=9:7:1 Yield 76 mg (47%).

For product 20e (R$^1$=R$^2$=R$^3$=OAc, L=L$^1$, AA=PheCit), a solution of 19e (164 mg, 0.173 mmol), (PNP)$_2$CO (528 mg, 1.73 mmol) and DIEA (182 μL, 1.04 mmol) in dioxane (17 mL) was stirred in the dark at 60° C. for 16 h and all volatiles were removed on a rotovap.

The residual DIEA was removed by two consecutive evaporations of DMF on a rotovap at 40° C./oil pump vacuum and the product was purified on a column, eluent CHCl$_3$:EtOAc:MeOH (8:1.5:0.5) followed by CHCl$_3$:MeOH (7:1). Yield 85 mg (44%). MS: 1132.0 [M+Na]$^+$; 1110.1 [M+1]$^+$; 780.8 [product of deglycosylation]$^+$.

Product 20f (R$^1$=R$^3$=OTBDMS, R$^2$=OH, L=L$^1$, AA=AlaCit) was prepared as described for 20e and purified on a column, eluent: CHCl$_3$:EtOAc:MeOH=9:10:1. Yield 153 mg (36%).

Product 20g (R$^1$=R$^3$=OTBDMS, R$^2$=OH, L=L$^1$, AA=ValCit) was prepared as described for 20e and purified on a column, eluent CHCl$_3$:EtOAc:MeOH=16:3:1. Yield 44%. MS: 1164.5 [M+1]$^+$.

Product 20h (R$^1$=R$^3$=OTBDMS, R$^2$=OH, L=L$^1$, AA=Glu(2PhiPr)Gly) was prepared as described for 20b and purified on a column, eluent CHCl$_3$:EtOAc:MeOH=8:7:1. Yield 77%.

For product 20i (R$^1$=R$^3$=OTBDMS, R$^2$=OH, L=L$^1$, AA=PheCit), a solution of 19i (316 mg, 0.297 mmol), (PNP)$_2$CO (913 mg, 2.97 mmol) and DIEA (310 μL, 1.78 mmol) in dioxane (7 mL) was stirred in the dark at 65° C. for 40 h and all volatiles were removed on a rotovap. The residual DIEA was removed by two consecutive evaporations of DMF on a rotovap at 40° C./oil pump vacuum and the product was purified on a column, eluent CHCl$_3$:EtOAc:MeOH (8:1.5:0.5) followed by CHCl$_3$:MeOH (92:08). Yield 297 mg (81%). MS: 1246.7 [M+NH$_4$]$^+$; 1228.7 [M+1]$^+$; 797.6 [product of deglycosylation]$^+$; 432.7 [product of deglycosylation]$^+$.

Product 20j (R$^1$=OTBDMS and OTES, R$_2$=OH, R$^3$=OTES, L=L$^1$, AA=PheCit), product 20j as a mixture of C-3 and C-6 O-TBDMS and O-TES protected NAG derivatives was prepared as described for 20e and purified on a column, eluent CHCl$_3$:EtOAc:MeOH=16:3:1 followed by 10% MeOH in CHCl$_3$. Yield 50%. MS: 1212.0 [M+1]$^+$, 480.0 [product of deglycosylation]$^+$.

Product 20k (R$^1$=R$^3$=OTBDMS, R$^2$=OH, L=L$^2$, AA=PheCit) was prepared as described for 20e and purified on a column, eluent gradient of MeOH (8-10%) in CHCl$_3$. Yield 85%. Product was used directly in the next step.

For product 20l (R$^1$=R$^3$=OTBDMS, R$^2$=OH, L=L$^3$, AA=PheCit), solution of 19l (316 mg, 297 mmol), (PNP)$_2$CO (912 mg, 3 mmol) and DIEA (0.31 mL, 1.78 mmol) in dioxane (8 mL) was stirred under Ar in the dark at 60° C. for 48 h. All volatiles were removed on a rotovap and the product was purified on a column, eluent: CHCl$_3$:EtOAc:MeOH=16:3:1. Yield 297 mg (81%).

NAG-L-AA-PABC-PNP 21a-f (R$^1$=R$^2$=R$^3$=OH), deprotection of 20f-l

Formation of 21a-f. For modification of base sensitive polyacrylates, the protective groups on NAG and dipeptide AA were removed before attachment to polymer by treatment of 20f-l with a mixture of TFA:H$_2$O=3:1(TFA/H$_2$O=3:1, 5° C., 2-3 h) to provide NAG-dipeptide masking reagents 21a-f.

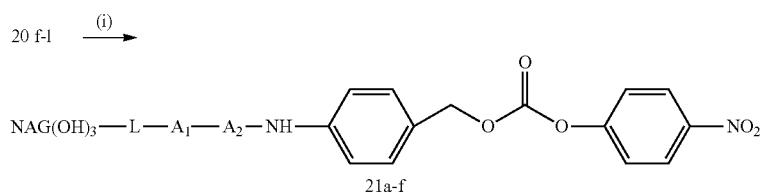

20 f-l —(i)→ 21a-f

Conditions: TFA/H$_2$O=3:1, 5° C., 2-3 h

For product 21a (AA=AlaCit, L=L$^1$) compound 20f (150 mg, 0.132 mmol) was stirred in an ice cold TFA:H$_2$O=3:1 solution (2 mL) for 4 h and added dropwise to stirring Et$_2$O (20 mL). The precipitate was separated and dried by evaporation of toluene on a rotovap/30° C. and then in vacuo. Yield 112 mg (94%). MS: 907.2 [M+1]$^+$; 704.4 [product of deglycosylation]$^+$.

For product 21b (AA=ValCit, L=L$^1$) compound 20g (305 mg, 0.26 mmol) was stirred in an ice cold TFA:H$_2$O=3:1 solution (5 mL) for 1 h and added dropwise to stirring Et$_2$O (45 mL). The solid product was separated and dried by evaporation of toluene on a rotovap/30° C. and then in vacuo. Yield 193 mg (79%). MS: 935.8[M+1]$^+$, 732.7 [product of deglycosylation]$^+$.

Product 21c (AA=GluGly, L=L$^1$) was prepared as described for 21b. Yield 55 mg (98%). MS: 865.5 [M+1]$^+$, 662.3 [product of deglycosylation]$^+$.

Product 21d (AA=PheCit, L=L$^1$) was prepared as described for 21b. MS: 983.7 [M+1]$^+$, 780.9 [product of deglycosylation]$^+$.

For product 21e (AA=PheCit, L=L$^2$) compound 20k was stirred in an ice cold TFA:H$_2$O=3:1 solution (5 mL) for 1.5 h under conditions described for 21b. Yield 25% counting from 19k. MS: 1203.9 [M+1]$^+$, 1001.0 [product of deglycosylation]$^+$.

Product 21f (AA=PheCit L=L$^3$) was prepared from 20l using 3 h deprotection under conditions described for 21b. Yield 75%. MS: 1203.9 [M+1]$^+$, 1001.0 [product of deglycosylation]$^+$.

TABLE 3

Final NAG-L-A$_1$A$_2$-PABC used for DPC preparation. (20, 21)

| compound | A$_1$ | A$_2$ | L |
|---|---|---|---|
| 20a | Gly | Gly | L$_1$ |
| 20b | Glu | Gly | L$_1$ |
| 20c | Asn | Gly | L$_1$ |
| 20d | Phe | Lys | L$_1$ |
| 20e | Phe | Cit | L$_1$ |
| 21a | Ala | Cit | L$_1$ |
| 21b | Val | Cit | L$_1$ |
| 21c | Glu | Gly | L$_1$ |
| 21d | Phe | Cit | L$_1$ |
| 21e | Phe | Cit | L$_2$ |
| 21f | Phe | Cit | L$_3$ |

Preparation of Protease Cleavable PEG-Masking Reagents

The amino group of any of H-AA-PABA 3b,e,g,h,j,k-m was acylated with an NHS ester of PEG-acid (DIEA, DMF, 5-10 h) to yield 22a-k. The hydroxyl group in product 22a-k was then converted into p-nitrophenyl carbonate ((PNP)$_2$CO, dioxane or THF, 40-60° C., 10 h) to yield 23a-k. For 23a,d,g, protective groups from Asn and Glu were removed by treatment with aqueous TFA (TFA/H$_2$O=3:1, 5° C., 2-3 h) to obtain desired products 24a-c. (Can you retain consistency by

TABLE 2

Intermediates NAG-L-AA-PABA (19) and NAG-L-AA_PABC (20)

| compound | A$_1$ | A$_2$ | L | R$_1$ | R$_2$ | R$_3$ |
|---|---|---|---|---|---|---|
| 19a | Gly | Gly | L$_1$ | OAc | OAc | OAc |
| 19b | Glu(2PhiPr) | Gly | L$_1$ | OAc | OAc | OAc |
| 19c | Asn(DMCP) | Gly | L$_1$ | OAc | OAc | OAc |
| 19d | Phe | Lys(MMT) | L$_1$ | OAc | OAc | OAc |
| 19e | Phe | Cit | L$_1$ | OAc | OAc | OAc |
| 19, 20f | Ala | Cit | L$_1$ | OTBDMS | OH | OTBDMS |
| 19, 20g | Val | Cit | L$_1$ | OTBDMS | OH | OTBDMS |
| 19, 20h | Glu(2PhiPr) | Gly | L$_1$ | OTBDMS | OH | OTBDMS |
| 19, 20i | Phe | Cit | L$_1$ | OTBDMS | OH | OTBDMS |
| 19, 20j | Phe | Cit | L$_1$ | OTBDMS, TES | OH | OTES |
| 19, 20k | Phe | Cit | L$_2$ | OTBDMS | OH | OTBDMS |
| 19, 20l | Phe | Cit | L$_3$ | OTBDMS | OH | OTBDMS | converting 23a, d, g to 24a, d, g?) Also, is there consistency between the amino acids for each letter between NAG and PEG versions?

Preparation of PEG$_n$-AA-PABA 22a-k

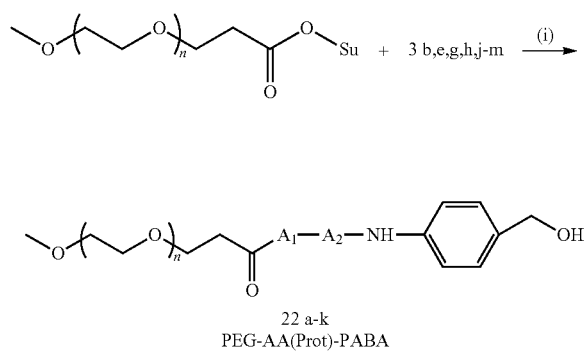

22 a-k
PEG-AA(Prot)-PABA

Conditions: (i) DIEA, DMF, 5-10 h.

Product 22a (n=11, AA=GluGly). A 0.1M solution of 3b in DMF (3.5 mL, 0.35 mmol) was stirred for 10 h with PEG$_{11}$-NHS ester (240 mg, 0.35 mmol) and DIEA (0.061 mL, 0.35 mmol). All volatiles were removed on a rotovap at 40° C./oil pump and the product was purified on a column, eluent: CHCl$_3$:MeOH:AcOH=38:2:1. Yield 274 mg (78%) MS: 1015.6 [M+NH$_4$]$^+$, 998.7 [M+1]$^+$.

Product 22b (n=11, AA=PheCit). To a solution of 3e (0.88 mmol) and DIEA (167 µL, 0.96 mmol) in DMF (3 mL) was added a solution of PEG$_{11}$-NHS ester (0.80 mmol) in DMF (3 mL). The mixture was stirred for 16 h, filtered and all volatiles were removed on a rotovap at 40° C./oil pump vacuum. The crude was precipitated into Et$_2$O (45 mL) from CHCl$_3$:MeOH (5 mL) and purified on a column, eluent a gradient of MeOH (10-16%) in CHCl$_3$. Yield 420 mg (53%). MS: 1015.9 [M+H$_2$O]$^+$; 998.8 [M+1]$^+$; 981.1 [M–H$_2$O]$^+$.

Product 22c (n=11, AA=ValCit). Product 22f was prepared from crude 3g (obtained from 300 mg, 0.5 mmol of 2g), PEG$_{11}$-NHS ester (298 mg, 0.435 mmol) and DIEA (0.09 mL, 0.522 mmol) as described for 22a. Following concentration on a rotovap at 40° C./oil pump the product was suspended in a MeOH:DCM=1:1 mixture (6 mL), sonicated, filtered and precipitated into Et$_2$O (50 mL). The solid was separated and the procedure repeated again. The residual solvents were removed in vacuo. Yield 283 mg (60%). MS: 951.5 [M+1]$^+$.

Product 22d (n=11, AA=AlaAsn(DMCP)). To a solution of 3h (0.56 mmol) and DIEA (116 µL, 0.67 mmol) in DMF (3 mL) was added a solution of PEG$_{11}$-NHS ester (0.56 mmol) in DMF (3 mL). The mixture was stirred for 16 h, filtered and all volatiles were removed on a rotovap at 40° C./oil pump vacuum. The residue was dissolved in a CHCl$_3$:MeOH=1:1 mixture (5 mL) and precipitated into chilled (0° C.) Et$_2$O (45 mL). The solid was purified on a column, eluent gradient of MeOH (3-14%) in DCM. Yield 261 mg (49%). MS: 983.7 [M+Na]$^+$; 979.1 [M+NH$_4$]$^+$; 961.8 [M+1]$^+$; 943.9 [M–H$_2$O+1]$^+$.

Product 22e (n=11, AA=PheLys(Me$_2$)). Product 22e was prepared as described for 22a. Purification was done using HPLC column Nucleodur C-18, 250×4.6, eluent ACN—H$_2$O (0.1% TFA), ramp 15-30%. MS: 998.1 [M+1]$^+$. The isolated product was desalted on Dowex 1×8 resin, eluent H$_2$O. Yield 40%.

Product 22f (n=11, AA=Leu). Product 22f was prepared as described for 22a and purified on a column, eluent: CHCl$_3$:EtOAc:MeOH:AcOH=9:7:2:0.04. Yield 48%. MS: 824.9 [M+NH$_4$]$^+$.

Product 22g (n=11, AA=Asn(DMCP). Crude 3k (obtained from 419 mg, 0.77 mmol of 2k), Peg$_{11}$NHS ester (200 mg, 0.292 mmol) and DIEA (0.06 mL, 0.35 mmol) were stirred in DCM (5 mL) for 10 h. The solvent was removed on a rotovap and the product was purified on a column, eluent CHCl$_3$:EtOAc:MeOH AcOH=4.5:3.5:1:0.02. Yield 254 mg (37%). MS: 891.1 [M+1]$^+$.

Product 22h (n=11 AA=Cit). To a solution of 3l (0.50 mmol) and DIEA (104 µL, 0.60 mmol) in DMF (2.5 mL) was added a solution of PEG$_{11}$-NHS ester (0.50 mmol) in DMF (2.5 mL).

The mixture stirred for 16 h, filtered and all volatiles were removed on a rotovap at 40° C./oil pump vacuum. The residue was dissolved in a CHCl$_3$:MeOH=1:1 mixture (5 mL) and precipitated into Et$_2$O (45 mL). Precipitation was repeated two more times and the product was used without additional purification. Yield 340 mg (80%). MS: 869.4 [M+NH$_4$]$^+$; 851.9 [M+1]$^+$.

Product 22i (n=23, AA=PheCit). To a solution of 3e (0.72 mmol) and DIEA (130 µL, 0.74 mmol) in DMF (3 mL) was added a solution of PEG$_{23}$-NHS ester (0.60 mmol) in DMF (3 mL). The mixture was stirred for 16 h, filtered and all volatiles were removed on a rotovap at 40° C./oil pump vacuum. The residue was dissolved in a CHCl$_3$:MeOH=1:1 mixture (5 mL) and precipitated into Et$_2$O (45 mL). The solid product was purified on a column, eluent gradient of MeOH (7-12%) in CHCl$_3$. Yield 487 mg (53%). MS: 1555.2 [M+Na]$^+$; 1544.7 [M+NH$_4$]$^+$; 1527.7 [M+1]$^+$.

Product 22j (PEG with average MW 1000. AA=PheCit). A mixture of mPEG-1000-alcohol (Fluka) (0.173 g, 0.173 mmol), N,N-disuccinimidyl carbonate (62 mg, 0.242 mmol), and TEA (0.101 mL, 0.726 mmol) were stirred in MeCN (1 mL) for 16 h. All volatiles were removed on a rotovap and the crude residue was dissolved in CHCl$_3$ (10 mL). The organic layer was washed with H$_2$O (1 mL, pH=5), then brine, dried over Na$_2$SO$_4$ and concentrated to afford PEG-1000-NHS carbonate. This product was stirred for 16 h with 3e (0.121 mmol) and DIEA (30 µL, 0.173 mmol) in DMF (1 mL), filtered and all volatiles were removed on a rotovap at 40° C./oil pump vacuum. The residue was dissolved in a CHCl$_3$:MeOH=1:1 mixture (5 mL) and precipitated into Et$_2$O (45 mL). Precipitation was repeated two more times and the product was used without additional purification. Yield 134 mg (79%).

Product 22k (n=23, AA=ValCit). To a solution of 3g (1.0 mmol) and DIEA (183 µL, 1.04 mmol) in DMF (4 mL) was added a solution of PEG$_{23}$-NHS ester (0.87 mmol) in DMF (4 mL). The mixture was stirred for 16 h, filtered and all volatiles were removed on a rotovap at 40° C./oil pump vacuum. The residue was dissolved in a CHCl$_3$:MeOH=1:1 mixture (5 mL) and precipitated into Et$_2$O (45 mL). Precipitation was repeated two more times and the product was used without additional purification. Yield 1.0 g (77%). MS: 1496.1 [M+NH$_4$]$^+$; 1479.3 [M+1]$^+$.

PEG-AA-PABC-PNP 23a-k

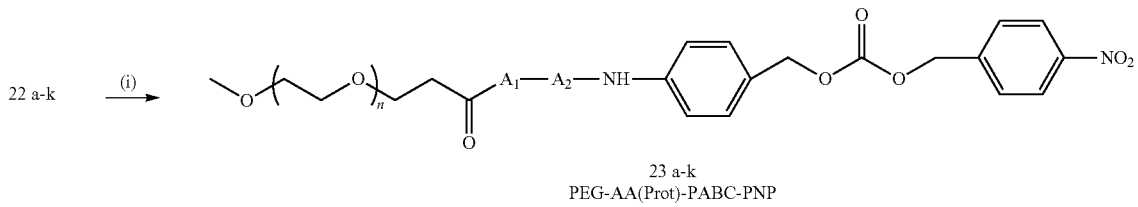

23 a-k
PEG-AA(Prot)-PABC-PNP

Condition: (i) (PNP)$_2$CO, dioxane or THF, 40-60° C., 10 h.

For product 23a (n=11, AA=Glu(2PhiPr)Gly), product 22a (274 mg, 0.274 mmol) in DCM (15 mL) was stirred in the dark with (PNP)$_2$CO (418 mg, 1.372 mmol) and DIEA (0.143 mL, 0.823 mmol) for 15 h. The solvent was removed on a rotovap and the product was purified on a column, eluent 4% MeOH, 0.2% AcOH in CHCl$_3$. Yield 260 mg (81%). MS: 1180.7 [M+NH$_4$]$^+$.

For product 23b (n=11, AA=PheCit), a solution of 22b (419 mg, 0.42 mmol), (PNP)$_2$CO (766 mg, 2.52 mmol) and DIEA (263 µL, 1.52 mmol) in dioxane (4 mL) was stirred in the dark at 50° C. for 15 h and all volatiles were removed on a rotovap. The residual DIEA was removed by two consecutive evaporations of DMF on a rotovap at 40° C./oil pump vacuum and the product was purified on a column, eluent CHCl$_3$:EtOAc:MeOH (4.5:5:0.5) followed by CHCl$_3$:MeOH (9:1). Yield 390 mg (80%). MS: 1181.2 [M+NH$_4$]$^+$, 1164.2 [M+1]$^+$.

For product 23c (n=11, AA=ValCit), a solution of 22c (273 mg, 0.287 mmol), (PNP)$_2$CO (874 mg, 2.88 mmol) and DIEA (0.3 mL, 1.72 mmol) in 1,4-dioxane (22 mL) was stirred in the dark for 24 h at 50° C. The solvent was removed on rotovap at 40° C./oil pump and the product was purified on a column, eluent: CHCl$_3$:EtOAc:MeOH=16:3:1 followed by 12-15% MeOH in CHCl$_3$ Yield 163 mg (51%). MS: 1116.0 [M+1]$^+$.

Product 23d (n=11, AA=AlaAsn(DMCP)) was prepared as described in the preparation of 23b. The product was purified on a column, eluent CHCl$_3$:EtOAc:MeOH (9:2:1). Yield 77%. MS: 1144.0 [M+NH$_4$]$^+$; 1127.3 [M+1]$^+$.

Product 23e (n=11, AA=PheLys(Me)$_2$) was prepared as described for 23a and purified on a column, eluent: 10% MeOH, 0.2% AcOH in CHCl$_3$. Yield 63%. MS: 1163.1 [M+1]$^+$.

Product 23f (n=11, AA=Leu) was prepared as described for 23c using only 5 equivalents of (PNP)$_2$CO and 3 equivalents of DIEA applying heat for 24 h. The product was purified on a column, eluent gradient of MeOH (7-12%) in CHCl$_3$. Yield 75%. MS: 972 [M+1]$^+$.

Product 23g (n=11, AA=Asn(DMCP)) was prepared as described for 23f and the crude product was used in the following step without additional purification. MS: 1073.4 [M+18]$^+$.

For product 23h (n=11, AA=Cit), solution of 22h (340 mg, 0.40 mmol), (PNP)$_2$CO (608 mg, 2.00 mmol) and DIEA (208 µL, 1.20 mmol) in DCM (4 mL) was stirred in the dark at 30° C. for 15 h and all volatiles were removed on a rotovap. The residual DIEA was removed by two consecutive evaporations of DMF on a rotovap at 40° C./oil pump vacuum and the product was purified on a column, eluent CHCl$_3$:EtOAc:MeOH (7:2.5:0.5) followed by a gradient of MeOH (8-14%) in CHCl$_3$. Yield 390 mg (80%). MS: 1034.3 [M+NH$_4$]$^+$; 1016.9 [M+1]$^+$.

Product 23i (n=23, AA=PheCit) was prepared as described in the preparation of 23b and purified on a column, eluent CHCl$_3$:EtOAc:MeOH (4.5:5:0.5) followed by a gradient of MeOH (6-12%) in CHCl$_3$. Yield 86%. MS: 1711.4 [M+NH$_4$]$^+$; 1694.4 [M+1]$^+$.

Product 23j (PEG 1000K AA=PheCit) was prepared as described in the preparation of 23b and purified on a column, eluent CHCl$_3$:EtOAc:MeOH (4.5:5:0.5) followed by a gradient of MeOH (6-12%) in CHCl$_3$. Yield 72%.

Product 23k (n=23, AA=ValCit) was prepared as described in the preparation of 23b, and the product purified with HPLC. Column: Luna (Phenomenex) 5u, C-8, 100 A. Mobile phase: ACN—H$_2$O (F$_3$CO$_2$H 0.01%), ACN gradient 30-37%, 31 min. Yield: 530 mg (48%). MS: 1666.4 [M+Na]$^+$; 1644.2 [M+1]$^+$.

PEG-AA-PABC-PNP 24a-c, AA Deprotection.

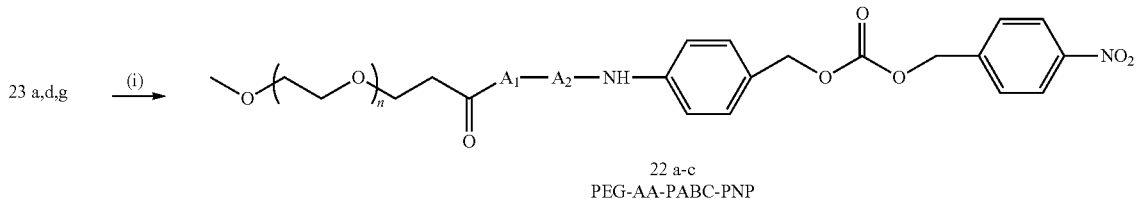

22 a-c
PEG-AA-PABC-PNP

Conditions: (i) TFA/H$_2$O=3:1, 5° C., 2-3 h.

Product 24a (n=11, AA=GluGly). Product 23a (250 mg, 0.215 mmol) was stirred in a 3% TFA solution of CHCl$_3$ (16 mL) for 35 min, concentrated on a rotovap and dried in vacuo. Yield 224 mg (100%) (MS: 1062.6 [M+NH$_4$]$^+$; 1045.9 [M+1]$^+$.

Product 24b (n=11, AA=AlaAsn-PABC-PNP). Compound 23d was stirred for 1.5 h in a mixture of TFA:DCM (3:1) and all volatiles were removed on a rotovap at 20° C. The product was purified on a column, eluent gradient of MeOH (6-12%) in CHCl$_3$. Yield 30%. MS: 1066.7 [M+Na]$^+$, 1062.0 [M+NH$_4$]$^+$; 1045.2 [M+1]$^+$.

Product 24c (n=11, AA=Asn). A reaction flask with 23g (160 mg, 0.143 mmol) was chilled to 0° C. and a cold mixture of TFA:H$_2$O (9:1) (12.5 mL) was added. The mixture was stirred for 1.5 h and was diluted with cold H$_2$O (50 mL). The stirring was continued for 20 min at 20° C. The precipitate was filtered off and rinsed with $H_2O$. All volatiles were removed on a rotovap at 40° C. and the product was purified on a column, eluent $CHCl_3$:EtOAc:MeOH:AcOH=4.5:3.5:1.2:0.02. Yield 43 mg (30%). MS: 974.0 $[M+1]^+$.

TABLE 4

Final PEG-L-$A_1A_2$-PABC used for DPC preparation compound

| $PEG_n$-AA-PABA | $PEG_n$-AA-(PNP) | AA $A^1$ | $A^2$ | size |
|---|---|---|---|---|
| 22 | 23a | Glu(2PhiPr) | Gly | n = 11 |
| 22 | 23b | Phe | Cit | n = 11 |
| 22 | 23c | Val | Cit | n = 11 |
| 22 | 23d | Ala | Asn(DMCP) | n = 11 |
| 22 | 23e | Phe | Lys($CH_3)_2$ | n = 11 |
| 22 | 23f | Leu | — | n = 11 |
| 22 | 23g | Asn(DMCP) | — | n = 11 |
| 22 | 23h | Cit | — | n = 11 |
| 22 | 23i | Phe | Cit | n = 23 |
| 22 | 23j | Phe | Cit | 1 kDa |
| 22 | 23k | Val | Cit | n = 23 |
|  | 24a | Glu | Gly | n = 11 |
|  | 24b | Ala | Asn | n = 11 |
|  | 24c | Asn | — | n = 11 |

Example 2

Linkage of Protease Cleavable Masking Agents to Amine-Containing Polymers—Formation of P-Acylamidobenzyl Carbamate Linkages A. Modification of Melittin with Protease Cleavable Masking Agents.

1×mg of melittin peptide and 10×mg HEPES base at 1-10 mg/mL peptide was masked by addition of 2-6×mg of amine-reactive p-nitrophenyl carbonate or N-hydroxysuccinimide carbonate derivatives of the NAG-containing protease cleavable substrate. The solution was then incubated at least 1 h at room temperature (RT) before injection into animals.

B. Modification of Polyamines with Protease Cleavable Masking Agents.

Activated (amine reactive) carbonates of p-acylamidobenzyl alcohol derivatives are reacted with amino groups of amphipathic membrane active polyamines in $H_2O$ at pH>8 to yield a p-acylamidobenzyl carbamate.

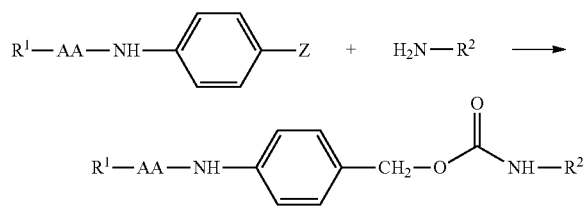

$R^1$ comprises an ASGPr ligand (either protected or unprotected) or a PEG,
$R^2$ is an amphipathic membrane active polyamine,
AA is a dipeptide (either protected or unprotected), and
Z is an amine-reactive carbonate.

To x mg polymer was added 12×mg of HEPES free base in isotonic glucose. To the buffered polymer solution was added 2× to 16×mg 200 mg/ml dipeptide masking agent in DMF. In some applications, the polymer was modified with 2×mg dipeptide masking agent followed by attachment of siRNA. The polymer-siRNA conjugate was then further modified with 6× to 8×mg dipeptide masking agent.

Example 3 siRNAs siRNAs had the following sequences:

```
Factor VII siRNA
sense:
                                            (Seq ID 1)
(Chol)-5' GfcAfaAfgGfcGfuGfcCfaAfcUfcAf(invdT) 3' antisense:
                                            (Seq ID 2)
5' pdTsGfaGfuUfgGfcAfcGfcCfuUfuGfcdTsdT 3'
or
sense:
                                            (Seq ID 3)
5' GGAUfCfAUfCfUfCfAAGUfCfUfUfACfdTsdT 3' antisense:
                                            (Seq ID 4)
5' GUfAAGACfUfUfGAGAUfGAUfCfCfdTsdT 3'
or
sense:
                                            (Seq ID 5)
(NH2C6)GfuUfgGfuGfaAfuGfgAfgCfuCfaGf(invdT) 3' antisense:
                                            (Seq ID 6)
pCfsUfgAfgCfuCfcAfuUfcAfcCfaAfcdTsdT 3'
or
sense:
                                            (Seq ID 23)
5' (NH2C6)uGuGfcAfaAfgGfcGfuGfcCfaAfcticAf(invdT) 3' antisense:
                                            (Seq ID 24)
5' pdTsGfaGfuUfgGfcAfcGfcCfuUfuGfcdTsdT 3'

Factor VII siRNA(primate)
sense:
                                            (Seq ID 7)
(chol)-5' uuAGGfuUfgGfuGfaAfuGfgAfgCfuCfaGf(invdT)
3' antisense:
                                            (Seq ID 8)
5' pCfsUfgAfgCfuCfcAfuUfcAfcCfaAfcdTsdT 3'

ApoB siRNA:
sense:
                                            (Seq ID 9)
(cholC6SSC6)-5' GGAAUCuuAuAuuuGAUCcAsA 3' antisense:
                                            (Seq ID 10)
5' uuGGAUcAAAuAuAAGAuUCcscsU 3'
AhaI siRNA:
sense:
                                            (Seq ID 11)
(NH2C6)GfgAfuGfaAfgUfgGfaGfaUfuAfgUf(invdT) 3'
antisense:
                                            (Seq ID 12)
pdAsCfuAfaUfcUfcCfaCfuUfcAfuCfcdTsdT 3'

Luc siRNA
sense:
                                            (Seq ID 13)
(chol) 5'-uAuCfuUfaCfgCfuGfaGfuAfcUfuCfgAf(invdT)-
3'
```

```
                            -continued
antisense:
                                              (Seq ID 14)
5'-UfcGfaAfgUfaCfuCfaGfcGfuAfaGfdTsdT-3'
or sense:
                                              (Seq ID 15)
(NH2C6)cuuAcGcuGAGuAcuucGAdTsdT 3' antisense:
                                              (Seq ID 16)
UCGAAGuACUcAGCGuAAGdTsdT 3'

Eg5-KSP
sense:
                                              (Seq ID 17)
(NH2C6)UfcGfaGfaAfuCfuAfaAfcUfaAfcUf(invdT) 3' antisense:
                                              (Seq ID 18)
pAfGfuUfaGfuUfuAfgAfuUfcUfcGfadTsdT 3'
or sense:
                                              (Seq ID 19)
AGUuAGUUuAGAUUCUCGAdTsdT 3' antisense:
                                              (Seq ID 20)
(NH2C6) ucGAGAAucuAAAcuAAcudTsdT 3'

EGFP
sense:
                                              (Seq ID 21)
5' (NH2C6) AuAucAuGGccGAcAAGcAdTsdT 3' antisense:
                                              (Seq ID 22)
5' UGCUUGUCGGCcAUGAuAUdTsdT 3'
lower case = 2'-O-CH3 substitution
s = phosphorothioate linkage
f after nucleotide = 2'-F substitution
d before nucleotide = 2'-deoxy
```

RNA synthesis was performed on solid phase by conventional phosphoramidite chemistry on an ÄKTA Oligopilot 100 (GE Healthcare, Freiburg, Germany) and controlled pore glass (CPG) as solid support.

Example 4

Administration of RNAi Polynucleotides In Vivo, and Delivery to Hepatocytes

DPCs were prepared as described above. Six to eight week old mice (strain C57BL/6 or ICR, ~18-20 g each) were obtained from Harlan Sprague Dawley (Indianapolis Ind.). Mice were housed at least 2 days prior to injection. Feeding was performed ad libitum with Harlan Teklad Rodent Diet (Harlan, Madison Wis.). DPCs were synthesized as described herein. Conjugate solutions (0.4 mL) were injected by infusion into the tail vein. The compositions were soluble and nonaggregating in physiological conditions. Injection into other vessels, e.g. retro-orbital injection, are predicted to be equally effective. Wistar Han rats, 175-200 g were obtained from Charles River (Wilmington, Mass.). Rats were housed at least 1 week prior to injection. Injection volume for rats was typically 1 ml. Unless indicated otherwise, serum samples were taken and/or liver samples were harvested 48 hours after injection.

Serum ApoB Levels Determination.

Mice were fasted for 4 h (16 h for rats) before serum collection by submandibular bleeding. For rats blood was collected from the jugular vein. Serum ApoB protein levels were determined by standard sandwich ELISA methods. Briefly, a polyclonal goat anti-mouse ApoB antibody and a rabbit anti-mouse ApoB antibody (Biodesign International) were used as capture and detection antibodies respectively. An HRP-conjugated goat anti-rabbit IgG antibody (Sigma) was applied afterwards to bind the ApoB/antibody complex. Absorbance of tetramethyl-benzidine (TMB, Sigma) colorimetric development was then measured by a Tecan Safire2 (Austria, Europe) microplate reader at 450 nm.

Plasma Factor VII (F7) Activity Measurements.

Plasma samples from animals were prepared by collecting blood (9 volumes) (by submandibular bleeding for mice or from jugular vein for rats) into microcentrifuge tubes containing 0.109 mol/L sodium citrate anticoagulant (1 volume) following standard procedures. F7 activity in plasma is measured with a chromogenic method using a BIOPHEN VII kit (Hyphen BioMed/Aniara, Mason, Ohio) following manufacturer's recommendations. Absorbance of colorimetric development was measured using a Tecan Safire2 microplate reader at 405 nm.

Example 5

Delivery of siRNA to Liver Cells In Vivo Using a Amphipathic Membrane Active Polyacrylate Polyamine Reversibly Modified with Dipeptide Cleavable Masking Agents Polyacrylate Ant-41658-111 in 100 mM pH 7.5 HEPES buffer was modified 0.5 wt % with the activated disulfide reagent succinimidyloxycarbonyl-alpha-methyl-alpha(2-pyridyl-dithio)toluene (SMPT) (Pierce) to provide thiol reactive groups for subsequent attachment of siRNA. The thiol-reactive polymer was then diluted to 5 mg/mL in 60 mg/mL HEPES base. To this solution was added 10 mg/mL various described enzyme cleavable masking reagents. This amount represented a molar ratio of 1 polymer amine to 2 masking reagents. For the polymer modification reaction, a preferred molar ratio of polymer amines to masking reagents is 1:1 to 1:5. A more preferred ratio is 1:2 to 1:4. A more preferred ratio is 1:2. After 1 hour, acetate-protected thiol endogenous rodent factor VII siRNA (0.1 to 0.2 wt equivalents relative to polymer) was added to polymer solution. After incubation overnight, conjugates were further modified by addition of an N-acetylgalactosamine derivative of maleic anhydride (NAG-CDM; Table 5). NAG-CDM was added to 25 mg/mL and incubated for 30 minutes to 4 hours.

For NAG-CDM polymer modification, NAG-CDM was lyophilized from a 0.1% aqueous solution of glacial acetic acid. To the dried NAG-CDM was added a solution of polymer. Following complete dissolution of anhydride, the solution was incubated for at least 30 min at RT prior to animal administration. Reaction of d NAG-CDM with the polymer yielded:

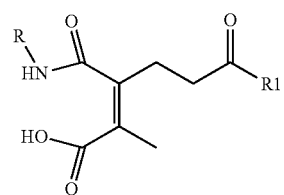

wherein R is the polymer and R1 comprises a ASGPr ligand (e.g. N-acetylgalactosamine).

As shown in Table 5, Factor VII expression was reduced 49-85% in animals treated with dipeptide agent masked DPCs.

TABLE 5

Knockdown of Factor VII in vivo in mice treated with PEG-AA-p-nitrophenyl-carbamate + NAG-CDM-DPCs.

| Dipeptide masking agent | Polymer dose (mg/kg) [a] | siRNA dose (mg/kg) [a] | % fVII activity [b] |
|---|---|---|---|
| PEG12-AlaAsn | 15 | 2 | 32 |
| PEG12-PheCit | 15 | 2 | 15 |
| PEG12-AsnGly | 15 | 2 | 51 |
| PEG24-PheCit | 1.5 | 0.25 | 23 |
| PEG12-Asn | 1.5 | 0.25 | 34 |
| PEG24-ValCit | 1.5 | 0.25 | 23 |

[a] mg polymer or siRNA per kg animal weight
[b] relative to naïve control

Example 6 siRNA In Vivo Delivery Using NAG/PEG-AA-P-Nitrophenyl-Carbamate Poly(Acrylate) DPCs A) PEG plus NAG Modification.

Polyacrylate Ant-41658-111 in 100 mM pH 7.5 HEPES buffer was modified 0.5 wt % with the activated disulfide reagent succinimidyloxycarbonyl-alpha-methyl-alpha(2-pyridyldithio)toluene (SMPT) from Pierce. The thiol-reactive polymer was diluted to 5 mg/mL in 60 mg/mL HEPES base. To this solution was added 10 mg/mL various PEG-AA-p-nitrophenyl-carbonate masking reagents. After 1 hour, acetate-protected thiol Factor VII siRNA was added to polymer solution at a polymer to siRNA ratio range of 5-10 to 1. After incubation overnight, NAG-AA-p-nitrophenyl-carbonate masking reagents were added to 40 mg/mL. After incubation for at least 30 minutes, but no longer than 4 hours, the DPC was injected into the tail vein of 20 g ICR mice. 48 hours after injection, a sample of serum was harvested and the levels of fVII were measured.

B) NAG Alone Modification.

Polyacrylate ANT-41658 111 in 100 mM pH 7.5 HEPES buffer was modified 0.5 wt % with the activated disulfide reagent succinimidyloxycarbonyl-alpha-methyl-alpha(2-pyridyldithio)toluene (SMPT) from Pierce. The thiol-reactive polymer was diluted to 5 mg/mL in 60 mg/mL HEPES base. Acetate-protected thiol siRNA factor VII was added to polymer solution at a polymer to siRNA ratio range of 5-10 to 1. After incubation overnight, NAG-AA-p-nitrophenyl-carbonate masking reagents were added to 50 mg/mL. After incubation for at least 30 minutes, but no longer than 4 hours the polymer-conjugated siRNA was injected into the tail vein of 20 gm ICR mice. 48 hours after injection, a sample of serum was harvested and the levels of fVII were measured.

TABLE 6

Knockdown of Factor VII in vivo in mice treated with PEG/NAG-AA-p-nitrophenyl-carbamate DPCs

| Masking Agent | amount [c] | Polymer dose (mg/kg) [a] | siRNA dose (mg/kg) [a] | % fVII activity [b] |
|---|---|---|---|---|
| 12 unit PEG12-PheCit followed NAG-PEG4-PheCit | 2× 8× | 15 | 2 | 27 |
| 24 unit PEG24-PheCit followed NAG-PEG4-PheCit | 2× 8× | 15 | 2 | 27 |
| PEG24-PheCit followed by NAG-PEG4-PheCit | 2× 8× | 1.5 | 2.5 | 23 |
| NAG-PEG4-PheCit | 10× | 15 | 2 | 44 |
| NAG-PEG2-GluGly | 10× | 1.5 | 2.5 | 27 |
| NAG-PEG2-PheCit | 10× | 1.5 | 2.5 | 72 |

[a] mg polymer or siRNA per kg animal weight
[b] relative to naïve control
[c] weight equivalents Example 7 siRNA In Vivo Delivery Using NAG/PEG-AA-P-Nitrophenyl-Carbamate Poly(Vinyl Ether) DPCs Amphipathic membrane active poly(vinyl ether) polyamine DW1360 modified with 10×wt equiv. dipeptide cleavable masking agents as described above for Polyacrylate Ant-41658-111 except that the masking agents retained protected groups during polymer modification. After polymer modification, amino acid protecting groups were removed by TFA and NAG acetate protecting groups were removed by incubation in the presence of a solution of 30 volume % triethylamine, 50% methanol and 20% water. The acetate deprotecting solution was removed by rotary evaporation. The masked polymer was coinjected into mice with cholesterol-ApoB siRNA conjugate.

TABLE 7

Knockdown of ApoB in vivo in mice co-injected with NAG-AA-p-nitrophenyl-carbamate poly(vinyl ether) and cholesterol-ApoB siRNA conjugate.

| polymer masking agent | Polymer dose (mg/kg) [a] | siRNA dose (mg/kg) [a] | % ApoB [b] |
|---|---|---|---|
| NAG-AsnGly | 25 | 5 | 67 |
| NAG-PheLys | 25 | 5 | 70 |
| NAG-GluGly | 25 | 5 | 48 |

[a] mg polymer or siRNA per kg animal weight

[b] relative to naive control

Example 8

In Vivo Knockdown of Endogenous ApoB Levels Following Delivery of ApoB siRNA with Melittin Delivery Peptide in Mice, Enzymatically Cleavable Masking Agents Melittin was reversibly modified with the indicated amount of enzymatically cleavable masking agents as described above. 200-300 μg masked melittin was then co-injected with the 50-100 μg ApoB siRNA-cholesterol conjugate. Effect on ApoB levels were determined as described above. Peptidase cleavable dipeptide-amidobenzyl carbamate modified melittin was an effective siRNA delivery peptide. The use of D-from melittin peptide is preferred in combination with the enzymatically cleavable masking agents. While more peptide was required for the same level of target gene knockdown, because the peptide masking was more stable, the therapeutic index was either not altered or improved (compared to masking of the same peptide with CDM-NAG).

TABLE 8

Inhibition of Factor VII activity in normal liver cells in mice treated with Factor VII-siRNA cholesterol conjugate and G1L-Melittin (D form) (Seq ID 25) reversibly inhibited with the indicated enzymatically cleavable masking agent.

| Peptide | amount[a] | NAG-linkage type | μg peptide | μg siRNA | percent knockdown |
|---|---|---|---|---|---|
| G1L d-Mel | 5× | CDM-NAG | 200 | 100 | 97 |
| (Seq ID 25) | 5× | NAG-AlaCit | 200 | 50 | 96 |
| | 5× | NAG-GluGly | 200 | 50 | 96 |
| | 5× | NAG-PEG$_4$-PheCit | 200 | 50 | 94 |
| | 5× | NAG-PEG$_7$-PheCit | 200 | 50 | 86 |
| | 5× | CDM-NAG | 300 | 50 | 98 |
| | 2× | NAG-GluGly | 300 | 50 | 95 |
| | 4× | NAG-GluGly | 300 | 50 | 95 |
| | 6× | NAG-GluGly | 300 | 50 | 82 |

[a] Amount of masking agent per Melittin amine used in the masking reaction.

Example 9

Tumor Targeting with Protease Cleavable DPCs

A) Target Gene Knockdown Measurement.

For all studies presented below an siRNA specific for the Aha1 gene transcript, the target gene. An siRNA to the enhanced green fluorescent protein (EGFP) was used as an off-target control. The Aha1 siRNA was complementary to a sequence motif in Aha1 that is 100% homologous in both the human and mouse gene. Therefore, delivery of Aha1 siRNA either into cells of the host or into tumor cells in the human xenograft results in mRNA cleavage and degradation. Using sequence motifs different in mouse and human Aha1 genes, PCR primers were designed that enabled quantitative measurement of both human Aha1 and mouse Aha1 mRNA levels in tissue samples that contained a mixed population of cell types. At 24, 48 or 72 hours after siRNA delivery, tumors were harvested with some healthy mouse liver tissue attached and were processed in Tri-Reagent (Invitrogen) for total RNA isolation. Both human and mouse Aha1 mRNA levels were then measured by qPCR assays, using human Cyc-A and mouse β-actin as internal reference genes. Aha1 mRNA levels in animals from mock-injected animals, or mice that received the off-target control GFP siRNA were considered 100%. Results are expressed as percent of Aha1 mRNA level relative to control and are shown in Tables below.

B) Orthotopic Hepatocellular Carcinoma (HCC) Tumor Model Mice.

HegG2, Hep3B, or HuH7 cells hepatocellular carcinoma were co-transfected with 2 expression vectors, pMIR85 a human placental secreted alkaline phosphatase (SEAP) vector and pMIR3 a neomycine/kanamycin-resistance gene vector, to develop cell lines with stable SEAP expressionCell were grown DMEM supplemented with 10% FBS and 300 ug/ml G418), collected, counted, and mixed with matrigel (BD Biosciences) (50% by volume). Athymic nude or Scid beige mice were anesthetized with ~3% isoflourane and placed in a sternal recumbent position. A small, 1-2 cm, midline abdominal incision was made just below the xyphoid. Using a moist cotton swab, the left lobe of the liver was gently exteriorized. The left lobe of the liver was gently retracted and a syringe needle was inserted into the middle of the left lobe. The syringe needle was inserted with the bevel down about 0.5 cm just under the capsule of the liver. 10 μl of cell/matrigel mixture, containing 100,000 cells, was injected into the liver using a syringe pump. The needle was left in the liver for a few moments (15-20 seconds) to ensure the injection was complete. SEAP-HepG2 cells were injected into athymic nude mice. SEAP-Hep3B and SEAP-HuH7 cells were injected into Scid beige mice. The syringe was then removed from the needle from the liver and a cotton swab was placed over the injection site to prevent leakage of the cells or bleeding. The Matrigel/cells mixture formed a mass that was visible and did not disappear after removal of the needle. The liver lobe was then gently placed back into the abdomen and the abdominal wall was closed. Sera were collected once per week after tumor implantation and subjected to SEAP assay to monitor tumor growth. For most studies, tumor mice were used 4-5 weeks after implantation, when tumor measurements are predicted to be around 4-8 mm based on SEAP values.

C) Colorectal Metastatic Tumor Model.

HT29 cells were grown in McCoy's 5a medium supplemented with 10% FBS, collected, counted, and mixed with matrigel (BD Biosciences) (50% by volume). Athymic nude mice were anesthetized with ~3% isoflourane and placed in a sternal recumbent position. A small, 1-2 cm, midline abdominal incision was made just below the xyphoid. Using a moist cotton swab, the left lobe of the liver was gently exteriorized. The left lobe of the liver was gently retracted and a syringe needle was inserted into the middle of the left lobe. The syringe needle was inserted with the bevel down about 0.5 cm just under the capsule of the liver. 5 μl of cell/matrigel mixture, containing ~40,000 cells, was injected into the liver using a syringe pump. The needle was left in the liver for a few moments (15-20 seconds) to ensure the injection was complete. The syringe was then removed from the needle and a cotton swab was placed over the injection site to prevent leakage of the cells or bleeding. The Matrigel/cells mixture formed a mass that was visible and did not disappear after removal of the needle. The liver lobe was then gently placed back into the abdomen and the abdominal wall was closed. Tumor mice were used 4-5 weeks after implantation.

Example 10

In Vivo Knockdown of Target Gene Expression in HepG2-SEAP Orthotopic Hepatocellular Carcinoma (HCC) Model Following PEG$_{24}$-Val-Cit DPC Administration (2011062805) Ant-129-1 polymer DPCs were modified (masked) with either 18× weight excess PEG$_{24}$-Phe-Cit masking agent (or PEG$_{24}$-Val-Cit masking agent) or with 7×PEG$_{550}$-CDM as described above. Aha1-siRNA (RD-09070) or GFP-siRNA (RD-05814; off-target control) was attached to the polymer as described above (4:1 weight ratio). DPCs were not purified by gel filtration prior to delivery, and no targeting ligand was added. A 320 μg (polymer weight) DPC conjugate in 200 μl isotonic glucose per animal was administered by tail vein injections (n=3 per group). After 24 hours, animals received second injection of 320 μg (polymer weight) DPC conjugate in 200 μl isotonic glucose. 48 hours after the second injection, serum samples were collected to assess toxicity by measuring liver enzyme (ALT and AST) and blood urea nitrogen (BUN) levels, followed by tissue harvest, and qPCR analysis.

Using PEG$_{24}$-Val-Cit-Ant-129-1-siRNA DPCs to delivery Aha1 siRNA, resulted 46% knockdown of the Aha1 gene in human tumor cells (Table 9). In contrast to human Aha1 knockdown levels, mouse Aha1 was knocked down 70% in response PEG$_{24}$-Val-Cit-Ant-129-1-siRNA DPC administration (Table 1). Compared to similar DPCs made with disustititied maleic anhydride masking agents (PEG$_{550}$-CDM), endogenous hepatocyte Aha1 knockdown was decreased. As indicated by ALT, AST and BUN levels, the PEG$_{24}$-Val-Cit DPCs were well tolerated and did not exhibit toxicity (Table).

TABLE 9

Aha1 knockdown in HepG2 liver tumor model by maleic anhydride modified vs. peptide cleavable modified Aha1 siRNA DPCs.

| | control siRNA | PEG$_{550}$-CDM DPC Aha1 siRNA | PEG$_{24}$-Val-Cit DPC Aha1 siRNA |
|---|---|---|---|
| human Aha1 levels (tumor) | 100 ± 8.0 | 54.4 ± 7.3 | 54.9 ± 7.6 |
| mouse Aha1 levels (hepatocytes) | 100 ± 9.2 | 7.5 ± 0.9 | 30.4 ± 3.1 |

TABLE 10

Blood chemistry toxicity markers following administration of maleic anhydride modified or peptide cleavable modified Aha1 siRNA DPCs.

| | control siRNA | PEG$_{550}$-CDM DPC Aha1 siRNA | PEG$_{24}$-Val-Cit DPC Aha1 siRNA |
|---|---|---|---|
| ALT | 44.3 ± 5.1 | 58.0 ± 37.5 | 35.0 ± 11.3 |
| AST | 81.7 ± 4.0 | 102.3 ± 57.5 | 67.7 ± 14.4 |
| BUN | 25.3 ± 4.2 | 23.0 ± 3.5 | 21.3 ± 1.2 |

Example 11

Knockdown of Targeting Gene Expression with Bispecific Antibody (bsAb)-Targeted DPCs (2011090701)

Ant-129-1 polymer was modified with 5× Dig-PheCit (Dig-FCit) masking agent as described above. siRNA was then attached to the conjugate. Finally, the Dig-FCit-Ant-129-1-siRNA conjugate was further modified with 8×(wt) PEG$_{12}$-FCit. Aha1-siRNA (RD-09070) or GFP siRNA (RD-05814) was attached at a 4:1 polymer:siRNA weight ratio. PEG$_{12}$-FCit DPCs were purified on Sephadex G50 spin columns to remove unbound reagents.

Cell targeting bispecific antibodies (bsAb) were made specific to heparan sulfate proteoglycan Glypican-3 (GPC3), a cell surface heparan sulfate proteoglycan known to be highly expressed in HepG2-SEAP cells, and digoxigenin (Dig). As a control, bispecific antibodies specific to the protein CD33 (marker of bone marrow-derived hematopoietic stem cells) and Dig were made. CD33 is not expressed by HepG2-SEAP cells. BsAbs were complexed with modified DPCs at a 1.25:1 weight ratio to provide an estimated 1:1 molar ratio. Complexes were formed in PBS at least 30 minutes prior to delivery.

DPCs were administered to HepG2-SEAP tumor bearing mice, either with or without bsAb targeting agent. Each animal (n=3 per group) received a single dose of 250 µg (polymer wt.) DPCs. DPCs were injected into tail vein of mice in 200 µl sterile PBS. Serum and tissue samples were harvested 48 hours later and analyzed as described above. As shown in Table 11, a single dose of bsAb targeting DPCs (250 µg polymer, 62.5 µg siRNA) resulted in target gene knockdown of 21-32%.

TABLE 11

Aha1 knockdown in HepG2 liver tumor model by peptide cleavable masking agent modified Aha1 siRNA DPCs targeted using bispecific antibodies.

| | Dig-FCit + PEG$_{12}$-FCit masking agent | | |
|---|---|---|---|
| | control siRNA | GPC-Dig bsAb Aha1 siRNA | CD33-Dig bsAb |
| human Aha1 levels (tumor) | 100 ± 10.1 | 78.6 ± 11.5 | 72.7 ± 2.4 | 68.1 ± 6.4 |
| mouse Aha1 levels (hepatocytes) | 100 ± 9.5 | 65.1 ± 8.1 | 73.7 ± 10.5 | 91.3 ± 8.3 |

Example 12

Knockdown of Targeting Gene Expression with Bispecific Antibody (bsAb)-Targeted DPCs DPCs were prepared as above except a) PEG$_{24}$-FCit was used instead of PEG$_{12}$-FCit and b) Dig-PEG$_{12}$-NHS was used to attach Dig to the polymer. PEG$_{24}$-FCit DPCs aggregated less than PEG$_{12}$-FCit DPCs and were smaller and more homogenous. In addition to being a non-labile linkage, Dig-PEG$_{12}$-NHS also contained a longer PEG. DPCs were complexes with bsAb and injected into animals as described above. Serum and tissue harvest was performed either at 24 or 48 hours post-injection. As shown in Table 12, a single dose of DPCs (250 µg polymer wt.) resulted in human Aha1 knockdown of 46-56% 24 hours post injection.

TABLE 12

Aha1 knockdown in HepG2 liver tumor model by Aha1 siRNA DPCs modified using peptide cleavable masking agents with increased PEG length.

| | Dig-PEG$_{12}$-NHS + PEG$_{24}$-FCit masking agent | |
|---|---|---|
| | GPC-Dig bsAb control siRNA | CD33-Dig bsAb Aha1 siRNA |
| human Aha1 levels (tumor) | 100 ± 3.1 | 54.1 ± 15.1 | 43.5 ± 6.6 |

Example 13

Targeting DPCs to Human Colorectal Adenocarcinoma Metastatic Liver Tumor Tissue by bsAb Targeted DPCs Ant-129-1 polymer was modified with 5× molar excess Dig-PEG$_{12}$-NHS and 8× weight excess PEG$_{24}$-FCit. Aha1 siRNA or GFP siRNA was attached to the modified polymer at a 4:1 polymer:siRNA weight ratio. DPCs were purified on a Sephadex G50 spin column to remove unbound reagents. Dig-DPCs were complexed with equimolar amount of IGF1R-Dig bsAb or CD33-Dig bsAb or no bsAb in sterile PBS at least 30 minutes prior to injections Animals containing HT29 tumor cells (human colorectal adenocarcinoma; ATCC Number HTB-38) were injected with the DPCs. HT29 cells overexpress the insulin-like growth factor-1 receptor protein (IGF 1R), and can bind and internalize an IGF1R-Dig bispecific antibody. Animals (n=3) received DPCs (320 μg polymer). Injections were repeated after 24 hours. Serum and tissue samples were collected 48 hours after the second dose. Knockdown of human Aha1 in tumor cells was 26-38% (Table 13). Compared to CDM-DPCs, FCit-DPCs showed less off target liver Aha1 knockdown (78-83% compared to 24-36%). FCit-DPCs also showed diminished liver accumulation compared to CDM-DPCs.

TABLE 13

Aha1 knockdown in HT29 colorectal adenocarcinoma metastatic liver tumor by dipeptide cleavable Aha1 siRNA DPC.

| | Ant-129-1 polymer Dig-PEG$_{12}$-NHS + PEG$_{24}$-FCit masking agent | | |
|---|---|---|---|
| | IGF1R-Dig bsAb | | |
| | control siRNA | Aha1 siRNA | CD33-Dig bsAb |
| human Aha1 levels (tumor) | 100 ± 4.9 | 72.3 ± 6.1 | 73.7 ± 3.2 | 62.0 ± 9.0 |
| mouse Aha1 levels (liver) | 100.0 ± 11 | 64.0 ± 5.0 | 75.7 ± 11 | 66.6 ± 5.8 |

Example 14

In Vivo Knockdown of Endogenous Aha1 in Liver Tumor

400 μg Lau41648-106 was modified with 8× (weight) PEG$_{12}$-ValCit or 16×PEG$_{24}$-PheCit. 100 μg Aha1 siRNA or 100 μg Eg5 control siRNA was attached to the modified polymer as described above. Animals containing Hep3B-SEAP tumor cells were injected with the DPCs. Serum and tissue samples were collected 48 hours after injection. Knockdown of human Aha1 in tumor cells was 26-38%.

TABLE 14

Aha1 knockdown in Hep3B-SEAP liver tumor by dipeptide cleavable Aha1 siRNA DPC.

| Polymer (400 μg) | modification | siRNA (100 μg) | Aha1 KD |
|---|---|---|---|
| Lau41648-106 | 8× PEG12-ValCit | Aha1 | 38 ± 0.02% |
| | 16× PEG24-Phecit | Aha1 | 41 ± 0.07% |
| | | EG5 | 13 ± 0.11% |

Example 15

In Vivo Circulation and Tissue Targeting of Masked Polymer

Figure 4:
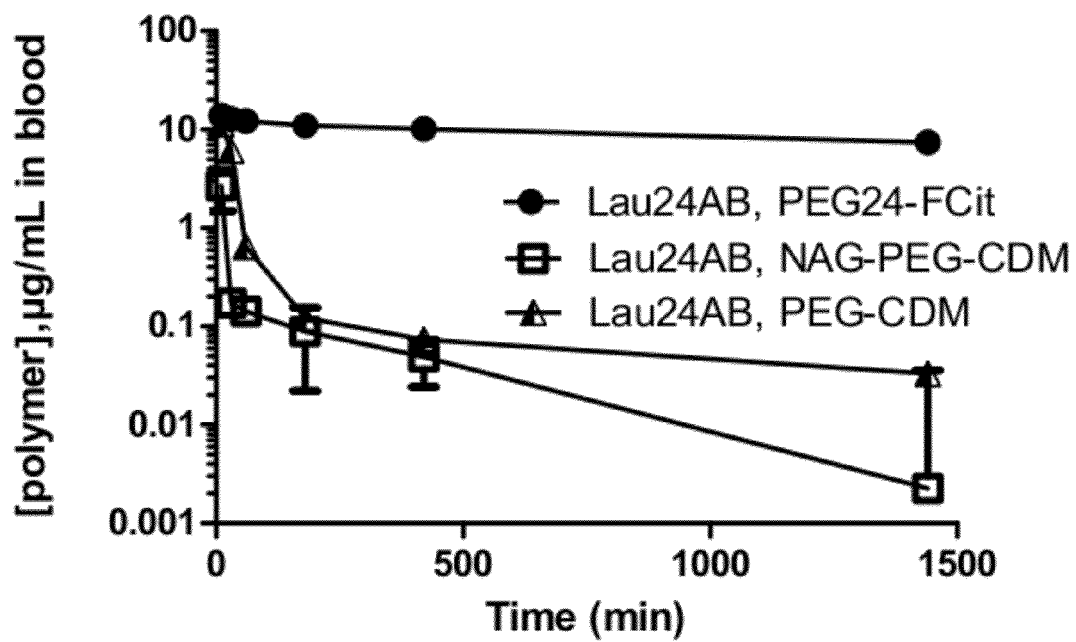
FIG. 4. Graph illustrating circulation times of polymers modified with a dipeptide masking agent vs. two different maleic anhydride based masking agents.

Lau24AB polyacrylate (100 μg) was treated with $^{125}$I-Bolton-Hunter (BH) reagent (50 μCi) in 50 mM HEPES pH 8.0 buffer for 1 hr at RT. The labeled polymer was purified in 2 ml Sephadex QEA spin column in water. The solution of labeled polymer was stored at 4° C. The unlabeled polymer was supplemented with $^{125}$I-labeled polymer to inject approx. 1 mg polymer having 0.2 μCi per 200 g rat. The mixture of labeled and unlabeled polymers (calculated for ~3.5 animals) was modified as described above with PEG$_{24}$-FCit or PEG-CDM (2 mg/ml polyacrylate, 14 mg/ml PEG-CDM reagent, 14 mg/ml NAG-PEG-CDM reagent, 16 mg/ml PEG$_{24}$-FCit reagent). Incubation time 1 hr. The reaction mix was then diluted with isotonic glucose to yield the injection dose per animal in a volume of 1 ml. 3 animals/group were injected. The animals were bled (0.1-0.2 ml) at the given times. The amount of polymer present in the samples was determined by counting in gamma counter. As shown in FIG. 4, polymer modified with the protease cleavable masking agent was cleared less rapidly from serum than polymer masked with the pH labile maleic anhydride masking agent. Increase circulation time is beneficial for targeting to non-liver tissue.

Example 16

Amphipathic Membrane Active Polymer Syntheses

A) Poly(Vinylacrylate)
i) RAFT Copolymerization of N-Boc-Ethylethoxy Acrylate and Propyl Methacrylate:

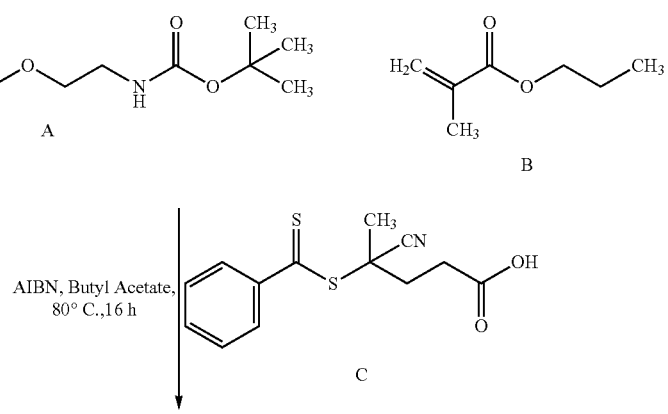

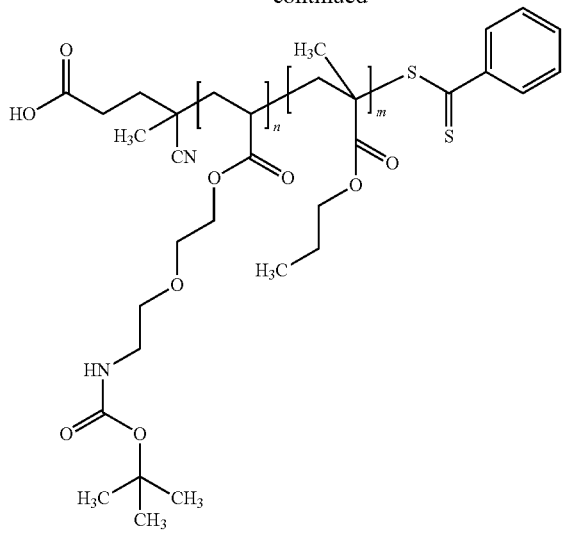

D wherein:
A is a boc protected ethyl-ethoxy amino acrylate
B is a propyl methacrylate
C is a RAFT agent CPCPA (4-Cyano-4-(phenylcarbonothioylthio)pentanoic acid)
And n and m are integers.

Removal of the boc protecting group after synthesis yields the amine monomers.

For other membrane active polymers, A can be also be protected ethyl, propyl, or butyl amino acrylate. B can be higher hydrophobic (10-24 carbon atoms, C18 shown) acrylate, lower hydrophobic (1-6 carbon atoms, C4 shown) acrylate, or a combination of lower an higher hydrophobic acrylates.

Copolymers consisting of Amine acrylate/C3 methacrylate were synthesized as follows. The monomers and RAFT agent were weighed and brought up into butyl acetate at the indicated ratios. AIBN (azobis-isobutyronitrile) was added and nitrogen was bubbled through the reaction at RT for 1 h. The reaction mixture was then placed into an oil bath at 80° C. for 15 h. The polymer was then precipitated with hexane, and further fractionally precipitated using a DCM/Hexane solvent system (see below). The polymer was then dried under reduced pressure. The polymer was deprotected with 7 ml 2M HCl in Acetic Acid for 30 min at RT. After 30 min 15 ml of water was added to the reaction mixture, and the mixture was transferred into 3.5 kDa MWCO dialysis tubing. The polymer was dialyzed overnight against NaCl and then another day against $dH_2O$. The water was then removed through lyophilization, and the polymer was dissolved in $dH_2O$.

Monomer Synthesis for (Ant 41658-111).

2,2'-Azobis(2-methylpropionitrile) (AIBN, radical initiator), 4-Cyano-4-(phenylcarbonothioylthio)pentanoic acid (CPCPA, RAFT Agent) and butyl acetate were purchased from Sigma Aldrich. Propyl Methacrylate monomer (Alfa Aesar) was filtered to remove inhibitors.

In a 2 L round-bottom flask equipped with a stir bar, 2-(2-aminoethoxy)ethanol (21.1 g, 202.9 mmol, Sigma Aldrich) was dissolved in 350 mL dichloromethane. In a separate 1 L flask, BOC anhydride (36.6 g, 169.1 mmol) was dissolved in 660 mL dichloromethane. The 2 L round-bottom flask was fitted with an addition funnel and BOC anhydride solution was added to the flask over 6 h. The reaction was left to stir overnight. In a 2 L separatory funnel, the product was washed with 300 ml each of 10% citric acid, 10% $K_2CO_3$, sat. $NaHCO_3$, and sat. NaCl. The product, BOC protected 2-(2-aminoethoxy)ethanol, was dried over $Na_2SO_4$, gravity filtered, and DCM was evaporated using rotary evaporation and high vacuum.

In a 500 ml round bottom flask equipped with a stir bar and flushed with argon, BOC protected 2-(2-aminoethoxy)ethanol (27.836 g, 135.8 mmol) was added, followed by 240 mL anhydrous dichloromethane. Diisopropylethyl amine (35.5 ml, 203.7 mmol) was added, and the system was placed in a dry ice/acetone bath. Acryloyl Chloride (12.1 ml, 149.4 mmol) was diluted using 10 ml of dichloromethane, and added drop-wise to the argon flushed system. The system was kept under argon and left to come to room temperature and stirred overnight. The product was washed with 100 mL each of $dH_2O$, 10% citric acid, 10% $K_2CO_3$, sat. $NaHCO_3$, and saturated NaCl. The product, BOC-amino ethyl ethoxy acrylate (BAEEA), was dried over $Na_2SO_4$, gravity filtered, and DCM was evaporated using rotary evaporation. The product was purified through column chromatography on 29 cm silica using a 7.5 cm diameter column. The solvent system used was 30% ethyl acetate in hexane. Rf: 0.30.

Fractions were collected and solvent was removed using rotary evaporation and high vacuum. BAEEA, was obtained with 74% yield. BAEEA was stored in the freezer.

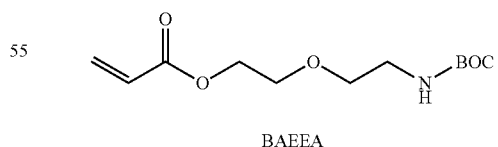

BAEEA

Polymer Ant-41658-111:

Solutions of AIBN (1.00 mg/mL) and RAFT agent (4-Cyano-4(phenylcarbonothioylthio)pentanoic acid (CPCPA), 10.0 mg/mL) in butyl acetate were prepared. Monomer molar feed ratio was 75 BAEEA:25 propyl methacrylate (CAS: 2210-28-8) with 0.108 CPCPA RAFT agent and 0.016 AIBN catalyst (0.00562 total mol).

BAEEA (1.09 g, 4.21 mmol) (A), propyl methacrylate (0.180 g, 1.41 mmol) (B), CPCPA solution (0.170 ml, 0.00609 mmol) (C), AIBN solution (0.150 ml, 0.000915 mmol), and butyl acetate (5.68 ml) were added to a 20 ml glass vial with stirrer bar. The vial was sealed with a rubber cap and the solution was bubbled with nitrogen using a long syringe needle with a second short syringe needle as the outlet for 1 hour. The syringe needles were removed and the system was heated to 80° C. for 15 h using an oil bath. The solution was allowed to cool to room temperature and transferred to a 50 ml centrifuge tube before hexane (35 ml) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 mL), precipitated in hexane (35 mL) and centrifuged once more. The supernatant was decanted and the bottom layer rinsed with hexane before the polymer was dried under reduced pressure for several hours. Molecular weight obtained through MALS: 73,000 (PDI 1.7); Polymer composition obtained using $H^1$NMR: 69:31 Amine:Alkyl.

Fractional Precipitation.

The dried, precipitated product was dissolved in DCM (100 mg/mL). Hexane was added until just after the cloud point was reached (~20 ml). The resulting milky solution was centrifuged. The bottom layer (thick liquid representing ~60% of polymer) was extracted and fully precipitated into hexane. The remaining upper solution was also fully precipitated by further addition of hexane. Both fractions were centrifuged, after which the polymer was isolated and dried under vacuum. Fraction 1: Mw 87,000 (PDI 1.5); Fraction 2: Mw 52,000 (PDI 1.5-1.6).

MALS Analysis.

Approximately 10 mg of the polymer was dissolved in 0.5 mL 89.8% dichloromethane, 10% tetrahydrofuran, 0.2% triethylamine. The molecular weight and polydispersity (PDI) were measured using a Wyatt Helos II multiangle light scattering detector attached to a Shimadzu Prominence HPLC using a Jordi 5μ, 7.8×300 Mixed Bed LS DVB column. Crude Polymer: MW: 73,000 (PDI 1.7), Fraction 1: MW 87,000 (PDI: 1.5), Fraction 2: MW 52,000 (PDI 1.5-1.6)

The purified BOC-protected polymer was reacted 2M HCl in Acetic Acid (7 ml) for 0.5 h to remove the BOC protecting groups and produce the amines. 15 mL $dH_2O$ were added to the reaction, the solution was transferred to 3500 MW cutoff cellulose tubing, dialyzed against high salt for 24 h, then against $dH_2O$ for 18 h. The contents were lyophilized, then dissolved in DI $H_2O$ at a concentration of 20 mg/ml. The polymer solution was stored at 2-8° C.

ii) Polymer Lau24B was prepared as above except the monomer feed ratio was 72.5 BAEEA:27.5 propyl methacrylate.

iii) Ant-129-1 was made as essentially as described above except the following monomers were used:

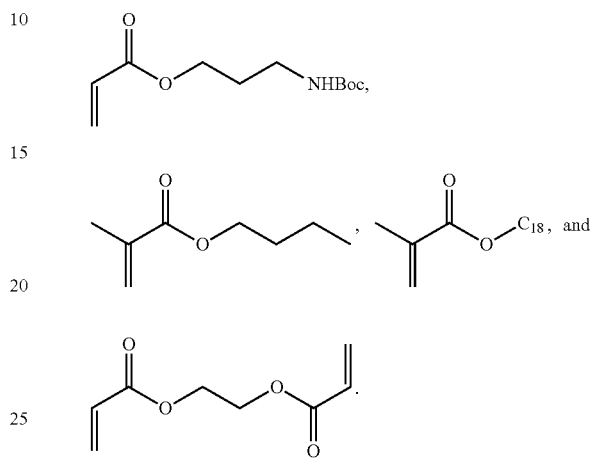

TABLE 15

| Ant-129-1 polymer synthesis reactants. | | | | | | |
|---|---|---|---|---|---|---|
| | MW (g/mol) | mol % | moles | mass (g) | volume (ml) | reaction moles |
| Monomers | | | | | | |
| N-Boc-amino-propyl acrylate | 229.27 | 70 | $3.94 \times 10^{-3}$ | 0.9031 | | 0.005627 |
| butyl methacrylate | 142.2 | 25 | $1.41 \times 10^{-3}$ | 0.2000 | 0.224 | 0.005627 |
| C18 methacrylate | 338.54 | 5 | $2.81 \times 10^{-4}$ | 0.0952 | | 0.005627 |
| ethylene glycol diacrylate | 170.16 | 5 | $2.81 \times 10^{-4}$ | 0.0479 | 0.44 | 0.005627 |
| other reagents | | | | | | |
| CPCPA (RAFT reagent) | 279.38 | 0.213 | $1.2 \times 10^{-5}$ | 0.0033 | 0.335 | 0.005627 |
| AIBN (initiator) | 164.21 | 0.032 | $1.8 \times 10^{-6}$ | 0.0003 | 0.295 | 0.005627 |
| butyl acetate | | | | | 5.272 | |
| target molecular weight | 100000 | | | | | |
| total units per CTA | 469.56 | | | | | |
| % CTA | 0.213 | | | | | |

For N-Boc-Amino-Propyl-Acrylate (BAPA), In a 500 ml round bottom flask equipped with a stir bar and flushed with argon, 3-(BOC-amino)1-propanol (TCI) (135.8 mmol) was added, followed by 240 mL anhydrous dichloromethane. Diisopropylethyl amine (203.7 mmol) was added, and the system was placed in a dry ice/acetone bath. Acryloyl Chloride (149.4 mmol) was diluted using 10 ml of dichloromethane, and added drop-wise to the argon flushed system. The system was kept under argon and left to come to room temperature and stirred overnight. The product was washed with 100 mL each of $dH_2O$, 10% citric acid, 10% $K_2CO_3$, sat. $NaHCO_3$, and saturated NaCl. The product, BOC-amino propyl acrylate (BAPA), was dried over $Na_2SO_4$, gravity filtered, and DCM was evaporated using rotary evaporation. The product was purified through column chromatography on 29 cm silica using a 7.5 cm diameter column. The solvent system used was 30% ethyl acetate in hexane. Rf: 0.30. Fractions were collected and solvent was removed using rotary evaporation and high vacuum. BAPA was obtained with 74% yield. BAPA was stored in the freezer.

Iv) Random Copolymerization of N-Boc-Ethylethoxy Acrylate and Propyl Methacrylate.

Copolymers consisting of Amine acrylate/$C_n$ methacrylate were synthesized as follows. The monomers were weighed brought up into dioxane at the indicated ratios. AIBN (azobisisobutyronitrile) was added and nitrogen was bubbled through the reaction at RT for 1 h. The reaction mixture was then placed into an oil bath at 60° C. for 3 h. The polymer was then dried under reduced pressure. The polymer was purified by GPC. After which the polymer fractions were deprotected with 7 ml 2M HCl in Acetic Acid for 30 min at RT. After 30 min, 15 ml of water was added to the reaction mixture, and the mixture was transferred into 3.5 kDa MWCO dialysis tubing. The polymer was dialyzed overnight against NaCl and then another day against $dH_2O$. The water was then removed through lyophilization, and the polymer was dissolved in $dH_2O$.

Polymer Lau41648-106.

Monomer molar feed ratio was 80 BAEEA:20 propyl methacrylate (CAS:2210-28-8) and 3% AIBN catalyst based on total monomer moles. BAEEA (6.53 g, 25.2 mmol) (A), propyl methacrylate (0.808 g, 6.3 mmol) (B), AIBN (0.155 g, 0.945 mmol), and dioxane (34.5 ml) were added to a 50 ml glass tube with stir bar. Compounds A and B were prepared described above in Example 16Ai. The reaction was set up in triplicate. Each solution was bubbled with nitrogen using a long pipette for 1 hour. The pipette was removed and each tube carefully capped. Then each solution was heated at 60° C. for 3 h using an oil bath. Each solution was allowed to cool to room temperature and combined in a round bottom. The crude polymer was dried under reduced pressure. Molecular weight obtained through MALS: 55,000 (PDI 2.1); Polymer composition obtained using $H^1$NMR: 74:26 Amine:Alkyl.

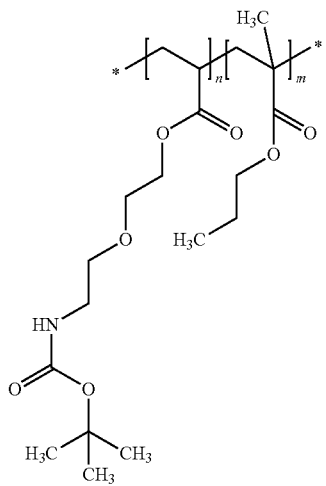

Lau41648-106

GPC Fractionation.

The dried crude polymer was brought up at 50 mg/ml in 75% dichloromethane, 25% tetrahydrafuran, and 0.2% triethylamine. The polymer was then fractionated on a Jordi Gel DVB $10^4$ Å-500 mm/22 mm column using a flow rate of 5 ml/min and 10 ml injections. An earlier fraction was collected from 15-17 minutes, and a later fraction was collected from 17-19 minutes. Fraction 15-17: Mw 138,000 (PDI 1.1); Fraction 17-19: Mw 64,000 (PDI 1.2).

MALS Analysis.

Approximately 10 mg of the polymer was dissolved in 0.5 mL 89.8% dichloromethane, 10% tetrahydrofuran, 0.2% triethylamine. The molecular weight and polydispersity (PDI) were measured using a Wyatt Helos II multiangle light scattering detector attached to a Shimadzu Prominence HPLC using a Jordi 5µ, 7.8×300 Mixed Bed LS DVB column. Crude Polymer: MW: 55,000 (PDI 2.1), Fraction 15-17: MW 138,000 (PDI: 1.1), Fraction 17-19: MW 64,000 (PDI 1.2)

The purified BOC-protected polymer was reacted 2M HCl in Acetic Acid (7 ml) for 0.5 h to remove the BOC protecting groups and produce the amines. 15 mL $dH_2O$ were added to the reaction, the solution was transferred to 3500 MW cutoff cellulose tubing, dialyzed against high salt for 24 h, then against $dH_2O$ for 18 h. The contents were lyophilized, then dissolved in DI $H_2O$ at a concentration of 20 mg/ml. The polymer solution was stored at 2-8° C.

V) Synthesis of Water-Soluble, Amphipathic, Membrane Active Poly(Vinyl Ether) Polyamine Terpolymers.

X mol % amine-protected vinylether (e.g., 2-Vinyloxy Ethyl Phthalimide) is added to an oven dried round bottom flask under a blanket of nitrogen in anhydrous dichloromethane. To this solution Y mol % lower hydrophobic group (e.g., propyl, butyl) vinylether and optionally Z mol % higher hydrophobic group (e.g., dodecyl, octadecyl) vinylether are added (FIG. 1). The solution is placed in a −50 to −78° C. bath, and the 2-vinyloxy ethyl phthalimide is allowed to precipitate. To this solution 10 mol % $BF_3 \cdot (OCH_2CH_3)_2$ is added and the reaction is allowed to proceed for 2-3 h at −50 to −78° C. Polymerization is terminated by addition of ammonium hydroxide in methanol solution. The polymer is brought to dryness under reduced pressure and then brought up in 1,4-dioxane/methanol (2/1). 20 mol eq. of hydrazine per phthalimide is added to remove the protecting group from the amine. The solution is refluxed for 3 h and then brought to dryness under reduced pressure. The resulting solid is dissolved in 0.5 mol/L HCl and refluxed for 15-min to form the hydrochloride salt of the polymer, diluted with distilled water, and refluxed for an additional hour. The solution is then neutralized with NaOH, cooled to room temperature (RT), transferred to molecular cellulose tubing, dialyzed against distilled water, and lyophilized. The polymer can be further purified using size exclusion or other chromatography. The molecular weight of the polymers is estimated using columns according to standard procedures, including analytical size-exclusion chromatography and size-exclusion chromatography with multi-angle light scattering (SEC-MALS).

Polymer DW1360.

An amine/butyl/octadecyl poly(vinyl ether) terpolymer, was synthesized from 2-vinyloxy ethyl phthalimide (5 g, 23.02 mmol), butyl vinylether (0.665 g, 6.58 mmol), and octadecyl vinylether (0.488 g, 1.64 mmol) monomers. 2-vinyloxy ethyl phthalimide was added to a 200 mL oven dried round bottom flask containing a magnetic stir bar under a blanket of Argon in 36 mL anhydrous dichloromethane. To this solution was added butyl vinyl ether and n-octadecyl vinyl ether. The monomers were fully dissolved at room temperature (RT) to obtain a clear, homogenous solution. The reaction vessel containing the clear solution was then placed into a −50° C. bath generated by addition of dry ice to a 1:1 solution of ACS grade denatured alcohol and ethylene glycol and a visible precipitation of phthalimide monomer was allowed to form. After cooling for about 1.5 min, $BF_3 \cdot (OCH_2CH_3)_2$ (0.058 g, 0.411 mmol) was added to initiate the polymerization reaction. The phthalimide monomer dissolved upon initiation of polymerization. The reaction was allowed to proceed for 3 h at −50° C. The polymerization was stopped by the addition of 5 mL of 1% ammonium hydroxide in methanol. The solvents were then removed by rotary evaporation.

The polymer was then dissolved in 30 mL of 1,4-dioxane/methanol (2/1). To this solution was added hydrazine (0.147 g, 46 mmol) and the mixture was heated to reflux for 3 h. The solvents were then removed by rotary evaporation and the resulting solid was then brought up in 20 mL of 0.5 mol/L HCl and refluxed for 15 minutes, diluted with 20 mL distilled water, and refluxed for an additional hour. This solution was then neutralized with NaOH, cooled to RT, transferred to 3,500 molecular weight cellulose tubing, dialyzed for 24 h (2×20 L) against distilled water, and lyophilized.

B) Melittin.

All melittin peptides were made using peptide synthesis techniques standard in the art. Suitable melittin peptides can be all L-form amino acids, all D-form amino acids (inverso). Independently of L or D form, the melittin peptide sequence can be reversed (retro).

The invention claimed is:

1. A compound for reversibly modifying an amphipathic membrane active polyamine comprising: a targeting ligand covalently linked to a dipeptide-amidobenzyl-carbonate having the structure represented by:

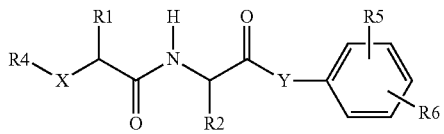

wherein
X is —NH—,
Y is —NH—,
R1 is —CH$_3$,
R2 is —(CH$_2$)$_3$—NH—C(o)—NH$_2$,
R4 is uncharged and comprises a targeting ligand,
R5 is at position 2, 4, or 6 and is —CH$_2$—O—C(O)—Z wherein Z is

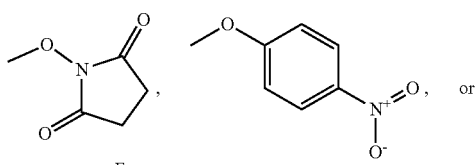, or

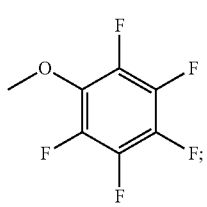

and
R6 is hydrogen.

2. The compound of claim 1 wherein the targeting ligand comprises an asialoglycoprotein receptor (ASGPr) ligand.

3. The compound of claim 2 wherein the ASGPr ligand is selected from the list consisting of: lactose, galactose, N-acetylgalactosamine, galactosamine, N-formylgalactosamine, N-propionylgalactosamine, N-n-butanoylgalactosamine, and N-iso-butanoyl-galactosamine.

4. The compound of claim 1 wherein Z is

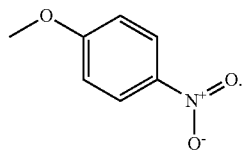

5. A delivery polymer for delivering an RNA interference (RNAi) polynucleotide to a cell in vivo comprising:

wherein:
P is an amphipathic membrane active polyamine,
M$^1$ is a targeting ligand linked to P via a dipeptide-amidobenzyl-carbamate linkage,
M$^2$ is a steric stabilizer linked to P via a dipeptide-amidobenzyl-carbamate linkage,
y and z are each integers greater than or equal to zero,
y+z has a value greater than 50% of the primary amines on polyamine P as determined by the quantity of amines on P in the absence of any masking agents, and
the dipeptide-amidobenzyl-carbamate linkage has the structure represented by:

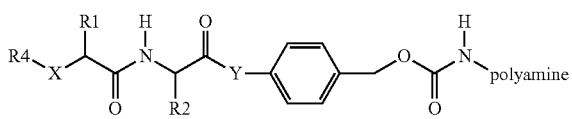

wherein

X is —NH—, —O—, or —CH$_2$—

Y is —NH— or —O—

R1 is —CH$_2$— phenyl, —CH—(CH$_3$)$_2$, —CH$_2$—CH—(CH$_3$)$_2$, —CH(CH$_3$)—CH$_2$—CH$_3$, —CH$_3$,

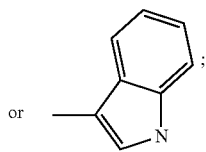

or

R2 is hydrogen, —(CH$_2$)$_3$—NH—C(O)—NH$_2$, —(CH$_2$)$_4$—N—(CH$_3$)$_2$, or —CH$_2$—C(O)—NH$_2$, R4 comprises the targeting ligand of M$^1$ or the steric stabilizer of M$^2$, and polyamine is the amphipathic membrane active polyamine.

6. The delivery polymer of claim 5 wherein the steric stabilizer is a polyethylene glycol (PEG).

7. The delivery polymer of claim 5 wherein the targeting ligand comprises an ASGPr ligand.

8. The delivery polymer of claim 7 wherein the ASGPr ligand is selected from the list consisting of: lactose, galactose, N-acetylgalactosamine, galactosamine, N-formylgalactosamine, N-propionylgalactosamine, N-n-butanoylgalactosamine, and N-iso-butanoyl-galactosamine.

9. The delivery polymer of claim 5 wherein the amphipathic membrane active polyamine is selected from the list consisting of: random, block, or alternating synthetic polymer.

10. The delivery polymer of claim 5 wherein the amphipathic membrane active polyamine is a melittin peptide.

11. The delivery polymer of claim 5 wherein the amphipathic membrane active polyamine is further covalently linked to the RNAi polynucleotide.

12. A method for delivering an RNAi polynucleotide to a cell in a mammal in vivo comprising: co-administering the RNAi polynucleotide with the delivery polymer of claim 5 to the mammal.

13. The method of claim 12 wherein the RNAi-polynucleotide is covalently linked to the delivery polymer.

14. The method of claim 12 wherein the cell is a hepatocyte or a hepatic cancer cell.

* * * * *

SEQUENCE LISTING

```
<160> NUMBER OF SEQ ID NOS: 25

<210> SEQ ID NO 1
<211> LENGTH: 20
<212> TYPE: DNA
<213> ORGANISM: Mus musculus

<400> SEQUENCE: 1
gcaaaggcgu gccaacucat                                              20

<210> SEQ ID NO 2
<211> LENGTH: 21
<212> TYPE: DNA
<213> ORGANISM: Mus musculus

<400> SEQUENCE: 2
tgaguuggca cgccuuugct t                                            21

<210> SEQ ID NO 3
<211> LENGTH: 21
<212> TYPE: DNA
<213> ORGANISM: Mus musculus

<400> SEQUENCE: 3
ggaucaucuc aagucuuact t                                            21

<210> SEQ ID NO 4
<211> LENGTH: 21
<212> TYPE: DNA
<213> ORGANISM: Mus musculus

<400> SEQUENCE: 4
guaagacuug agaugaucct t                                            21

<210> SEQ ID NO 5
<211> LENGTH: 20
<212> TYPE: DNA
<213> ORGANISM: Mus musculus

<400> SEQUENCE: 5
guuggugaau ggagcucagt                                              20

<210> SEQ ID NO 6
<211> LENGTH: 21
<212> TYPE: DNA
<213> ORGANISM: Mus musculus

<400> SEQUENCE: 6
cugagcucca uucaccaact t                                            21

<210> SEQ ID NO 7
<211> LENGTH: 24
```

```
<212> TYPE: DNA
<213> ORGANISM: Macaca fascicularis

<400> SEQUENCE: 7
uuagguuggu gauuggagcu cagt                                          24

<210> SEQ ID NO 8
<211> LENGTH: 21
<212> TYPE: DNA
<213> ORGANISM: Macaca fascicularis

<400> SEQUENCE: 8
cugagcucca uucaccaact t                                             21

<210> SEQ ID NO 9
<211> LENGTH: 21
<212> TYPE: DNA
<213> ORGANISM: Mus musculus

<400> SEQUENCE: 9
ggaaucuuau auuugaucca a                                             21

<210> SEQ ID NO 10
<211> LENGTH: 23
<212> TYPE: DNA
<213> ORGANISM: Mus musculus

<400> SEQUENCE: 10
uuggaucaaa uauaagauuc ccu                                           23

<210> SEQ ID NO 11
<211> LENGTH: 20
<212> TYPE: DNA
<213> ORGANISM: Mus musculus

<400> SEQUENCE: 11
ggaugaagug gagauuagut                                               20

<210> SEQ ID NO 12
<211> LENGTH: 21
<212> TYPE: DNA
<213> ORGANISM: Mus musculus

<400> SEQUENCE: 12
acuaaucucc acuucaucct t                                             21

<210> SEQ ID NO 13
<211> LENGTH: 23
<212> TYPE: DNA
<213> ORGANISM: Photinus pyralis

<400> SEQUENCE: 13
uaucuuacgc ugaguacuuc gat                                           23

<210> SEQ ID NO 14
<211> LENGTH: 21
<212> TYPE: DNA
<213> ORGANISM: Photinus pyralis

<400> SEQUENCE: 14
ucgaaguacu cagcguaagt t                                             21

<210> SEQ ID NO 15
<211> LENGTH: 21
```

```
<212> TYPE: DNA
<213> ORGANISM: Photinus pyralis

<400> SEQUENCE: 15
cuuacgcuga guacuucgat t                                              21

<210> SEQ ID NO 16
<211> LENGTH: 21
<212> TYPE: DNA
<213> ORGANISM: Photinus pyralis

<400> SEQUENCE: 16
ucgaaguacu cagcguaagt t                                              21

<210> SEQ ID NO 17
<211> LENGTH: 20
<212> TYPE: DNA
<213> ORGANISM: Mus musculus

<400> SEQUENCE: 17
ucgagaaucu aaacuaacut                                                20

<210> SEQ ID NO 18
<211> LENGTH: 21
<212> TYPE: DNA
<213> ORGANISM: Mus musculus

<400> SEQUENCE: 18
aguuaguuua gauucucgat t                                              21

<210> SEQ ID NO 19
<211> LENGTH: 21
<212> TYPE: DNA
<213> ORGANISM: Mus musculus

<400> SEQUENCE: 19
aguuaguuua gauucucgat t                                              21

<210> SEQ ID NO 20
<211> LENGTH: 21
<212> TYPE: DNA
<213> ORGANISM: Mus musculus

<400> SEQUENCE: 20
ucgagaaucu aaacuaacut t                                              21

<210> SEQ ID NO 21
<211> LENGTH: 21
<212> TYPE: DNA
<213> ORGANISM: Aequorea victoria

<400> SEQUENCE: 21
ccacaugaag cagcacgacu u                                              21

<210> SEQ ID NO 22
<211> LENGTH: 23
<212> TYPE: DNA
<213> ORGANISM: Aequorea victoria

<400> SEQUENCE: 22
aagucgugcu gcuucaugug guc                                            23

<210> SEQ ID NO 23
<211> LENGTH: 23
```

```
<212> TYPE: DNA
<213> ORGANISM: Mus musculus

<400> SEQUENCE: 23
ugugcaaagg cgugccaacu cat                                              23

<210> SEQ ID NO 24
<211> LENGTH: 21
<212> TYPE: DNA
<213> ORGANISM: Mus musculus

<400> SEQUENCE: 24
tgaguuggca cgccuuugct t                                                21

<210> SEQ ID NO 25
<211> LENGTH: 26
<212> TYPE: PRT
<213> ORGANISM: Apis florea

<400> SEQUENCE: 25

Leu Ile Gly Ala Ile Leu Lys Val Leu Ala Thr Gly Leu Pro Thr Leu
1               5                  10                  15

Ile Ser Trp Ile Lys Asn Lys Arg Lys Gln
            20                  25
```